United States Patent
Miyazaki et al.

(10) Patent No.: US 8,492,111 B2
(45) Date of Patent: Jul. 23, 2013

(54) ARYLALKYLAMINE COMPOUND AND PROCESS FOR PREPARING THE SAME

(75) Inventors: Hiroshi Miyazaki, Osaka (JP); Junko Tsubakimoto, Osaka (JP); Kosuke Yasuda, Osaka (JP); Iwao Takamuro, Osaka (JP); Osamu Sakurai, Osaka (JP); Tetsuya Yanagida, Osaka (JP); Yataka Hisada, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 0 days.

(21) Appl. No.: 12/776,153

(22) Filed: May 7, 2010

(65) Prior Publication Data
US 2010/0249049 A1 Sep. 30, 2010

Related U.S. Application Data

(62) Division of application No. 11/597,966, filed as application No. PCT/JP2005/009795 on May 27, 2005.

(30) Foreign Application Priority Data

May 28, 2004 (JP) ................................. 2004-158467

(51) Int. Cl.
| | |
|---|---|
| C07D 205/04 | (2006.01) |
| C07D 207/14 | (2006.01) |
| C07D 207/16 | (2006.01) |
| C07D 207/27 | (2006.01) |
| C07D 207/327 | (2006.01) |
| C07D 207/335 | (2006.01) |
| C07D 207/34 | (2006.01) |
| C07D 211/56 | (2006.01) |
| C07D 401/04 | (2006.01) |
| C07D 401/06 | (2006.01) |
| C07D 401/10 | (2006.01) |
| C07D 401/12 | (2006.01) |
| C07D 403/04 | (2006.01) |
| C07D 403/06 | (2006.01) |
| C07D 403/10 | (2006.01) |
| C07D 405/12 | (2006.01) |
| C07D 409/06 | (2006.01) |
| C07D 409/12 | (2006.01) |
| C07D 417/04 | (2006.01) |
| C07D 417/06 | (2006.01) |
| C07D 413/12 | (2006.01) |
| A61K 31/7056 | (2006.01) |
| A61K 31/402 | (2006.01) |
| A61K 31/4439 | (2006.01) |
| A61K 31/506 | (2006.01) |
| A61K 31/501 | (2006.01) |
| A61K 31/451 | (2006.01) |
| A61K 31/497 | (2006.01) |
| A61K 31/5377 | (2006.01) |
| A61K 31/397 | (2006.01) |
| A61K 31/5415 | (2006.01) |
| A61K 31/63 | (2006.01) |
| A61P 5/20 | (2006.01) |
| C07H 15/26 | (2006.01) |

(52) U.S. Cl.
USPC .......... 435/29; 514/25; 514/158; 514/210.01; 514/224.2; 514/235.5; 514/252.05; 514/255.05; 514/256; 514/275; 514/315; 514/342; 514/426; 536/17.4; 544/141; 544/238; 544/242; 544/330; 544/52; 546/244; 546/279.1; 548/557

(58) Field of Classification Search
None
See application file for complete search history.

(56) References Cited

U.S. PATENT DOCUMENTS

| | | |
|---|---|---|
| 4,785,119 A | 11/1988 | Hojo et al. |
| 5,688,938 A | 11/1997 | Brown et al. |
| 5,763,569 A | 6/1998 | Brown et al. |
| 6,362,231 B1 | 3/2002 | Sakai et al. |
| 7,084,167 B2 | 8/2006 | Ruat et al. |
| 7,157,498 B2 | 1/2007 | Dauban et al. |
| 2003/0232818 A1 | 12/2003 | Anderson et al. |
| 2004/0077619 A1 | 4/2004 | Kelly et al. |

FOREIGN PATENT DOCUMENTS

| | | |
|---|---|---|
| EP | 0218249 | 4/1987 |
| JP | 62-87565 | 4/1987 |
| JP | 11-221095 | 8/1999 |
| JP | 2001-220356 | 8/2001 |
| JP | 2001-226349 | 8/2001 |

(Continued)

OTHER PUBLICATIONS

Anderson et al., "Preparation of Naphthyridines as Antibacterial Compounds", Dec. 18, 2003—XP-002576070.
Corruble et al., "Structure-Selectivity Relationship in Alkyllithium-Aldehyde Condensations Using 3-Aminopyrrolidine Lithium Amides as Chiral Auxiliaries" 1998—XP-002576072.
Corruble et al., Structure-Selectivity Relationship in Alkyllithium-Aldehyde Condensations Using 3-Aminopyrrolidine Lithium Amides as Chiral Auxiliaries, J. Orig. Chem. 1998, 63-8266-8275.
European Search Report dated Apr. 14, 2010.
Sakai et al., "Preparation of 1-benzyl-3-(.alpha.-phenethylamino)pyrrolidine and optically active 3-aminopyrrolidine" Aug. 21, 2001.
Toyooka et al., "Fluorescent Chiral Derivatization Reagents for Carboxylic Acid Enantiomers in High-performance Liquid Chromatography", 1992—XP-002576071.

(Continued)

*Primary Examiner* — Sun Jae Loewe
(74) *Attorney, Agent, or Firm* — Birch, Stewart, Kolasch & Birch, LLP

(57) ABSTRACT

The present invention relates to an arylalkylamine compound represented by the following formula [I] or a pharmaceutically acceptable salt thereof, a process for preparing the same, and use of the above-mentioned compound as an activating compound (CaSR agonist) of a Ca sensing receptor, a pharmaceutical composition containing the above-mentioned compound as an effective ingredient, etc.

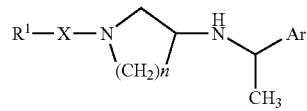

[I]

16 Claims, No Drawings

FOREIGN PATENT DOCUMENTS

| | | |
|---|---|---|
| WO | WO 93/04373 | 3/1993 |
| WO | WO 94/18959 | 9/1994 |
| WO | WO 95/11221 | 4/1995 |
| WO | WO 96/12697 | 5/1996 |
| WO | WO 97/37967 | 10/1997 |
| WO | WO 97/41090 | 11/1997 |
| WO | WO 98/01417 | 1/1998 |
| WO | WO 00/21910 | 4/2000 |
| WO | WO 01/34562 | 5/2001 |
| WO | WO 01/90069 | 11/2001 |
| WO | WO 02/12181 | 2/2002 |
| WO | WO 03/099776 | 12/2003 |
| WO | WO 03/099814 | 12/2003 |
| WO | WO2006/044454 * | 10/2004 |
| WO | WO 2006/044454 | 4/2006 |

OTHER PUBLICATIONS

Yamamoto et al., "Role of Advanced Glycation Endproducts in Adynamic Bone Disease," Clinical Calcium, vol. 11, No. 8, 2001, pp. 54-57.

Chen et al., caplus an 1999:795790.

D'Souza, The Calcium-sensing Receptor and Related Diseases, Arq Bras Endocrinol Metabol., 2006, 50(4), 628-639 (Abstract Only).

Hyperparathyroidism-Prevention-Information, http://www.answers.com/topic/hyperparathyroidism-prevention, 2010.

Medicine for Osteoporosis, http://www.righthealth.com/Health/Medicine%20For%20Osteoporosis-s?lid=yahoo-ads-sb-8805594729, 2010.

* cited by examiner

ARYLALKYLAMINE COMPOUND AND PROCESS FOR PREPARING THE SAME

This application is a Divisional of co-pending application Ser. No. 11/597,966, and for which priority is claimed under 35 U.S.C. §120. application Ser. No. 11/597,966 is a National Stage application of PCT International Application No. PCT/JP2005/009795, filed May 27, 2005, which designates the United States, and on which priority is claim under 35 U.S.C. §120. This application also claims priority under 35 U.S.C. §119(a) on Patent Application No. 2004-158467, filed in Japan on May 28, 2004. The entire contents of each of the above documents are hereby incorporated by reference.

TECHNICAL FIELD

The present invention relates to a novel arylalkylamine compound which has activating effect on Ca sensing receptor (CaSR) and useful as a medicament, and a process for preparing the same.

BACKGROUND ART

Parathyroid hormone (PTH) is a hormone having a physiological function which induces bone absorption to increase calcium (Ca) in blood, and has a role of maintaining homeostasis of Ca in blood. When hypersecretion of PTH is chronically continued, release of Ca from bone is continued whereby Ca concentration in blood increases and metabolic abnormality occurs. Thus, secretion and synthesis of PTH are strictly regulated by signal transmission through Ca sensing receptor (CaSR) which senses extracellular calcium ion ($Ca^{2+}$) concentration.

Ca sensing receptor (CaSR) is one of G protein-coupled receptors, and expressed on the surface of parathyroid cells, etc. When a compound (agonist) which activates the receptor binds to the receptor, it has been known that $Ca^{2+}$ concentration in cells increases, and secretion of PTH from the cells of parathyroid is suppressed.

[Non-Patent Literature 1] Brown et al., Nature, 366:575-580, 1993;
[Non-Patent Literature 2] Nemeth et al., Proc. Natl. Acad. Sci. USA, 95:4040-4045, 1998);
[Non-Patent Literature 3] Brown, Annu. Rev. Nutr., 20:507-533, 2000;
[Non-Patent Literature 4] Chattopadhyay, The International Journal of Biochemistry & Cell Biology, 32:789-804, 2000; and
[Non-Patent Literature 5] Coburn et al., Curr. Opin. Nephrol. Hypertens., 9:123-132, 2000).

A compound having an activating effect on CaSR (CaSR agonist), that is, a compound which selectively acts on CaSR to mimic or strengthen the action of $Ca^{2+}$ is also called as calcimimetics. On the other hand, a compound having an antagonistic effect on CaSR (CaSR antagonist), that is, a compound which suppresses or inhibits the action of $Ca^{2+}$ is also called as calcilytics.

With regard to CaSR agonist (calcimimetics) or CaSR antagonist (calcilytics), the following reports have been made. For example, in WO93/04373, WO94/18959, WO95/11221, WO96/12697, WO97/41090, WO98/01417, WO00/21910, WO01/34562, WO02/12181), WO01/90069, WO03/99814 and WO03/99776, amine derivatives having an activating effect or antagonistic effect on CaSR have been disclosed. It has been also reported that a compound having an activating effect on CaSR is expected to show an ameliorating effect on hyperparathyroidism through lowering PTH concentration in blood.

The present invention is to provide a novel arylalkylamine compound having an excellent Ca sensing receptor (CaSR) activating effect and a process for preparing the same.

DISCLOSURE OF THE INVENTION

Problems to be Solved by the Invention

To solve the problems, the present inventors have conducted extensive studies and as a result, they have found an arylalkylamine compound having excellent CaSR activating effect whereby the present invention has been accomplished.

That is, the present invention relates to an arylalkylamine compound represented by the formula [I]:

$$R^1-X-N(CH_2)_n-\overset{H}{N}-\overset{Ar}{\underset{CH_3}{C}}H \quad [I]$$

[The symbols in the formula represent the following meanings.
Ar: represents optionally substituted aryl or optionally substituted heteroaryl,
  here, the cyclic portion of the heteroaryl is a bicyclic heterocyclic ring in which 5- to 6-membered monocyclic heterocyclic ring containing 1 or 2 hetero atom(s) and benzene ring are fused;
$R^1$: represents a group selected from the group consisting of
  optionally substituted cylic hydrocarbon group, and
  optionally substituted heterocyclic group;
n: is an integer of 1 to 3;
X: represents single bonding arm, —$CH_2$—, —CO—, —$(CH_2)_m$—CO—, —$CH(R^2)$—CO—, —$(CH_2)_p$—Y—$(C(R^3)(R^4))_q$—CO—, —NH—CO— or —$N(R^5)$—CO—;
  in the above-mentioned respective definitions of the X, the bonding arm described at the left end represents a bond with $R^1$;
m is an integer of 1 to 3;
p is an integer of 0 to 2;
q is an integer of 0 to 2;
Y: represents —O— or —$SO_2$—;
$R^2$: represents phenyl or lower alkyl;
$R^3$, $R^4$: each independently represents hydrogen atom or lower alkyl;
$R^5$: represents lower alkyl;
provided that the ring portion of the group represented by $R^1$ is neither naphthylidine nor partially saturated group thereof, and, when X is —$CH_2$— or —CO—, $R^1$ is not naphthyl.]
or a pharmaceutically acceptable salt thereof.

Also, it relates to a pharmaceutical composition containing the above-mentioned arylalkylamine compound represented by the formula [I] or a pharmaceutically acceptable salt thereof as an effective ingredient.

Further, it relates to a method for treatment or prophylaxis comprising administering an effective amount of the above-mentioned compound [I] or a pharmaceutically acceptable salt thereof to a patient, and a use of the same for the preparation of a pharmaceutical composition containing the above-mentioned compound [I] or a pharmaceutically acceptable salt thereof as an effective ingredient. Also, it relates to the above-mentioned compound [I] or a pharmaceutically acceptable salt thereof, and a process for preparing the same.

Means to Solve the Problems

In the objective compound [I] of the present invention, plural optical isomers may be present (for example, among the compound [I], when n is 2 or 3, there exists an optical isomer in which the carbon atom at the 3-position of the nitrogen-containing cyclic structure portion is an asymmetric center). The present invention includes any of these isomers, and also includes a mixture thereof.

In the present invention, as the lower alkyl, the lower alkylthio, the lower alkylsulfonyl group, the lower alkoxy or the lower alkylamino, linear or branched ones having 1 to 6 carbon atoms may be mentioned, and particularly those having 1 to 4 carbon atoms may be mentioned.

Also, as the lower alkanoyl or the lower alkanoylamino, those having 2 to 7 carbon atoms, particularly those having 2 to 5 carbon atoms may be mentioned.

As the lower alkanoyl, either of lower alkyl-CO— or lower cycloalkyl-CO— is included.

As the lower cycloalkyl or the lower cycloalkenyl, those having 3 to 8 carbon atoms, particularly those having 3 to 6 carbon atoms may be mentioned.

As the lower alkylene, linear or branched ones having 1 to 6 carbon atoms, particularly having 1 to 4 carbon atoms may be mentioned.

As the lower alkenyl or the lower alkenylene, those having 2 to 7 carbon atoms, particularly those having 2 to 5 carbon atoms may be mentioned.

Moreover, as the halogen atom, fluorine, chlorine, bromine or iodine may be mentioned.

Also, as the optionally substituted amino group, cyclic amino (1-pyrrolidinyl, 1-piperidyl, 1-piperazinyl, 4-morpholinyl, etc.) is included.

In the objective compound [I] of the present invention, as the aryl portion of the "optionally substituted aryl" represented by Ar, monocyclic or bicyclic aryl may be mentioned.

More specifically, for example, phenyl, naphthyl, etc., may be mentioned.

As the heteroaryl portion of the "optionally substituted heteroaryl" represented by Ar, there may be mentioned bicyclic heterocyclic group comprising a monocyclic 5- to 6-membered hetero ring containing 1 or 2 hetero atoms (selected from oxygen atom, sulfur atom and nitrogen atom) and a benzene ring being fused.

More specifically, for example, benzothienyl, etc., may be mentioned.

As substituent(s) of the "optionally substituted aryl" or the "optionally substituted heteroaryl" represented by Ar, halogen (F, Cl, Br, etc.), hydroxy, cyano, halo-lower alkyl, lower alkyl, lower alkoxy, lower alkylthio, etc., may be mentioned.

Among these, lower alkoxy group (methoxy, ethoxy, etc.), lower alkyl (methyl, etc.), etc. are preferable.

As the cyclic hydrocarbon group portion of the "optionally substituted cyclic hydrocarbon group" represented by $R^1$, there may be mentioned, for example, monocyclic or bicyclic hydrocarbon group having 3 to 11 carbon atoms, which may be saturated partially or completely.

More specifically, there may be mentioned, for example, monocyclic hydrocarbon group having 3 to 7 carbon atoms such as phenyl, cyclohexyl, cyclopentyl, cyclobutyl, cyclopropyl, etc., and bicyclic hydrocarbon group having 9 to 11 carbon atoms such as indanyl, indenyl, naphthyl, tetrahydronaphthyl, etc.

Among these cyclic hydrocarbon group, preferred are monocyclic hydrocarbon group such as phenyl, cyclohexyl, etc., and a bicyclic hydrocarbon group such as indanyl, indenyl, etc.

Among these, the monocyclic hydrocarbon group is more preferred, and phenyl and cyclopropyl, etc. are particularly preferred.

As the heterocyclic group portion of the "optionally substituted heterocyclic group" represented by $R^1$, there may be mentioned saturated or unsaturated monocyclic or bicyclic hetero ring containing 1 or more hetero atoms selected from nitrogen atom, oxygen atom and sulfur atom.

As the monocyclic ones, there may be mentioned hetero ring comprising saturated or unsaturated 5 to 7-membered ring, and containing 1 to 4 hetero atoms selected from nitrogen atom, oxygen atom and sulfur atom, etc.

Also, as the bicyclic ones, there may be mentioned hetero ring comprising two saturated or unsaturated 5 to 7-membered rings being fused, and containing 1 to 6 hetero atoms selected from nitrogen atom, oxygen atom and sulfur atom, etc.

As the monocyclic ones, more specifically, there may be mentioned, for example, monocyclic group such as pyrrolidinyl, imidazolidinyl, pyrazolidinyl, oxolanyl, thiolanyl, pyrrolinyl, imidazolinyl, pyrazolinyl, pyrrolyl, imidazolyl, pyrazolyl, triazolyl, tetrazolyl, furyl, oxazolyl, isooxazolyl, oxadiazolyl, thienyl, thiazolyl, isothiazolyl, thiadiazolyl, piperidyl, piperazinyl, morpholinyl, thiomorpholinyl, pyridyl, pyrimidinyl, pyradinyl, pyridazinyl, pyranyl, perhydroazepinyl, perhydrothiazepinyl, partially or completely saturated group thereof, and cyclic group in which hetero atom (N or S) of the above is/are oxidized (pyridyl-N-oxide, etc.), etc.

Among these, pyrrolyl, thienyl, thiazolyl, piperazinyl, pyridyl, pyrimidinyl, pyradinyl, pyridazinyl, etc. are preferred.

Also, as the bicyclic ones, there may be mentioned, for example, bicyclic group such as indolinyl, isoindolinyl, indolyl, indazolyl, isoindolyl, benzimidazolyl, benzotriazolyl, benzothiazolyl, benzoxazolyl, benzodioxolanyl, benzothienyl, benzofuryl, thienopyridyl, thiazolopyridyl, pyrrolopyridyl, pyrrolopyrimidinyl, cyclopentapyrimidinyl, quinolyl, isoquinolyl, quinoxalinyl, quinazolinyl, phthalazinyl, cinnolinyl, chromanyl, isochromanyl, benzothiazinanyl, partially or completely saturated group thereof, and cyclic group in which a hetero atom (N or S) of the above is/are oxidized, etc.

Among these, indolyl, benzimidazolyl, benzotriazolyl, benzothienyl, quinolyl, phthalazinyl, benzothiazinanyl, etc. are preferred.

As the heterocyclic group portion of the "optionally substituted heterocyclic group" represented by $R^1$, among the above-mentioned monocyclic and bicyclic ones, the monocyclic ones are more preferred.

As substituent(s) of the "optionally substituted cyclic hydrocarbon group" or the "optionally substituted heterocyclic group" represented by $R^1$, for example, there may be mentioned those of the following Substituent group Q1.

<Substituent Group Q1>
halogen (Cl, F, Br, I, etc.)
cyano
nitro
oxo group
hydroxy
carboxy optionally substituted lower alkyl
(which may be optionally substituted by 1 or plural groups selected from halogen, cyano, nitro, oxo, carboxy, hydroxy, lower alkoxy and halo-lower alkoxy, etc.)
optionally substituted lower alkoxy
(which may be optionally substituted by 1 or plural groups selected from halogen, cyano, nitro, oxo, carboxy and hydroxy, etc.)
optionally substituted amino
(which may be optionally mono- or di-substituted by the group selected from lower alkyl, halo-lower alkyl, etc.)
optionally substituted 5 to 6-membered monocyclic heterocyclic group (tetrazole, pyridazinyl, or partially saturated cyclic group thereof, etc.)
(which may be optionally substituted by 1 or plural groups selected from halogen, cyano, nitro, oxo, carboxy, hydroxy, lower alkyl, halo-lower alkyl, lower alkoxy, halo-lower alkoxy and acyl, etc.)
optionally substituted phenyl
(which may be optionally substituted by 1 or plural groups selected from halogen, cyano, nitro, oxo, carboxy, hydroxy, lower alkyl, halo-lower alkyl, lower alkoxy, halo-lower alkoxy and acyl, etc.)
acyl
[for example, optionally substituted lower alkanoyl (which may be optionally substituted by 1 or plural groups selected from halogen, cyano, nitro, oxo, carboxy and hydroxy, etc.);
optionally substituted lower cycloalkylcarbonyl (which may be optionally substituted by 1 or plural groups selected from halogen, cyano, nitro, oxo, carboxy and hydroxy, etc.);
optionally substituted lower alkylsulfonyl (which may be optionally substituted by 1 or plural groups selected from halogen, cyano, nitro, oxo, carboxy and hydroxy, etc.);
esterified carbonyl
(lower alkoxycarbonyl which may be optionally substituted by 1 or plural groups selected from halogen, cyano, nitro, oxo, carboxy and hydroxy, etc.; carbonyl substituted by a group of D-glucuronic acid in which a hydrogen atom in hydroxy of its 2-position is eliminated, etc.);
optionally substituted aliphatic 5 to 6-membered nitrogen-containing heterocyclic group-CO— (pyrrolidinylcarbonyl, piperidinylcarbonyl, piperazinylcarbonyl, morpholinocarbonyl, etc.)
(which may be optionally substituted by 1 or plural groups selected from halogen; cyano; oxo; hydroxy; carboxy; lower alkyl which may be substituted by halogen, hydroxy, carboxy, lower alkoxy or halo-lower alkoxy, etc.; carbamoyl; lower alkylsulfonyl; and lower alkylsulfonylamino.);
optionally substituted carbamoyl
(which may be mono- or di-substituted by group(s) selected from the following Substituent group Q2.); and;
optionally substituted aminosulfonyl
(which may be mono- or di-substituted by group(s) selected from the following Substituent group Q2.); etc.]
<Substituent Group Q2>
optionally substituted lower alkyl
[which may be optionally substituted by 1 or plural groups selected from halogen; hydroxy; carboxy; aryl (phenyl, etc.); lower cycloalkyl; lower alkoxy; mono- or di-lower alkylamino; lower alkanoylamino; aliphatic nitrogen-containing 5 to 6-membered heterocyclic group (pyrrolidinyl, piperidinyl, morpholinyl, etc.) which may be substituted by oxo, etc.; and an acyl (lower alkanoyl, lower alkoxycarbonyl, carbamoyl, morpholinocarbonyl, etc.); etc.];
optionally substituted lower cycloalkyl
(which may be optionally substituted by 1 or plural groups selected from hydroxy; hydroxyl lower alkyl; and aliphatic nitrogen-containing 5 to 6-membered heterocyclic group (pyrrolidinyl, piperidinyl, morpholinyl, etc.) which may be substituted by oxo, etc.; etc.);
optionally substituted aliphatic nitrogen-containing 5 to 6-membered heterocyclic group (piperidinyl, etc.) [which may be optionally substituted by 1 or plural groups selected from lower alkyl and acyl (lower alkanoyl, lower alkylsulfonyl, lower alkoxycarbonyl, mono or di-lower alkylaminosulfonyl, mono or di-lower alkylaminocarbonyl, etc.), etc.]; and tetrahydropyranyl.

When $R^1$ is optionally substituted phenyl, the substituent(s) may desirably be carboxy, halogen (F, Cl, etc.), unsubstituted or substituted lower alkyl (carboxy-lower alkyl, halo-lower alkyl, etc.), unsubstituted or substituted lower alkoxy (halo-lower alkoxy, etc.), acyl (lower alkylsulfonyl, carbamoyl, hydroxyl-lower alkylcarbamoyl, lower alkylaminosulfonyl, mono- or di-lower alkylamino lower alkylaminosulfonyl, etc.), or optionally substituted 5 to 6-membered monocyclic heterocyclic group (tetrazole or partially saturated group thereof, etc.), etc.

As the "lower alkyl" represented by $R^2$, methyl or ethyl is preferred.

As the "lower alkyl" represented by $R^3$ and $R^4$, methyl or ethyl is preferred.

As the "lower alkyl" represented by $R^5$, methyl or ethyl is preferred.

Among the compound [I] of the present invention, as a preferred ones, there may be mentioned a compound having the following partial structure:

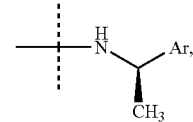

that is, a compound represented by the formula [I-e]:

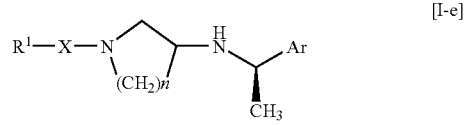

[the symbols in the formula have the same meanings as mentioned above].

More preferred compound groups are those wherein X is single bonding arm, —CO— or —$(CH_2)_m$—CO—. More preferred compounds are those wherein n is 1 or 2, and X is single bonding arm, —CO— or —$(CH_2)_m$—CO—.

Or else, there may be mentioned compound groups wherein n is 2, and X is single bonding arm.

Further, in any one of the above-mentioned compound groups, there may be mentioned compound groups wherein Ar is optionally substituted aryl.

Further, in any one of the above-mentioned compound groups, there may be mentioned compound groups wherein Ar is optionally substituted phenyl or optionally substituted naphthyl.

Further, in any one of the above-mentioned compound groups, there may be mentioned compound groups wherein Ar is a group optionally substituted by group(s) selected from halogen, hydroxy, cyano, halo-lower alkyl, lower alkyl, lower alkoxy and lower alkylthio.

Further, in any one of the above-mentioned compound groups, there may be mentioned compound groups wherein Ar is a group optionally substituted by group(s) selected from lower alkyl and lower alkoxy.

Further, in any one of the above-mentioned compound groups, there may be mentioned compound groups wherein the ring portion of the group represented by $R^1$ is cyclic hydrocarbon group, or monocyclic heterocyclic group.

Further, in any one of the above-mentioned compound groups, there may be mentioned compound groups wherein the cyclic group portion of the group represented by $R^1$ is the following (i), (ii) or (iii).

(i) monocyclic or bicyclic hydrocarbon group having 3 to 11 carbon atoms, which may be saturated partially or completely;
(ii) a monocyclic heterocyclic group, the hetero ring of which comprises one saturated or unsaturated 5 to 7-membered ring, and contains 1 to 4 hetero atom(s) selected from nitrogen atom, oxygen atom and sulfur atom; or
(iii) bicyclic heterocyclic group, the hetero ring of which comprises two saturated or unsaturated 5 to 7-membered rings being fused, and contain 1 to 6 hetero atom(s) selected from nitrogen atom, oxygen atom and sulfur atom.

Further, in any one of the above-mentioned compound groups, there may be mentioned compound groups wherein the cyclic group portion of the group represented by $R^1$ is the following (i), (ii) or (iii).

(i) monocyclic or bicyclic hydrocarbon group selected from phenyl, cyclohexyl, cyclopentyl, cyclobutyl, cyclopropyl, indanyl, indenyl, naphthyl, tetrahydronaphthyl, and partially or completely saturated group thereof;
(ii) monocyclic heterocyclic group selected from pyrrolidinyl, imidazolidinyl, pyrazolidinyl, oxolanyl, thiolanyl, pyrrolinyl, imidazolinyl, pyrazolinyl, pyrrolyl, imidazolyl, pyrazolyl, triazolyl, tetrazolyl, furyl, oxazolyl, isooxazolyl, oxadiazolyl, thienyl, thiazolyl, isothiazolyl, thiadiazolyl, piperidyl, piperazinyl, morpholinyl, thiomorpholinyl, pyridyl, pyrimidinyl, pyradinyl, pyridazinyl, pyranyl, perhydroazepinyl, perhydrothiazepinyl, partially or completely saturated group thereof, and a group in which the hetero atom(s) (N or S) thereof is/are oxidized; or
(iii) bicyclic heterocyclic group selected from indolinyl, isoindolinyl, indolyl, indazolyl, isoindolyl, benzimidazolyl, benzotriazolyl, benzothiazolyl, benzoxazolyl, benzodioxolanyl, benzothienyl, benzofuryl, thienopyridyl, thiazolopyridyl, pyrrolopyridyl, pyrrolopyrimidinyl, cyclopentapyrimidinyl, quinolyl, isoquinolyl, quinoxalinyl, quinazolinyl, phthalazinyl, cinnolinyl, chromanyl, isochromanyl, benzothiazinanyl, partially or completely saturated group thereof, and a group in which the hetero atom(s) (N or S) thereof is/are oxidized.

The compound [I] of the present invention may be in a free form or in a form of pharmaceutically acceptable salt.

As the pharmaceutically acceptable salt, there may be mentioned, for example, inorganic acid salt such as hydrochloride, sulfate, nitrate, phosphate or hydrobromide, etc., organic acid salt such as acetate, fumarate, oxalate, citrate, methanesulfonate, benzenesulfonate, p-toluenesulfonate or maleate, etc. Also, when the compound has a substituent such as carboxyl group, etc., there may be mentioned a salt with a base (for example, alkali metal salt such as sodium salt, potassium salt, etc. or alkaline earth metal salt such as calcium salt, etc.).

The compound [I] or a salt thereof of the present invention includes any of its intramolecular salt or adduct, or its solvate or hydrate, etc.

The objective Compound [I] (particularly Compound [I-e]) or a pharmaceutically acceptable salt thereof according to the present invention has an excellent CaSR activating effect. The pharmaceutical composition containing the objective compound of the present invention as an effective ingredient is useful as an effective ingredient of a medicament for treatment or prophylaxis of diseases of which condition is expected to be improved by activation of CaSR and/or suppression of PTH production (and/or lowering of PTH level in blood through the same) [for example, hyperparathyroidism (primary hyperparathyroidism, secondary hyperparathyroidism and ectopic hyperparathyroidism, etc.), etc.].

The objective compound [I] or a pharmaceutically acceptable salt thereof of the present invention has an excellent activating effect on CaSR. Also, it has high selectivity on CaSR.

Moreover, the objective compound [I] or a pharmaceutically acceptable salt thereof of the present invention shows various kinds of pharmacological effects through its activating effect on CaSR, in which production of PTH is suppressed, PTH level in blood is lowered in a living body, etc. Accordingly, the pharmaceutical composition containing the objective compound [I] or a pharmaceutically acceptable salt thereof of the present invention as an effective ingredient can be used for activating CaSR. Also, the pharmaceutical composition can be used for suppressing production of PTH. Also, it can be used for lowering PTH level in blood in a living body. Also, the pharmaceutical composition can be used for treatment or prophylaxis of diseases of which condition is expected to be improved by activation of CaSR and/or suppression of PTH production (and/or lowering of PTH level in blood through the same).

The compounds having an activating effect on CaSR have been known to show ameliorating effect on hyperparathyroidism through lowering of PTH concentration in blood as shown in, for example, WO93/04373, WO94/18959, WO95/11221, WO96/12697, WO97/41090, WO98/01417, WO03/99814 and WO03/99776.

Accordingly, the pharmaceutical composition containing as an effective ingredient the objective compound [I] or a pharmaceutically acceptable salt thereof of the present invention can be used for treatment or prophylaxis of diseases of which condition is expected to be improved by activation of CaSR and/or suppression of PTH production (and/or lowering of PTH level in blood through the same), i.e., hyperparathyroidism (primary hyperparathyroidism, secondary hyperparathyroidism and ectopic hyperparathyroidism, etc.), and the like.

A method of administering to a patient an effective amount of the compound [I] or a pharmaceutically acceptable salt thereof of the present invention, and a use for the preparation of the pharmaceutical composition containing as an effective ingredient the compound [I] or a pharmaceutically acceptable salt thereof of the present invention are applied to the above-mentioned objects, and included in the present invention.

Pharmacological effects such as an activating effect on CaSR and suppressing effect on PTH-production, etc. of the compounds of the present invention can be confirmed by the known methods (WO97/37967, WO93/04373, WO94/18959, WO97/41090, Nemeth et al., Proc. Natl. Acad. Sci USA, 95:4040-4045, 1998; Racke and Nemeth, J. Physiol., 468: 163-176, 1993; and Nemeth et al., J. Pharmacol. Exp. Ther. 308:627-635, 2004), or an equivalent method thereto.

Also, for the test of the suppressing effect on PTH-production, for example, there may be suitable used a method in which an effect of a test compound is assayed by using parathyroid cells of rats.

This method contains the following steps.
(i) Primary culture parathyroid cells of rat are prepared.
(Parathyroid cells are collected from rats and they are subjected to primary culture.)
(ii) The cells of (i) are incubated under the conditions of low calcium concentration [for example, in a medium with Ca concentration of about 1.5 mM or less (preferably 1.15 mM or less), etc.], in the presence of various concentrations of a test substance (or in the presence and absence of the test substance).
(iii) PTH production level is compared in the presence of various concentrations of the test substance.
(or PTH production level in the presence and absence of the test substance is compared.)
(iv) From the results of (iii), strength of an effect (suppressing effect or strengthening effect) of the test substance on the PTH production, or presence or absence of the effect of the same is determined.

In more detail, it can be carried out in the same manner as mentioned in the following Experimental example 2.

According to this method, preparation of cells is easy as compared with the conventional method using parathyroid cells of big animals (bovine, etc.). Also, change in PTH production can be observed with incubation for a suitable period of time, so that the test can be carried out stably and efficiently. Moreover, it enables a test for a large number of test substances.

Furthermore, it is advantageous for selecting a substance which shows potent effect in a living body by using cells of an animal (rat) which is the same as disease model usually employed in in vivo test.

PTH level lowering effect in living body can be detected by in vivo test using a known animal model (disease model of hyperparathyroidism, etc.).

As such an animal model, there may be applied, for example, rat adenine model, rat model of 5/6-nephrectomy, etc., more specifically, for example, the method described in the following mentioned Experimental examples 3 and 4, etc., may be applied to.

When the compound [I] or a pharmaceutically acceptable salt thereof of the present invention is used as an effective ingredient for medical use, it can be used with an inert carrier suitable for each administration method, and can be formulated into conventional pharmaceutical preparation (tablets, granules, capsules, powder, solution, suspension, emulsion, injection, infusion, etc.). As such a carrier, there may be mentioned, for example, a binder (Gum Arabic, gelatin, sorbitol, polyvinylpyrrolidone, etc.), an excipient (lactose, sugar, corn starch, sorbitol, etc.), a lubricant (magnesium stearate, talc, polyethylene glycol, etc.), a disintegrator (potato starch, etc.) and the like, which are pharmaceutically acceptable. When they are used as an injection solution or an infusion solution, they can be formulated by using distilled water for injection, physiological saline, an aqueous glucose solution, etc.

An administration method of the compound [I] or a pharmaceutically acceptable salt thereof of the present invention to be used for medical use is not particularly limited, and a usual oral or parenteral administration method (intravenous, intramuscular, subcutaneous, percutaneous, intranasal, and as others, transmucosal, enteral, etc.) can be applied to.

The dosage of the compound [I] or a pharmaceutically acceptable salt thereof of the present invention to be used for medical use may be optionally set in a range of an effective amount sufficient for showing a pharmacological effect, in accordance with the potency or characteristics of the compound to be used as an effective ingredient. The dosage may vary depending on an administration method, or an age, a body weight or conditions of a patient, and a usual dosage is set, for example, to a suitable amount in the range of 0.001 to 300 mg/kg per day.

The objective compound [I] of the present invention can be prepared by the following [Method A], [Method B], [Method C], [Method D], [Method E], [Method F], but the present invention is not limited by these.

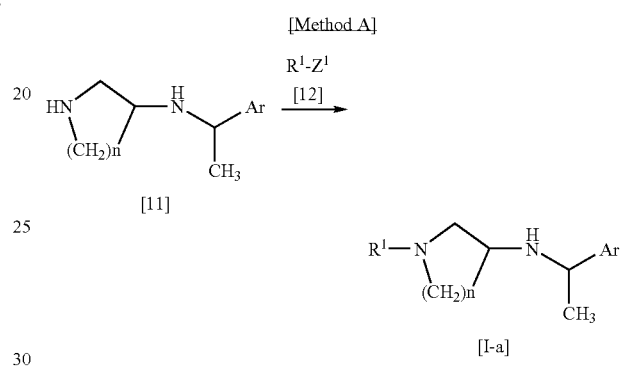

(wherein $Z^1$ represents a reactive residue, and the other symbols have the same meanings as defined above.)

Among the objective compounds [I] of the present invention, the compound represented by the formula [I-a] wherein X is single bonding arm can be prepared, for example, as follows.

First, the compound represented by the formula [11] or a salt thereof is reacted with the compound represented by the formula [12], and if desired, the resulting compound is converted into a pharmaceutically acceptable salt thereof to obtain the objective Compound [I-a].

As the reactive residue represented by $Z^1$, a conventionally used reactive residue such as halogen atom, lower alkylsulfonyloxy group, arylsulfonyloxy group, etc., can be suitably used, and halogen atom is particularly preferred. As a salt of Compound [11], there may be used, for example, a salt with an inorganic acid such as hydrochloride, sulfate, etc.

The reaction in the above-mentioned Method A can be carried out, for example, as shown in the following Reaction A1, or Reaction A2.

Reaction A1:

The reaction of Compound [11] or a salt thereof and Compound [12] can be carried out, for example, in a suitable solvent, and in the presence of a catalyst and a base.

As the catalyst, there may be suitably used a palladium catalyst [for example, palladium acetate, trisdibenzylideneacetone dipalladium, etc.].

Further, in order to accelerate the reaction, a trivalent phosphorus compound such as triphenylphosphine, BINAP (2,2'-bis(di-phenylphosphino-1,1'-binaphthyl)), biphenyl-2-yl-di-tert-butylphosphane, etc., may be added. Particularly, when a divalent palladium catalyst (palladium acetate, etc.) having no ligand is used as a catalyst, a trivalent phosphorous compound is added.

As the base, there may be suitably used, for example, cesium carbonate ($Cs_2CO_3$), sodium butoxide, an alkali metal amide (lithium hexamethyldisilazide, potassium hexamethyldisilazide, sodium hexamethyldisilazide, etc.), etc.

The present reaction suitably proceeds at 0 to 150° C., particularly at room temperature to 120° C.

The solvent may be any one which does not show an adverse affect on the reaction, and there may be suitably used, for example, tert-butanol, tetrahydrofuran, dioxane, toluene, 1-methyl-2-pyrrolidinone, 1,2-dimethoxyethane, diglyme, xylene or a mixture thereof.

Reaction A2:

The reaction of Compound [11] or a salt thereof and Compound [12] can be carried out, for example, in a suitable solvent in the presence of a base.

As such a base, there may be suitably used an inorganic base (for example, alkali metal hydride such as sodium hydride, etc., alkali metal carbonate such as sodium carbonate, potassium carbonate, etc., alkali metal alkoxide such as sodium butoxide, sodium methoxide, etc.) or an organic base (for example, triethylamine, diisopropylethylamine, N-methylmorpholine, pyridine, dimethylaniline, dimethylaminopyridine, etc.), etc.

The present reaction suitably proceeds at 20 to 200° C., particularly at 70 to 140° C.

As the solvent, there may be suitably used acetonitrile, methanol, ethanol, isopropyl alcohol, n-propyl alcohol, tert-butanol, acetone, N,N-dimethylformamide, dimethylsulfoxide, tetrahydrofuran, diethyl ether, dioxane, ethyl acetate, toluene, methylene chloride, dichloroethane, chloroform, N,N-dimethylacetamide, 1,3-dimethyl-2-imidazolidinone, 1-methyl-2-pyrrolidinone, 1,2-dimethoxyethane, diglyme, xylene or a mixture thereof.

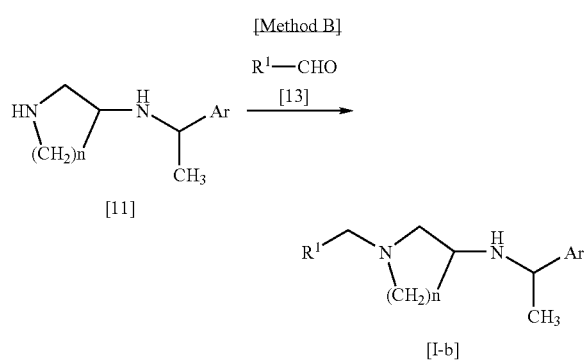

[Method B]

[11]

[I-b]

(wherein the symbols have the same meanings as defined above.)

Among the objective compound [I] of the present invention, the compound represented by the formula [I-b] in which X is —$CH_2$— can be prepared, for example, as follows.

First, the compound represented by the formula [11] or a salt thereof is reacted with a compound represented by the formula [13], and if desired, the resulting compound is converted into a pharmaceutically acceptable salt thereof to obtain the objective Compound [I-b].

As a salt of Compound [11], similar salts as mentioned above can be used.

The reaction of Compound [11] or a salt thereof and Compound [13] can be carried out in a suitable solvent in the presence of a reducing agent.

As the reducing agent, there may be suitably used sodium triacetoxyborohydride, sodium borohydride, sodium cyanoborohydride, etc.

Further, in order to accelerate the reaction, an organic acid such as acetic acid, propionic acid, etc. is preferably added.

The present reaction suitably proceeds at 0 to 60° C., particularly at 20 to 40° C.

The solvent may be any one which does not show an adverse affect on the reaction, and there may be suitably used, for example, acetonitrile, tetrahydrofuran, diethyl ether, dioxane, ethyl acetate, toluene, methylene chloride, dichloroethane, chloroform, 1,2-dimethoxyethane, xylene or mixture thereof. Among them, methylene chloride is particularly preferably used.

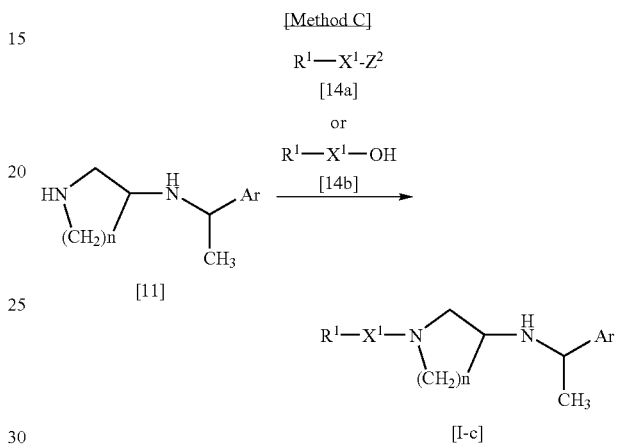

[Method C]

[11]

[I-c]

[wherein $X^1$ represents —CO—, —$(CH_2)_m$—CO—, —CH$(R^2)$—CO—, —$(CH_2)_p$—Y—$(C(R^3)(R^4))_q$—CO—, or —N($R^5$)—CO—, and other symbols have the same meanings as defined above.]

Among the objective compounds [I] of the present invention, the compound represented by the formula [I-c] wherein X is —CO—, —CH($R^2$)$_m$—CO—, —$(CH_2)_p$—Y—$(C(R^3)(R^4))_q$—CO—, or —N($R^5$)—CO— can be prepared, for example, as mentioned below.

First, the compound represented by the formula [11] or a salt thereof is reacted with the compound represented by the formula [14a] or [14b], and if desired, the resulting compound is converted into a pharmaceutically acceptable salt thereof to obtain the objective Compound [I-c].

As a salt of Compound [11], the same salt as mentioned above can be used.

The reaction of Compound [11] or a salt thereof and Compound [14a] can be carried out in a suitable solvent in the presence of a base.

As such a base, an organic base (for example, triethylamine, diisopropylethylamine, N-methylmorpholine, pyridine, dimethylaniline, dimethylaminopyridine, etc.), etc. may be preferably used.

The present reaction suitably proceeds at −20 to 50° C., particularly preferably at 10 to 30° C.

The solvent may be any one which does not shown an adverse affect on the reaction, and there may be suitably used, for example, acetonitrile, tetrahydrofuran, diethyl ether, dioxane, ethyl acetate, toluene, methylene chloride, dichloroethane, chloroform, 1,2-dimethoxyethane, xylene or a mixture thereof.

Also, the reaction of Compound [11] or a salt thereof and Compound [14b] can be carried out in a suitable solvent in the presence of a condensing agent, and if necessary in the presence or absence of an additive and/or a base.

As the condensing agent, there may be suitably used O-benzotriazol-1-yl-N,N,N',N'-tetramethyluronium hexafluorophosphate, DCC (dicyclohexylcarbodiimide), EDC (1-ethyl-3-(3-dimethylaminopropyl)carbodiimide), chloroformic acid esters (for example, ethyl chloroformate, isobutyl chloroformate), carbonyldiimidazole, etc.

Further, in order to accelerate the reaction, an additive such as 1-hydroxybenzotriazole, 1-hydroxysuccineimide, etc., or a base may be added together with the above-mentioned condensing agent.

As such a base, there may be suitably used an organic base (for example, triethylamine, diisopropylethylamine, N-methylmorpholine, pyridine, dimethylaniline, dimethylaminopyridine, etc.), alkali metal carbonate (sodium carbonate, potassium carbonate, etc.), etc.

The present reaction suitably proceeds at 0 to 100° C., particularly preferably at 20 to 50° C.

The solvent may be any one which does not show an adverse affect on the reaction, and there may be suitably used, for example, acetonitrile, N,N-dimethylformamide, tetrahydrofuran, diethyl ether, dioxane, ethyl acetate, toluene, methylene chloride, dichloroethane, chloroform, N,N-dimethylacetamide, 1,3-dimethyl-2-imidazolidinone, 1-methyl-2-pyrrolidinone, 1,2-dimethoxyethane, xylene or a mixture thereof.

sodium butoxide, etc., alkali metal hydroxide such as sodium hydroxide, potassium hydroxide, etc.) or an organic base (for example, triethylamine, diisopropylethylamine, N-methylmorpholine, pyridine, dimethylaniline, dimethylaminopyridine, etc.), etc.

The present reaction suitably proceeds at 0 to 60° C., particularly preferably at 10 to 30° C.

The solvent may be any one which does not shown an adverse affect on the reaction, and there may be suitably used, for example, acetonitrile, N,N-dimethylformamide, tetrahydrofuran, diethyl ether, dioxane, ethyl acetate, toluene, methylene chloride, dichloroethane, chloroform, N,N-dimethylacetamide, 1,3-dimethyl-2-imidazolidinone, 1-methyl-2-pyrrolidinone, 1,2-dimethoxyethane, xylene or a mixture thereof.

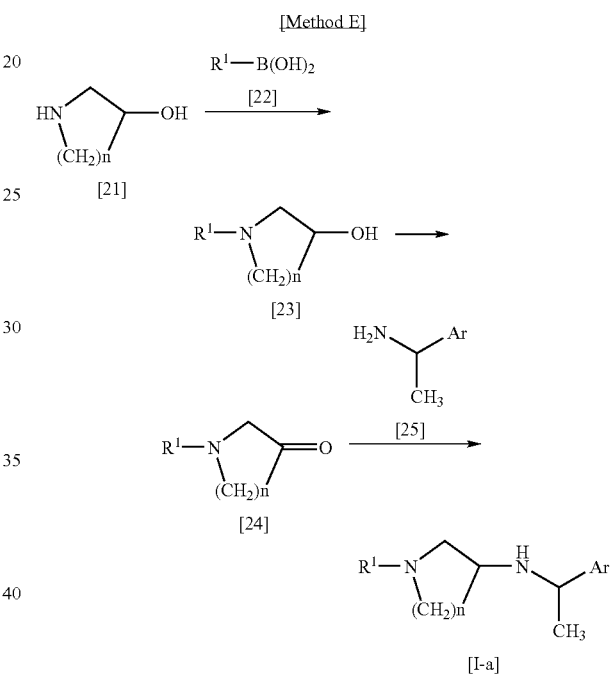

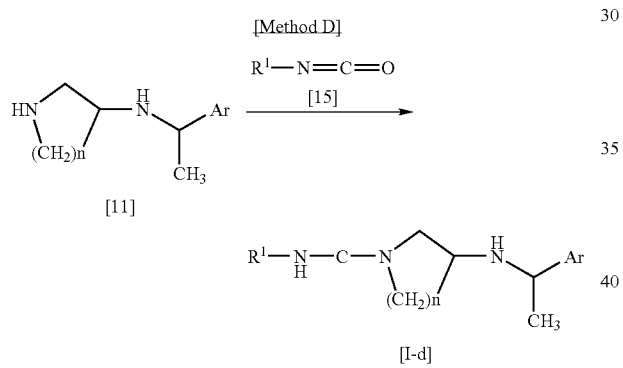

[the symbols in the formula have the same meanings as defined above.]

Among the objective compounds [I] of the present invention, the compound represented by the formula [I-d] wherein X is —NH—CO— can be prepared, for example, as mentioned below.

First, the compound represented by the formula [11] or a salt thereof is reacted with the compound represented by the formula [15], and if desired, the resulting compound is converted into a pharmaceutically acceptable salt thereof to obtain the objective Compound [I-d].

As a salt of Compound [11], the same salt as mentioned above can be used.

The reaction of Compound [11] or a salt thereof and Compound [15] can be carried out in a suitable solvent in the presence or absence of a base.

As such a base, there may be suitably used an inorganic base (for example, alkali metal hydride such as sodium hydride, etc., alkali metal carbonate such as sodium carbonate, potassium carbonate, etc., alkali metal alkoxide such as (wherein the symbols have the same meanings as defined above.)

The objective Compound [I-a] can be also prepared, for example, as follows.

First, a compound represented by the formula [21] or a salt thereof is reacted with a compound represented by the formula [22] to obtain a compound represented by the formula [23]. This is applied to an oxidation reaction to obtain a compound represented by the formula [24]. Compound [24] is reacted with a compound represented by the formula [25] or a salt thereof, and if desired, the resulting compound is converted into a pharmaceutically acceptable salt thereof to obtain the objective Compound [I-a].

As a salt of Compound [21] and [25], there may be used, for example, a salt with an inorganic acid such as a hydrochloride, a sulfate, etc.

The respective reactions in Method E can be carried out as follows.

The reaction of Compound [21] or a salt thereof and Compound [22] can be carried out in a suitable solvent and in the presence of a copper reagent.

As the copper reagent, copper acetate, etc. can be suitably used.

Further, in order to accelerate the reaction, a base is added. As such a base, there may be suitably used, for example, triethylamine, pyridine, etc.

Also, when water is mixed into the reaction system, the reaction rate is lowered. Accordingly, to prevent such a matter, a dehydrating agent such as Molecular Sieve 4A, etc. may be added in the reaction system.

The present reaction suitably proceeds at 0 to 40° C., particularly preferably at 10 to 30° C.

The solvent may be any one which does not show an adverse affect on the reaction, and there may be suitably used, for example, methylene chloride, dichloroethane or a mixture thereof, and, methylene chloride is particularly suitable.

Oxidation reaction of Compound [23] can be carried out according to the conventional method, and it can be carried out, for example, in a suitable solvent in the presence of an oxidizing agent.

As the oxidizing agent, there may be suitably used oxalyl chloride-dimethylsulfoxide, sulfur trioxide-pyridine complex, etc.

The present reaction suitably proceeds at −70 to 40° C., particularly preferably at −70 to 20° C.

The solvent may be any one which does not show an adverse affect on the reaction, and there may be suitably used, for example, methylene chloride, etc., when oxalyl chloride-dimethylsulfoxide is used as an oxidizing agent, and suitably used dimethylsulfoxide when sulfur trioxide-pyridine complex is used as an oxidizing agent.

The reaction of Compound [24] and Compound [25] or a salt thereof can be carried out in the same manner as in the reaction of Compound [11] and Compound [13] in the above-mentioned Method B.

[Method F]

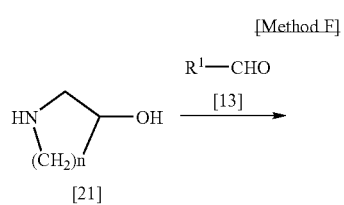

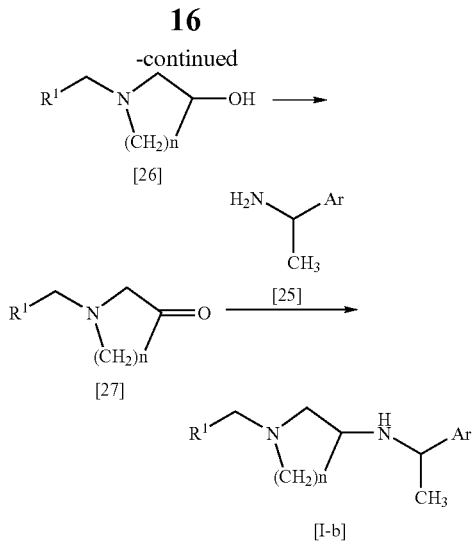

(wherein the symbols have the same meanings as defined above.)

The objective Compound [I-b] can be also prepared, for example, as follows.

First, a compound represented by the formula [21] or a salt thereof is reacted with the above-mentioned Compound [13] to obtain a compound represented by the formula [26]. This is applied to an oxidation reaction to obtain a compound represented by the formula [27]. Compound [27] is reacted with the above-mentioned Compound [25] or a salt thereof, and if desired, the resulting compound is converted into a pharmaceutically acceptable salt thereof to obtain the objective Compound [I-b].

The respective reactions in Method F can be carried out as follows.

The reaction of Compound [21] or a salt thereof and Compound [13] can be carried out in the same manner as in the reaction of the above-mentioned Compound [11] and Compound [13].

The oxidation of Compound [26] can be carried out in the same manner as in the oxidation of the above-mentioned Compound [23].

The reaction of Compound [27] and Compound [25] or a salt thereof can be carried out in the same manner as in the reaction of the above-mentioned Compound [24] and Compound [25].

[Preparation Method of Starting Compound]

Compound [11] which is a starting compound in the above-mentioned Method A, Method B, Method C and Method D can be prepared, for example, as follows.

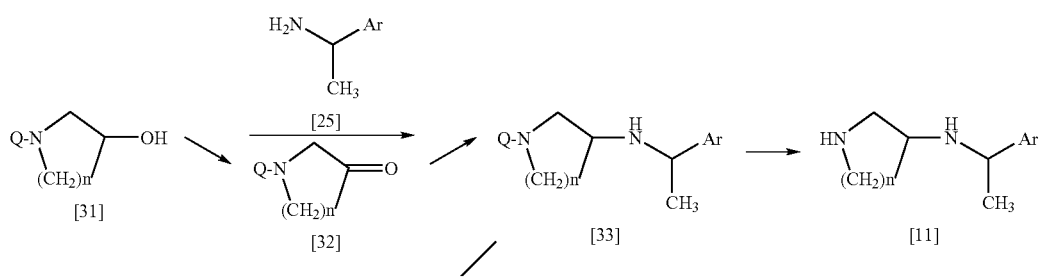

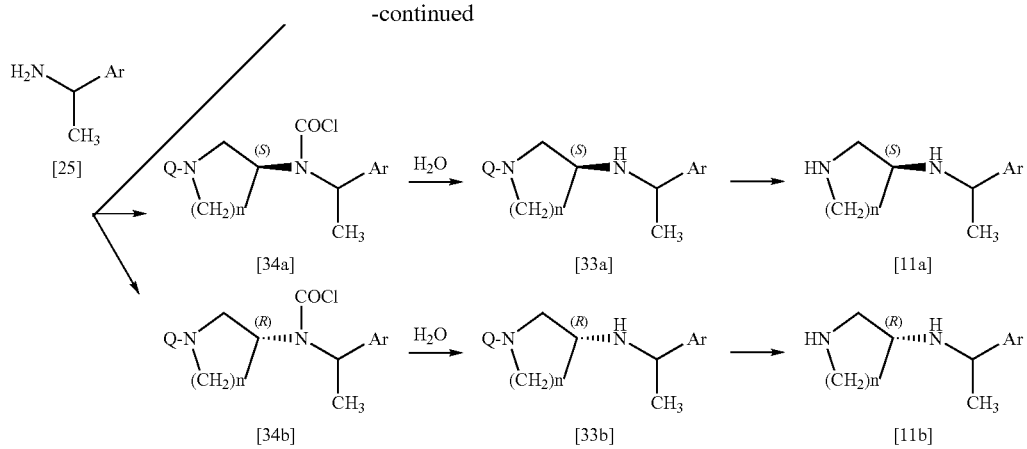

(wherein Q represents a protective group for amino group, and the other symbols have the same meanings as defined above.)

First, a compound represented by the formula [31] or a salt thereof is reacted with the above-mentioned Compound [25] or a salt thereof to obtain a compound represented by the formula [33].

Or else, Compound [31] is applied to oxidation to obtain a compound represented by the formula [32]. This is reacted with the above-mentioned Compound [25] or a salt thereof to obtain Compound [33].

By removing a protective group for amino group from Compound [33], Compound [11] can be obtained.

As the protective group for amino group represented by Q, any of the conventionally used protective groups for amino group such as t-butoxycarbonyl group, benzyloxycarbonyl group, trifluoroacetyl group, 9-fluorenylmethyloxycarbonyl group, etc. can be suitably used.

The respective reactions can be carried out as follows.

The reaction of Compound [31] and Compound [25] or a salt thereof can be carried out in a suitable solvent, in the presence of anhydrous trifluoromethanesulfonic acid, etc. and in the presence of a base. As such a base, there may be suitably used, for example, an organic base such as diisopropylethylamine, etc., and the like.

The present reaction suitably proceeds at −50° C. to room temperature, particularly preferably at −20° C. to room temperature.

The solvent may be any one which does not show an adverse affect on the reaction, and there may be suitably used, for example, acetonitrile, tetrahydrofuran, diethyl ether, dioxane, ethyl acetate, toluene, methylene chloride, dichloroethane, chloroform, 1,2-dimethoxyethane, xylene or a mixture thereof, and, particularly methylene chloride can be suitably used.

The oxidation of Compound [31] can be carried out in the same manner as in the oxidation of the above-mentioned Compound [23].

The reaction of Compound [32] and Compound [25] or a salt thereof can be carried out in the same manner as in the reaction of the above-mentioned Compound [24] and Compound [25].

Or else, it can be carried out by using titanium tetraisopropoxide, etc. as a condensing agent, and using sodium borohydride, etc., as a reducing agent.

Removal of the protective group for amino group (Q) from Compound [33] can be carried out in a conventional manner, and can be carried out, for example, by an acid treatment, a base treatment or a catalytic reduction, in a suitable solvent or without a solvent.

When n is 2 or 3, in Compound [33] and Compound [11], there exist optical isomers in which the carbon atom at the 3-position of the nitrogen-containing ring is a chiral center.

Such optically active Compound [33] and Compound [11] can be prepared from a diastereomer mixture [33], for example, as follows.

First, Compound [33] is reacted with a phosgene, and the resulting products (diastereomer mixture) are purified and separated by crystallization and/or column chromatography, if desired, to obtain optically active compounds represented by the formula [34a] and formula [34b].

Or else, an optically active compounds can be similarly obtained by reacting a carbamoyl chloride diastereomer mixture with an alcohol (tert-butanol, etc.) and separating the resulting carbamate diastereomer mixture using a column.

Compound [34a] or Compound [34b] is reacted with $H_2O$ to obtain a compound represented by the formula [33a] and formula [33b].

By removing a protective group for amino group from Compound [33a] or Compound [33b], the compound represented by the formula [11a] or formula [11b] can be prepared.

The reaction of Compound [33] and a phosgene (triphosgene, diphosgene, carbonyldiimidazole, 4-nitrophenylchloroformate, etc.) can be carried out in a suitable solvent in the presence of a base.

As such a base, there may be suitable used an organic base (for example, triethylamine, diisopropylethylamine, N-methylmorpholine, pyridine, dimethylaniline, dimethylaminopyridine, etc.), etc.

The present reaction suitably proceeds at −40 to 40° C., particularly preferably at −20° C. to room temperature.

The solvent may be any one which does not show an adverse affect on the reaction, and there may be suitably used, for example, acetonitrile, tetrahydrofuran, diethyl ether, dioxane, ethyl acetate, toluene, methylene chloride, dichloroethane, chloroform, 1,2-dimethoxyethane, xylene or a mixture thereof, and, particularly, methylene chloride can be suitably used.

The reaction of Compound [34a] or Compound [34b] and $H_2O$ can be carried out in a suitable solvent.

The present reaction suitably proceeds at room temperature to 120° C., particularly preferably at 70 to 100° C.

The solvent may be any one which does not show an adverse affect on the reaction, and there may be suitably used, for example, acetonitrile, N,N-dimethylformamide, dimethylsulfoxide, tetrahydrofuran, diethyl ether, dioxane, ethyl acetate, toluene, methylene chloride, dichloroethane, chloroform, N,N-dimethylacetamide, 1,3-dimethyl-2-imidazolidinone, 1-methyl-2-pyrrolidinone, 1,2-dimethoxyethane, xylene or a mixture thereof.

Removal of the protective group for amino group (Q) from Compound [33a] or Compound [33b] can be carried out in the same manner as in the removal of the protective group for amino group from the above-mentioned Compound [33].

Other starting compound can be prepared in the same manner according to the known methods and/or the methods described in the following Reference examples.

Also, the objective Compound [I] prepared by the above-mentioned preparation methods (Method A, Method B, Method C, Method D, Method E, Method F) can be further structurally converted into the other objective Compound [I] according to the methods described in the following Examples and/or the known methods or combination thereof.

Compound [I] according to the present invention or a starting compound thereof, prepared as mentioned above, can be isolated and purified as a free form or a salt thereof. The salt can be prepared by a conventional method for preparation of a salt. Isolation and purification can be carried out by conventional chemical procedures such as extraction, concentration, crystallization, filtration, recrystallization, various kinds of chromatography, etc.

EXAMPLE

In the following, the present invention is illustrated in more detail by Examples, but these Examples do not limit the present invention.

In Table A1, Table A2, Table B, Table CD, Table EF, Table X, Table Y and Reference example Table at the end of the specification, chemical structures and physical properties, etc., of the compounds of Examples and Reference examples are shown.

In Tables, MS.APCI (m/z) indicate mass spectrometric data (atmospheric pressure chemical ionization mass spectrum).

Moreover, in the abbreviations in the present specification are as follows;
"Me" represents methyl group,
"Et" represents ethyl group, and
"Bu" represents butyl group, respectively.

Experimental Example 1

CaSR Activating Effect

In Vitro Test Using CaSR Expressing Cells

CaSR is a member of G protein-coupled receptor (GPCR). When CaSR of cells are activated by stimulating with extracellular $Ca^{2+}$ ion or an agonist (a compound having CaSR activating effect), etc., phospholipase C (PLC) is activated through G protein (Gq), and an intracellular calcium concentration is increased.

Thus, an activating effect on CaSR was examined by using CaSR expressing cell line and referring to change in an intracellular calcium concentration as an index. Preparation of cell strains and a test using the same are, more specifically, carried out as mentioned in the following (1) and (2).

(1) Acquisition of Human CaSR Expressing Cell Line cDNA fragment encoding human CaSR was obtained from human kidney derived cDNA library by PCR.

[Primer to be used for PCR was designed based on known nucleic acid sequence information on human CaSR (GenBank/EMBL accession no. D50855; GenBank/EMBL accession no. NM000388;

Aida et al., Biochem. Biophys. Res. Commun., 214:524-529, 1995;

Garrett et al., J. Biol. Chem., 270: 12919-12925, 1995, etc.).

Also, the full length cDNA encoding CaSR was obtained first as three divisional parts.]

These cDNA fragments were adequately connected to an expression vector to obtain a plasmid for expressing a functional human CaSR in animal cells.

Also, this human CaSR expression plasmid was transfected to CHO cells with a Gα16 expression plasmid [a plasmid which is to express α subunit (α16) of G protein], and selected from a medium containing neomycin (G418) to obtain stable expressing cell line.

The obtained cell line stably expressed CaSR of human and α16 subunit of G protein.

(2) Measurement of Calcium Concentration in Cells

By using the CaSR expressing cell line obtained in the above-mentioned (1), change in an intracellular calcium concentration was measured at the time when the cells were stimulated in the presence or in the absence of a test compound as follows.

First, cells were collected using a cell scraper, suspended in a solution comprising Hepes buffer [10 mM Hepes (7.3), 10 mM glucose, 140 mM NaCl, 5 mM KCl, 2 mM $CaCl_2$, 1 mM $MgCl_2$] to which 0.1% cremophor and 3 µM Fura-2 had been added, and reacted at 37° C. for 1 hour under the conditions wherein a test compound of various concentrations (or conditions not added).

After being washed, the cells suspended in Hepes buffer were seeded to a plate (about $2\times10^5$ cells per 1 well of 96-well plate), and fluorescent intensity (Ratio of 340/380 nm) was measured using FDSS (Functional Drug Screening System; Hamamatsu Photonics K.K.) to examine change in intracellular calcium concentrations.

CaSR activating effect was confirmed basing on the value (change in an intracellular calcium concentration) measured in the reaction carried out in the presence of the test compound, a CaSR activating ability was confirmed.

Also, from the measured values (change in an intracellular calcium concentration) of the test compound with various concentrations, a concentration/response curve was drawn to obtain an EC50 value (concentration of agonist giving a half maximal response).

Experimental Example 2

Suppressing Effect on PTH Production

In Vitro Test Using Rat Parathyroid Cells

By using primary cultured cells prepared from the parathyroid in rats, suppressing effect on PTH production was examined according to the following in vitro test.

(1) Preparation and Culture of Rat Parathyroid Cells:

Thirty-six 10-weeks old male CD (SD) IGS rats (Crj series, grade: SPF, CHARLES RIVER LABORATORIES JAPAN, INC.) were euthanasically sacrificed under ether anesthesia, the thyroid gland together with the parathyroid glands were cut out under sterilized conditions, and preserved in ITS-containing DMEM/F-12 medium (low Ca). The parathyroid glands were separated from the obtained material under observation by stereoscopic microscope, and collected in the same medium. Next, the medium was discarded, the parathyroid glands were washed with a phosphate buffer solution (PBS(−)) containing no calcium and magnesium ions, 5 ml of a collagenase solution [PBS(−) containing 1.5 mg/ml of collagenase type IV (Gibco Co., catalogue No. 17104-019)] was added, and digested at 37° C. for 1 hour with shaking. After digestion, the enzyme solution was discarded, the parathyroid glands were quickly minced with a scalpel in a laboratory dish, and were collected in 7 ml of a collagenase solution, and digested again at 37° C. for 90 minutes with shaking.

Cell debris was removed using cell strainer, the residue was removed, and then, the cells were collected. They were washed twice with an ITS-containing DMEM/F-12 medium (low Ca) containing 5% FCS, and suspended in the same medium. The parathyroid cells were suspended at the concentration of about $5 \times 10^4$ cells/ml, and were seeded to 96-well plate (200 μl/well), and cultured (pre-culture) at 37° C. for about 24 hours in a $CO_2$ incubator.

The ITS-containing DMEM/F-12 medium (low Ca) to be used mentioned above was prepared as follows. Ca-free DMEM (Dulbecco's modified Eagle's medium) (Gibco Co., catalogue No. 21068-028)(500 ml), F-12 (F-12 nutrient mixture; Gibco Co., catalogue No. 11765-054)(500 ml) and 10 ml of ITS (a mixture containing 5 μg/ml of insulin, 5 μg/ml of transferrin and 5 ng/ml of selenium) (ITS+Premix; BD Biosciences Co., catalogue No. 35435) were mixed. To the mixture was dissolved 3.5745 g of HEPES (NACALAI TESQUE Co., catalogue No. 17547-95), and 10 ml of 200 mM L-glutamine (Gibco Co., catalogue No. 25030-081) and 1 ml of Penicillin-Streptomycin solution (100× Penicillin-Streptomycin, liquid; Gibco Co., catalogue No. 15140-122) were added, and the resulting mixture was sterilized by filtration, and then, used. Ca concentration in the medium is about 0.15 mM.

(2) Test of Suppressing Effect on PTH Production

Rat parathyroid cells were pre-cultured as mentioned in the above (1), then, the medium was changed, and the cells were cultured for 22 to 24 hours in a medium to which a test compound and $CaCl_2$ had been added (96-well plate, 200 μl/well). Various concentrations of the test compound and $CaCl_2$ were added to a serum-free ITS-containing DMEM/F-12 medium (low Ca), and the resulting medium was used. When the test compound is to be added, $CaCl_2$ was added so that the Ca concentration became 1.15 mM. After culture, culture supernatant was collected, cells, etc. were removed therefrom by centrifugation, and was preserved at −80° C.

PTH (1-84) in the above-mentioned culture supernatant was measured by the ELISA Method, and determined as a PTH production value. Measurement of PTH (1-84) was carried out by using a kit (Rat Intact PTH ELISA kit; Immutopics Co., catalogue No. 60-2500).

Based on the measured value (PTH production value), of the test compounds, the inhibition rate in PTH production was calculated. In the calculation, for the convenience sake, a PTH production value (A) in culture with 1.15 mM $CaCl_2$-containing medium (no test compound added) was set as a maximum production value, and a PTH production value (B) in culture with 2.15 mM $CaCl_2$-containing medium (no test compound added) was set as a minimum production, and inhibition rate was calculated from the following formula.

Inhibition rate in *PTH* production (%)={(*A*)−(*PTH* production value in the presence of 1.15 mM $CaCl_2$ and the test compound with various concentrations)}/{(*A*)−(*B*)}×100

(when PTH production value obtained in the presence of the test compound is the same as the maximum production level, then the inhibition rate is 0%, and when it is the same as the minimum production level, then the inhibition rate is 100%.)

$IC_{50}$ value was measured from the PTH production-suppressing ratio in the presence of the test compound with various kinds of concentrations.

$IC_{50}$ value was calculated by using a software for plotting a concentration/response curve (Graphpad PRISM 3.0; Graphpad Software Co.).

Experimental Example 3

Effect (I) on PTH Level in Blood

In Vivo Test Using Rat Adenine Model

As an animal model of hyperparathyroidism, rat adenine model was used, and an effect on a PTH level in blood (lowering effect on PTH in blood) was examined according to the following in vivo test.

Male CD (SD) IGS rats (10-weeks old or so) (Crj, grade: SPF, CHARLES RIVER LABORATORIES JAPAN, INC.) were used.

After acclimation for 7 days, during which rats were fed with standard diet (CRF1), rats were provided with adenine diet (0.75% adenine-containing high phosphorus-low calcium diet (Ca: 0.5%, Pi: 1.2%); supplied by Oriental Bioservice Inc.), and bred for 2 weeks. After 2 weeks, heparin-treated blood (250 μl) was collected from the respective rats under ether anesthesia. Blood was collected from jugular vein using 25G (0.50×25 mm)-needle-tipped syringe, and after collection of the blood, and then, subjected to astriction. Collected blood was centrifuged at 12000 rpm for 3 minutes, and then, supernatant was collected as a plasma sample.

PTH (PTH (1-84)) in the plasma was measured by ELISA. PTH (1-84) was measured in the same manner as in item (2) of the above-mentioned Experimental example 2.

Based on the results, rats in which a PTH concentration in blood was sufficiently raised were selected, and divided into groups such that average PTH concentration of each animal groups do not vary, and subjected to the test.

On the next day, blood (400 μl) was collected prior to the administration of the test compound, and then, the test compound was orally administered. After 1, 4 and 24 hours following administration, 400 μl of blood at each time point was collected, and plasma obtained by centrifugation was preserved at −80° C. (or −20° C.)

PTH in the preserved plasma was measured in the same manner as mentioned above.

According to this procedure, PTH-lowering effect of the test compound was confirmed.

Experimental Example 4

Effect (II) on PTH Level in Blood

In Vivo Test Using Rat Model of ⅚-Nephrectomy

Rat model of ⅚-nephrectomy was used as an animal model of hyperparathyroidism. An effect on PTH level in blood (lowering effect on PTH in blood) was examined by the following in vivo test.

First, ⅚-nephrectomy was prepared as follows.

Male CD (SD) IGS rats (10-weeks old or so) (Crj, grade: SPF, CHARLES RIVER LABORATORIES JAPAN, INC.) were used.

A part (⅔) of rat's left kidney was removed, and one week after, the right kidney was removed.

After one week following the removal of the right kidney, rats were provided with high phosphrus-low calcium diet (Ca: 0.5%, Pi: 1.2%). One week after the initiation of providing the high phosphrus-low calcium diet, blood was collected from jugular vein to prepare a blood plasma sample. Body weight, and PTH, Ca, P and BUN concentrations in blood were measured, and the rats were divided into groups based on the results obtained.

Test compound was orally administered once a day to the animals prepared as mentioned above for two weeks, and blood was collected twice a week immediately before administration of the test compound. PTH, Ca, P and BUN concentrations in blood samples were measured.

According to this procedure, PTH-lowering effect of the test compound was confirmed.

Experimental Example 5

Pharmacological Effect of the Compounds of the Present Invention

With respect to the compound of the present invention, in the same manner as in the above-mentioned Experimental examples 2 and 3, the results of measurement of the activating effect on CaSR and the suppressing effect on PTH production were show in the following table.

Activity Table

| Comound Example No. | Activating effect on CaSR ($EC_{50}$ (μM)) | Suppressing effect on PTH production ($IC_{50}$ (nM)) |
| --- | --- | --- |
| 1.077 | 0.42 | 5.3 |
| 3.001 | 0.29 | 8 |
| 5.023 | 0.42 | <10 |
| 12.020 | 0.018 | 0.27 |
| 12.028 | 0.017 | 0.47 |

Also, with regard to these compounds, in vivo test using rat adenine model was carried out in the same manner as in the above-mentioned Experimental example 4, and as a result, these compounds showed an lowering effect on PTH level in blood, in oral administration, as compared with the control group in which no test compound to be tested was administered.

Example 1.001

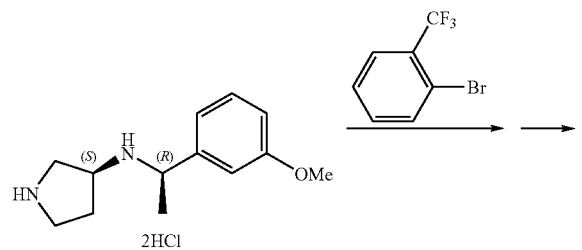

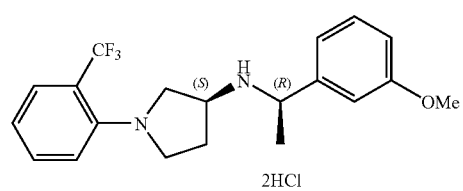

(1) To a suspension of 146.6 mg of (S)-3-[(R)-1-(3-methoxyphenyl)ethylamino]pyrrolidine dihydrochloride, 112.5 mg of 1-bromo-2-trifluoromethylbenzene, 22.5 mg of palladium acetate, and 62.3 mg of BINAP (2,2'-bis(di-phenylphosphino-1,1'-binaphthyl)) in 5 ml of toluene was added 336 mg of sodium tert-butoxide, and the mixture was stirred at 80° C. for 16 hours. To the reaction mixture was added a saturated sodium bicarbonate solution, the mixture was stirred and then the liquids were separated. The organic layer was dried and concentrated, and the residue was purified by NH silica gel column chromatography (hexane:ethyl acetate=97:3→80:20) to obtain 78.9 mg of (R)-1-(3-methoxyphenyl)ethyl-[(S)-1-(2-trifluoromethylphenyl)pyrrolidin-3-yl]amine.

(2) In 10 ml of chloroform was dissolved 78.9 mg of (R)-1-(3-methoxyphenyl)ethyl-[(S)-1-(2-trifluoromethylphenyl)-pyrrolidin-3-yl]amine, and 1 ml solution of 4M hydrochloric acid in a dioxane was added to the mixture and the resulting mixture was stirred. The reaction mixture was evaporated, and diethyl ether was added to the residue, and the precipitates were collected by filtration and washed with diethyl ether to obtain 66.7 mg of (R)-1-(3-methoxyphenyl)ethyl-[(S)-1-(2-trifluoromethylphenyl)pyrrolidin-3-yl]amine dihydrochloride (the following Table A1, Example 1.001).

Examples 1.002 to 1.081

In the same manner as in the above-mentioned Example 1.001, compounds of Example 1.002 to 1.081 in the following Table A1 were obtained.

Example 1.082

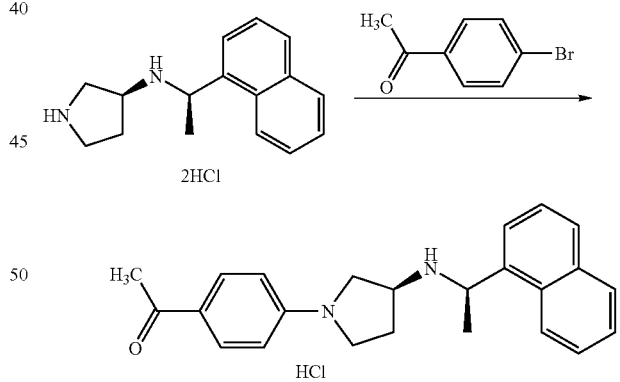

(1) In 2 ml of toluene were suspended 200 mg of (S)-3-[(R)-1-(naphthalen-1-yl)ethylamino]pyrrolidine dihydrochloride, 127 mg of 4-bromoacetophenone, 214 mg of sodium tert-butoxide, and 76 mg of biphenyl-2-yl-di-tert-butylphosphane, and nitrogen gas was ventilated for 15 minutes. After adding 59 mg of tris(dibenzylideneacetone) dipalladium to the mixture, the reaction vessel was sealed and the mixture was stirred at room temperature for 3 days. The reaction mixture was diluted with ethyl acetate, and washed with a saturated aqueous sodium bicarbonate solution. The organic layer was separated and concentrated, and the obtained residue was purified by silica gel column chromatography to obtain (S)-1-(4-acetylphenyl)pyrrolidin-3-yl-[(R)-1-(naphthalen-1-yl)ethyl]amine.

(2) In 2 ml of tetrahydrofuran was dissolved (S)-1-(4-acetylphenyl)pyrrolidin-3-yl-[(R)-1-(naphthalen-1-yl)-ethyl]amine obtained in the above-mentioned (1), and 0.2 ml of a solution of 4M hydrochloric acid-dioxane was added to the mixture. The precipitated solids were collected by filtration, washed with ether and dried to obtain 90 mg of (S)-1-(4-acetylphenyl)pyrrolidin-3-yl-[(R)-1-(naphthalen-1-yl)ethyl]amine hydrochloride (the following Table A1, Example 1.082).

Example 1.083

In the same manner as in the above-mentioned Example 1.082, the compound of Example 1.083 in the following Table A1 was obtained.

Example 2.001

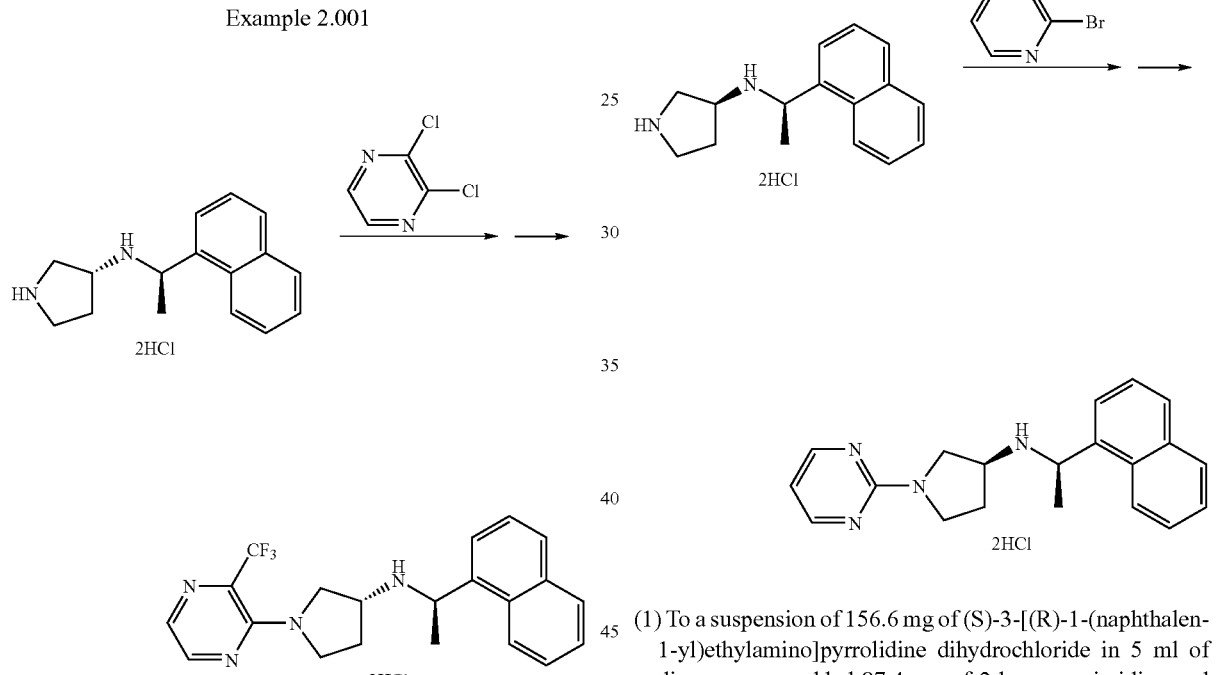

(1) To a solution of 162 mg of (R)-3-[(R)-1-(naphthalen-1-yl)ethylamino]pyrrolidine dihydrochloride and 79.0 mg of 2,3-dichloro-pyrazine in 5 ml of ethanol was added 345 mg of potassium carbonate, and the mixture was stirred under reflux for 16 hours. The reaction mixture was filtered, and the solvent was evaporated, and to the residue was added a saturated aqueous sodium bicarbonate solution and chloroform, and the liquids were separated. The organic layer was dried, and the solvent was evaporated, then, the residue was purified by NH silica gel column chromatography (hexane:ethyl acetate=97:3→80:20) and by silica gel chromatography (hexane:ethyl acetate=90:10→0:100) to obtain 64.0 mg of (R)-1-(3-chloropyrazin-2-yl)pyrrolidin-3-yl-[(R)-1-(naphthalen-1-yl)ethyl]amine.

(2) In 2 ml of chloroform was dissolved 64.0 mg of (R)-1-(3-chloropyrazin-2-yl)pyrrolidin-3-yl-[(R)-1-(naphthalen-1-yl)ethyl]amine, and 3 ml of a solution of 4M hydrochloric acid in dioxane was added to the mixture, and the resulting mixture was stirred. After the reaction mixture was concentrated under reduced pressure, diethyl ether was added to the residue, and the precipitates were collected by filtration, washed with diethyl ether, and dried to obtain 63.9 mg of (R)-1-(3-chloropyrazin-2-yl)pyrrolidin-3-yl-[(R)-1-(naphthalen-1-yl)ethyl]amine dihydrochloride (the following Table A2, Example 2.001).

Examples 2.002 to 2.009

In the same manner as in the above-mentioned Example 2.001, the compounds of Example 2.002 to 2.009 in the following Table A2 were obtained.

Example 2.010

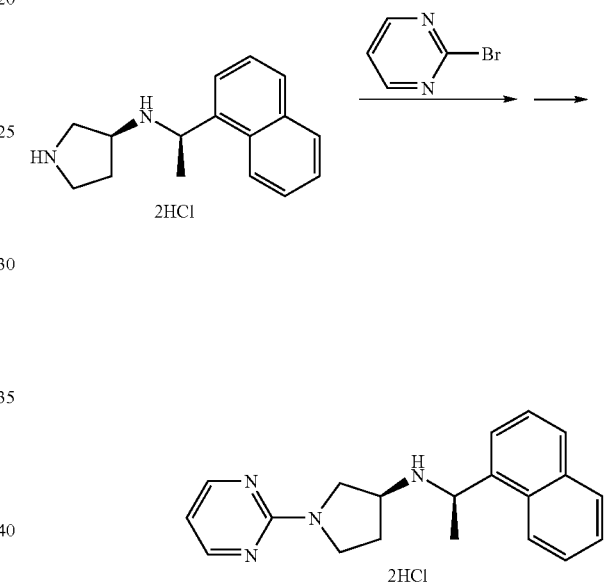

(1) To a suspension of 156.6 mg of (S)-3-[(R)-1-(naphthalen-1-yl)ethylamino]pyrrolidine dihydrochloride in 5 ml of dioxane were added 87.4 mg of 2-bromopyrimidine and 207 mg of diisopropylethylamine, and the mixture was stirred under reflux for 16 hours. The reaction mixture was evaporated, and to the residue were added a saturated aqueous sodium bicarbonate solution and chloroform, the mixture was stirred and the liquids were separated. The organic layer was dried, the solvent was evaporated, and the residue was purified by silica gel column chromatography (hexane:ethyl acetate=1:2→0:1) to obtain 112 mg of (R)-1-(naphthalen-1-yl)ethyl-[(S)-1-(pyrimidin-2-yl)-pyrrolidin-3-yl]amine.

(2) In 10 ml of ethyl acetate was dissolved 112 mg of (R)-1-(naphthalen-1-yl)ethyl-[(S)-1-(pyrimidin-2-yl)pyrrolidin-3-yl]amine, and 1 ml of a solution of 4M hydrochloric acid in ethyl acetate was added to the mixture and the resulting mixture was stirred. The reaction mixture was concentrated under reduced pressure, to the residue was added diethyl ether, precipitates were collected by filtration and washed with ethyl acetate, to obtain 68.3 mg of (R)-1-

(naphthalen-1-yl)ethyl-[(S)-1-(pyrimidin-2-yl)pyrrolidin-3-yl]amine dihydrochloride (the following Table A2, Example 2.010).

Examples 2.011 to 2.018

In the same manner as in the above-mentioned Example 2.010, the compounds of Example 2.011 to 2.018 in the following Table A2 were obtained.

Example 3.001

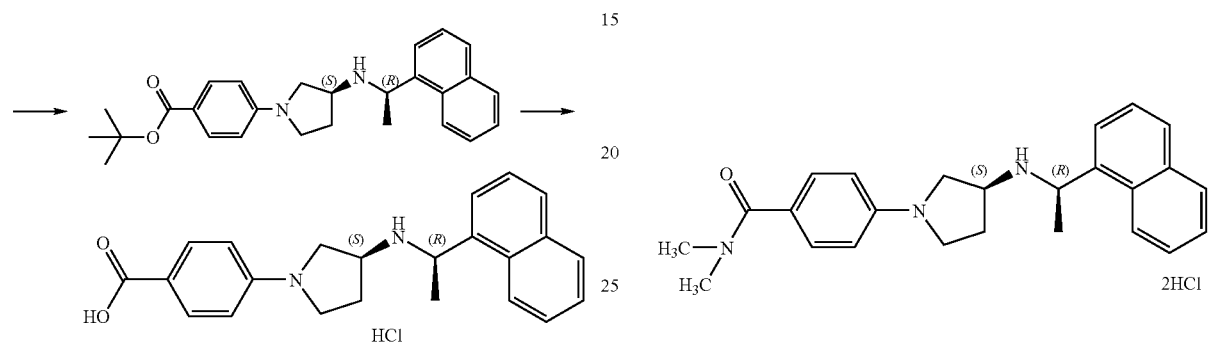

(1) In the same manner as in the above-mentioned Example 1.001, tert-butyl 4-[(S)-3-[(R)-1-(naphthalen-1-yl)ethylamino]pyrrolidin-1-yl]benzoate (the compound of Example 1.020 in the following Table A2) was obtained.

(2) To a solution of 103 mg of tert-butyl 4-[(S)-3-[(R)-1-(naphthalen-1-yl)ethylamino]pyrrolidin-1-yl]benzoate in 5 ml of a chloroform was added 20 ml of trifluoroacetic acid, and the mixture was stirred under room temperature for 16 hours. The reaction mixture was concentrated, toluene was added to the residue and the mixture was evaporated again. The residue was dissolved in 10 ml of chloroform, 20 ml of a solution of 4M hydrochloric acid in dioxane was added and the mixture was stirred. The reaction mixture was concentrated under reduced pressure, diethyl ether was added to the residue, and after collecting the precipitates by filtration, it was washed with diethyl ether and dried to obtain 89.2 mg of 4-[(S)-3-[(R)-1-(naphthalen-1-yl)ethylamino]pyrrolidin-1-yl]benzoic acid hydrochloride (Example 3.001 in the following Table A3).

Examples 3.002 to 3.011

In the same manner as in the above-mentioned Example 3.001, the compounds of Example 3.002 to 3.011 in the following Table A3 were obtained.

Example 3.012

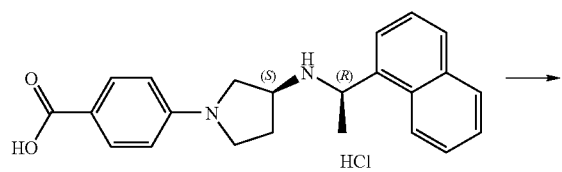

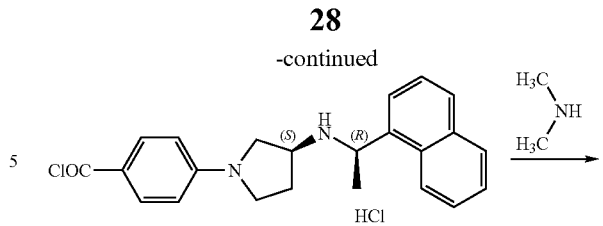

(1) To a solution of 50 mg of 4-[(S)-3-[(R)-(naphthalen-1-yl)ethylamino]pyrrolidin-1-yl]benzoic acid hydrochloride (the compound obtained in Example 3.001) in 5 ml of methylene chloride (MeOH free) was added dropwise 43 μl of oxalyl chloride, and then, several drops of dimethylformamide were added to the mixture, and the resulting mixture was stirred under room temperature for 16 hours. The solvent was removed from the reaction mixture to obtain the residue.

(2) To the compound obtained as mentioned above were added dimethylamine (82 μl of 2M THF solution) and 10 ml of methylene chloride to dissolve them, 70.2 μl of triethylamine was added to the mixture, and the mixture was stirred under room temperature for 16 hours. To the reaction mixture were added a saturated aqueous sodium bicarbonate solution and chloroform, the mixture was stirred and the liquids were separated. The organic layer was dried and concentrated, and the residue was purified by NH silica gel column chromatography (hexane:ethyl acetate 7:1→0:1) to obtain 22.4 mg of N,N-dimethyl-4-[(S)-3-[(R)-1-(naphthalen-1-yl)ethylamino]pyrrolidin-1-yl]benzamide.

(3) To a solution of 22.4 mg of N,N-dimethyl-4-[(S)-3-[(R)-1-(naphthalen-1-yl)ethylamino]pyrrolidin-1-yl]-benzamide dissolved in 1 ml of methylene chloride was added dropwise 3 ml of a solution of 4M hydrochloric acid in dioxane, and the mixture was stirred for a while. The reaction mixture was concentrated, t-butanol was added to the residue to dissolve the same, and freeze-dried to obtain 22.9 mg of N,N-dimethyl-4-[(S)-3-[(R)-1-(naphthalen-1-yl)ethylamino]-pyrrolidin-1-yl]benzamide hydrochloride (Example 3.012 in the following Table A3).

Examples 3.013 to 3.016

In the same manner as in the above-mentioned Example 3.012, the compounds of Example 3.013 to 3.016 in the following Table A3 were obtained.

Example 3.017

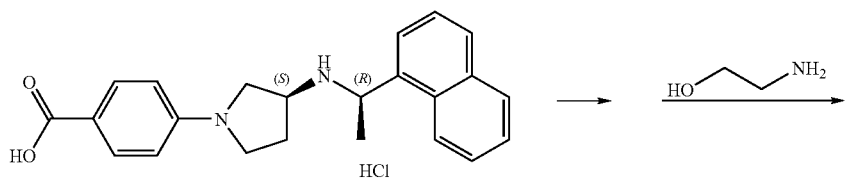

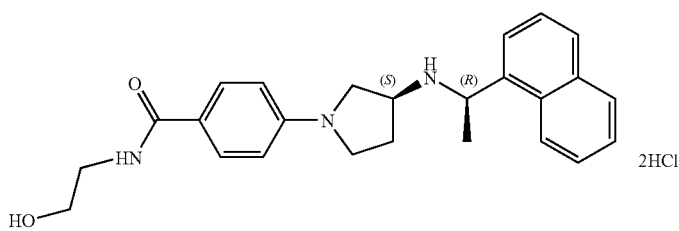

(1) To a mixed solution of 7.7 mg of 2-aminoethanol and 50 mg of 4-[(S)-3-[(R)-1-(naphthalen-1-yl)ethylamino]pyrrolidin-1-yl]benzoic acid hydrochloride (the compound obtained in Example 3.001) dissolved in 8 ml of dimethylformamide were added 22.2 mg of 1-hydroxybenzotriazole, 70 μl of triethylamine and 31.4 mg of EDC hydrochloride, and the mixture was stirred at room temperature for 16 hours. The reaction mixture was evaporated, a saturated aqueous sodium bicarbonate solution and chloroform were added to the residue, and the mixture was stirred and the liquids were separated. The organic layer was dried and concentrated, and the residue was purified by NH thin layer silica gel chromatography (chloroform:methanol=39:1) and thin layer silica gel chromatography (chloroform:methanol=9:1) to give 22.6 mg of N-(2-hydroxyethyl)-4-[(S)-3-[(R)-1-(naphthalen-1-yl)ethylamino]pyrrolidin-1-yl]benzamide.

(2) To a solution of 22.6 mg of N-(2-hydroxyethyl)-4-[(S)-3-[(R)-1-(naphthalen-1-yl)ethylamino]pyrrolidin-1-yl]-benzamide dissolved in 1 ml of methylene chloride was added dropwise 3 ml of a solution of 4M hydrochloric acid in dioxane, and the mixture was stirred for a while. The reaction mixture was evaporated, and, to the residue was added tert-butanol to dissolve the same, and freeze-dried to obtain 25.6 mg of N-(2-hydroxyethyl)-4-[(S)-3-[(R)-1-(naphthalen-1-yl)ethylamino]pyrrolidin-1-yl]benzamide hydrochloride (the following Table A3, Example 3.017).

Example 3.018

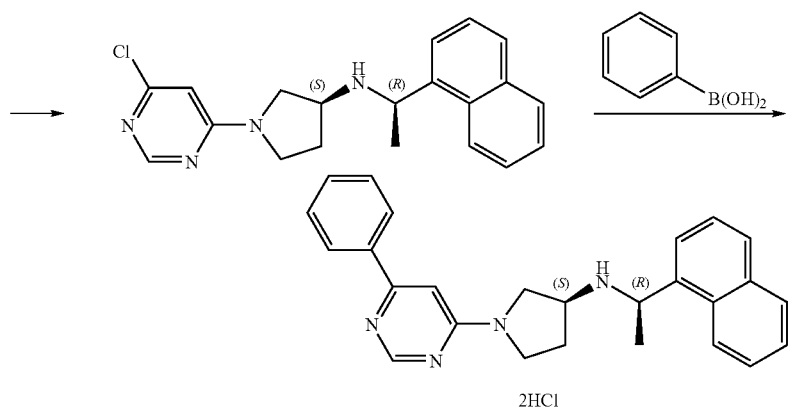

(1) In the same manner as in the above-mentioned Example 2.016, 1-[(S)-(6-chloropyrimidin-4-yl)pyrrolidin-3-yl]-(R)-1-(naphthalen-1-yl)ethylamine (a free form of the compound of Example 2.012 in the following Table) was obtained.

(2) In 2 ml of toluene were suspended 100 mg of 1-[(S)-(6-chloropyrimidin-4-yl)pyrrolidin-3-yl]-(R)-1-(naphthalen-1-yl)ethylamine, 52 mg of phenyl boronic acid and 78 mg of potassium carbonate, and a nitrogen gas was ventilated for 5 minutes. After adding 32 mg of tetrakistriphenylphosphine palladium to the mixture, the reaction mixture was stirred under nitrogen flow at 100° C. overnight. After standing to cool to room temperature, ethyl acetate and a saturated aqueous sodium bicarbonate solution were added to the reaction mixture, and the liquids were separated. The organic layer was dried, the solvent was evaporated and the obtained residue was purified by silica gel column chromatography (hexane-ethyl acetate) to obtain 46 mg of (R)-1-(naphthalen-1-yl)ethyl-[(S)-1-(6-phenylpyrimidin-4-yl)pyrrolidin-3-yl]amine.

(3) In 1 ml of tetrahydrofuran was dissolved 46 mg of (R)-1-(naphthalen-1-yl)ethyl-[(S)-1-(6-phenylpyrimidin-4-yl)-pyrrolidin-3-yl]amine, 0.2 ml of a solution of 4M hydrochloric acid-dioxane was added, and the mixture was allowed to stand at room temperature. The precipitated solids were collected by filtration, washed with ether, and dried to obtain 41 mg of (R)-1-(naphthalen-1-yl)ethyl-[(S)-1-(6-phenylpyrimidin-4-yl)pyrrolidin-3-yl]amine dihydrochloride (Example 3.018 in the following Table A3).

Examples 3.019 to 3.022

In the same manner as in the above-mentioned Example 3.018, the compounds of Examples 3.019 to 3.022 in the following Table A3 were obtained.

Example 4.001

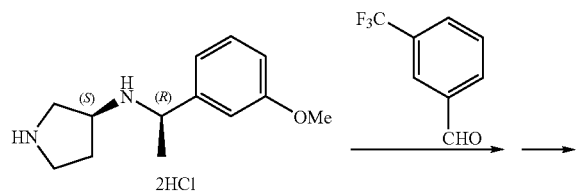

(1) To a suspension of 176 mg of (S)-3-[(R)-1-(3-methoxyphenyl)ethylamino]pyrrolidine dihydrochloride, 110 mg of (3-trifluoromethyl)benzaldehyde and 636 mg of sodium triacetoxyborohydride in 10 ml of methylene chloride was added several drops of acetic acid, and the mixture was stirred at room temperature for 16 hours. To the reaction mixture were added a saturated aqueous sodium bicarbonate solution and chloroform, the mixture was stirred and the liquids were separated. The organic layer was dried, the solvent was removed, and then, the residue was purified by NH silica gel column chromatography (hexane:ethyl acetate=10:1) to obtain 91.2 mg of (R)-1-(3-methoxyphenyl)ethyl-[(S)-1-(3-trifluoromethylbenzyl)pyrrolidin-3-yl]amine.

(2) In 10 ml of ethyl acetate was dissolved 91.2 mg of (R)-1-(3-methoxyphenyl)ethyl-[(S)-1-(3-trifluoromethylbenzyl)-pyrrolidin-3-yl]amine, and 1 ml of a solution of 4M hydrochloric acid in ethyl acetate was added, and the mixture was stirred. The reaction mixture was evaporated, diethyl ether was added to the residue, and after collecting the precipitates by filtration, it was washed with diethyl ether and dried to obtain 70.4 mg of (R)-1-(3-methoxyphenyl)ethyl-[(S)-1-(3-trifluoromethylbenzyl)-pyrrolidin-3-yl]amine dihydrochloride (Example 4.001 in the following Table B).

Examples 4.002 to 4.038

In the same manner as in the above-mentioned Example 4.001, the compounds of Examples 4.002 to 4.038 in the following Table B were obtained.

Example 5.001

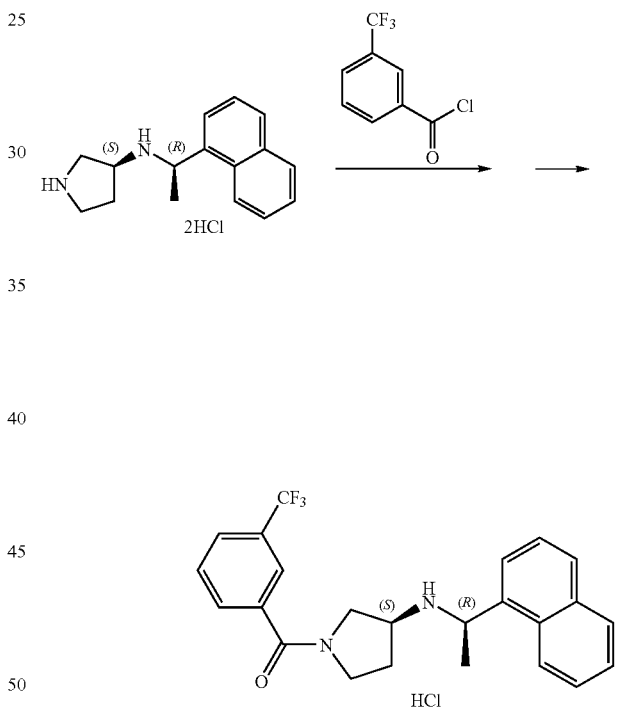

(1) After cooling a suspension of 156.6 mg of (S)-3-[(R)-1-(naphthalen-1-yl)ethylamino]pyrrolidine dihydrochloride in 5 ml of methylene chloride to 0° C., 208.6 mg of (3-trifluoromethyl)benzoyl chloride and 210 μl of triethylamine were added to the suspension, and the reaction mixture was stirred at room temperature for 1 hour. To the reaction mixture were added a saturated aqueous sodium bicarbonate solution and chloroform, the mixture was stirred and the liquids were separated. The organic layer was dried and concentrated, and the residue was purified by silica gel column chromatography (hexane:ethyl acetate=2:1→0:1) to obtain 210 mg of (S)-3-[(R)-1-(naphthalen-1-yl)ethylamino]-1-(3-trifluoromethyl)benzoylpyrrolidine.
MS.APCI (m/z): 413 [M+H]+

(2) In 10 ml of chloroform was dissolved 210 mg of (S)-3-[(R)-1-(naphthalen-1-yl)ethylamino]-1-(3-trifluoromethyl)-benzoylpyrrolidine, 1 ml of a solution of 4M hydrochloric acid in dioxane was added to the solution and the mixture was stirred. The reaction mixture was concentrated under reduced pressure, diethyl ether was added to the residue, and after collecting the precipitates by filtration, it was washed with diethyl ether and dried to obtain 187.1 mg of (S)-3-[(R)-1-(naphthalen-1-yl)ethylamino]-1-(3-trifluoromethyl)benzoylpyrrolidine hydrochloride (Example 5.001 in the following Table C).

Examples 5.002 to 5.016

In the same manner as in the above-mentioned Example 5.001, the compounds of Examples 5.002 to 5.016 in the following Table C were obtained.

Example 5.017

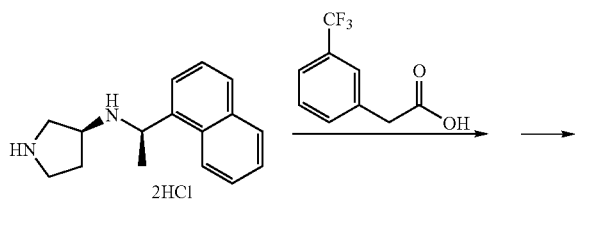

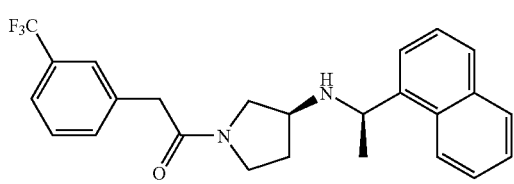

To solution of 125.3 mg of (S)-3-[(R)-1-(naphthalen-1-yl)ethylamino]pyrrolidine dihydrochloride in 5 ml of DMF were added 81.6 mg of (3-trifluoromethyl)phenylacetic acid, 84.3 mg of 1-[3-(dimethylaminopropyl)]-3-ethylcarbodiimide hydrochloride, 67.3 mg of 1-hydroxybenzotriazole, and 153 μl of triethylamine, and the reaction mixture was stirred at room temperature for 16 hours. To the reaction mixture were added a saturated aqueous sodium bicarbonate solution and ethyl acetate, the mixture was stirred and the liquids were separated. The organic layer was washed with water and then dried, the solvent was evaporated, and the residue was purified by thin layer silica gel chromatography (chloroform:methanol=19:1) to obtain 145.7 mg of (S)-3-[(R)-(naphthalen-1-yl)ethylamino]-1-(3-trifluoromethyl)-phenylacetylpyrrolidine (Example 5.017 in the following Table C).

Examples 5.018 to 5.056

In the same manner as in the above-mentioned Example 5.017, the compounds of Example 5.018 to 5.056 in the following Table C were obtained.

Example 6.001

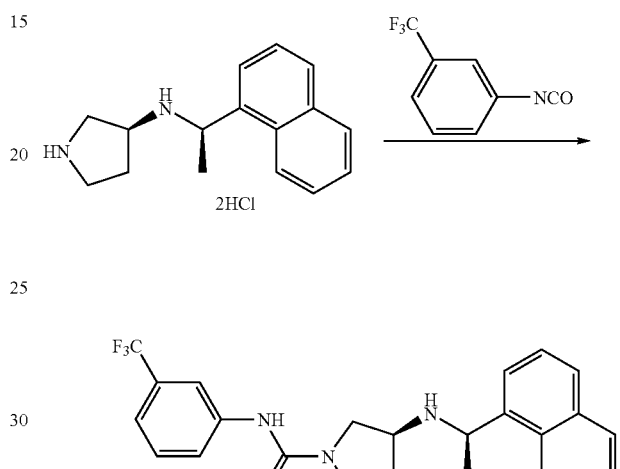

To a suspension of 94 mg of (S)-3-[(R)-1-(naphthalen-1-yl)ethylamino]pyrrolidine dihydrochloride in 5 ml of methylene chloride were added 56 mg of (3-trifluoromethyl)phenylisocyanate and 140 μl of triethylamine, the reaction mixture was stirred at room temperature for 16 hours. To the reaction mixture were added a saturated aqueous sodium bicarbonate solution and chloroform, the mixture was stirred and the liquids were separated. The organic layer was dried, the solvent was evaporated, and then, the residue was purified by thin layer silica gel chromatography (chloroform:methanol=19:1) to obtain 125.2 mg of (S)-3-[(R)-1-(naphthalen-1-yl)ethylamino]pyrrolidin-1-carboxylic acid (3-trifluoromethyl)phenylamide (Example 6.001 in the following Table).

Example 6.002

In the same manner as in the above-mentioned Example 6.001, the compounds of Example 6.002 in the following Table C were obtained.

Example 7.001

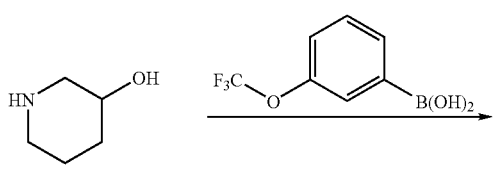

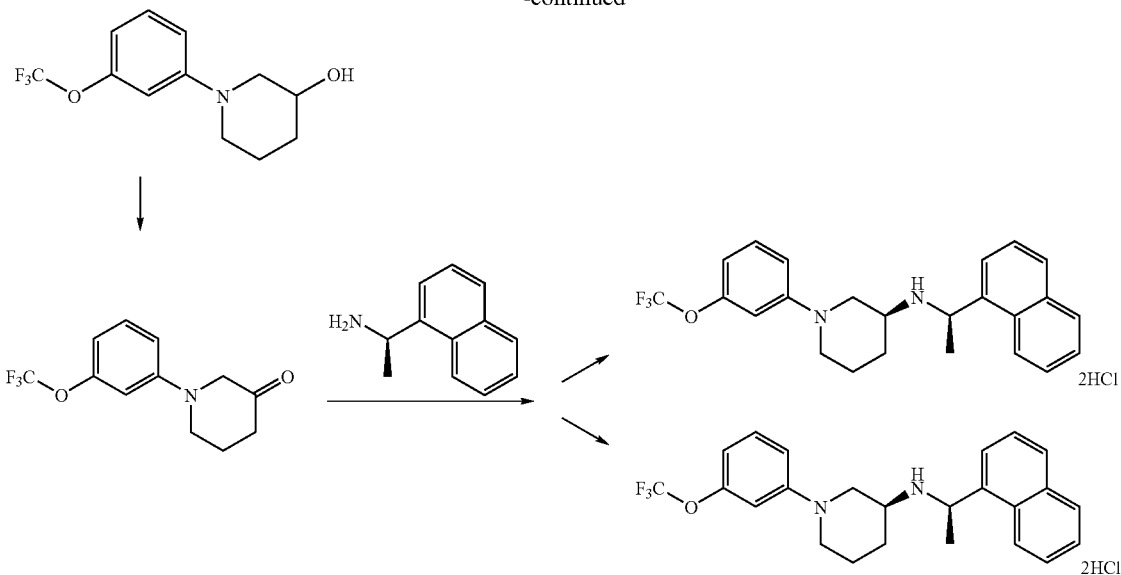

(1) To a solution of 3.03 g of 3-hydroxypiperidine and 12.4 g of 3-(trifluoromethoxy)phenyl boronic acid dissolved in 150 ml of methylene chloride were added 5.45 g of copper acetate hydrate, 7 ml of triethylamine and 15 g of Molecular Sieve 4A (powder), and the mixture was stirred at room temperature for 3 days. After the reaction mixture was filtered, a saturated aqueous sodium bicarbonate solution and chloroform were added to the mixture and the mixture was stirred, then, insoluble materials were again filtered off. The filtrate was separated, the organic layer was dried and concentrated, and the residue was purified by NH silica gel column chromatography (hexane:ethyl acetate=10:1→2:1) to obtain 526 mg of 1-(3-trifluoromethoxyphenyl)piperidin-3-ol. MS.APCI (m/z): 262 [M+H]+

(2) 50 ml of a solution of 351 μl of oxalyl chloride in methylene chloride was cooled to −60° C., 357 μl of DMSO was added dropwise to the solution, and the mixture was stirred at −60° C. for 10 minutes. To the above mixture was added dropwise a solution of 526 mg of 1-(3-trifluoromethoxyphenyl)piperidin-3-ol dissolved in 10 ml of methylene chloride, further 2.05 ml of triethylamine was added dropwise to the above mixture, and then, the resulting mixture was stirred for 16 hours while a temperature thereof was gradually raised to room temperature. To the reaction mixture were added a saturated aqueous sodium bicarbonate solution and chloroform, the mixture was stirred and the liquids were separated. The organic layer was dried and concentrated to obtain 1-(3-trifluoromethoxyphenyl)piperidin-3-one.

(3) To a solution of 158 mg of the compound obtained in the above-mentioned (2) dissolved in 5 ml of methylene chloride was added 85.6 mg of (R)-(+)-1-(1-naphthyl)ethylamine, the mixture was stirred at room temperature for 1 hour, and then, 115 μl of acetic acid and 530 mg of sodium triacetoxy borohydride were added to the mixture, and the mixture was stirred at room temperature for 16 hours. To the reaction mixture were added a saturated aqueous sodium bicarbonate solution and chloroform, the mixture was stirred and the liquids were separated. The organic layer was dried and the solvent was evaporated, then, the residue was purified by thin layer silica gel chromatography (hexane:ethyl acetate=4:1) and thin layer NH silica gel chromatography (hexane:ethyl acetate=10:1→4:1) to obtain (R)-1-(naphthalen-1-yl)ethyl-[(S)-1-(3-trifluoromethoxyphenyl)-piperidin-3-yl]amine and (R)-1-(naphthalen-1-yl)ethyl-[(R)-1-(3-trifluoromethoxyphenyl)piperidin-3-yl]amine, respectively.

(4) (R)-1-(naphthalen-1-yl)ethyl-[(S)-1-(3-trifluoromethoxyphenyl)piperidin-3-yl]amine and (R)-1-(naphthalen-1-yl)ethyl-[(R)-1-(3-trifluoromethoxyphenyl)piperidin-3-yl]-amine obtained in the above-mentioned (3) were each dissolved in 10 ml of ethyl acetate, 1 ml of a solution of 4M hydrochloric acid in ethyl acetate was added thereto and the mixture was stirred. The reaction mixture was concentrated under reduced pressure, diethyl ether was added to the residue, the mixture was washed and dried to obtain 23 mg of (R)-1-(naphthalen-1-yl)ethyl-[(S)-1-(3-trifluoromethoxyphenyl)piperidin-3-yl]amine dihydrochloride (Example 7.001(a) in the following Table EF) and 38 mg of (R)-1-(naphthalen-1-yl)ethyl-[(R)-1-(3-trifluoromethoxyphenyl)piperidin-3-yl]amine dihydrochloride (Example 7.001(b) in the following Table), respectively.

Examples 7.002 to 7.007

In the same manner as in the above-mentioned Example 7.001, the compounds of Examples 7.002 to 7.007 in the following Tables EF were obtained.

Example 8.001

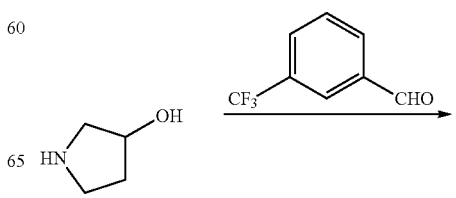

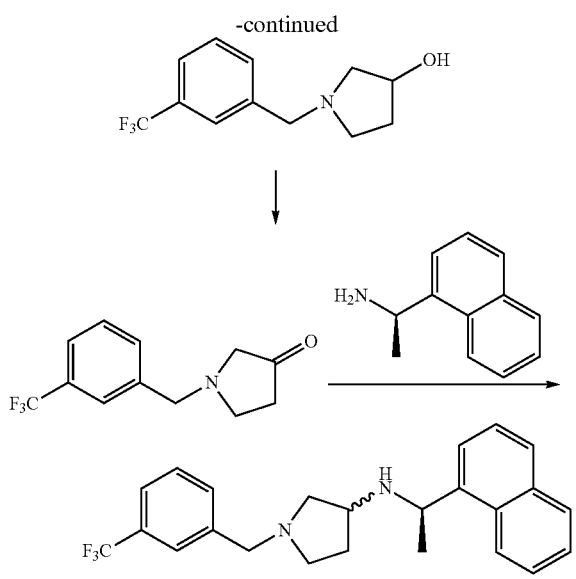

(1) To a solution of 2.61 g of 3-trifluoromethylbenzaldehyde dissolved in 200 ml of methylene chloride was added 1.31 g of 3-pyrrolidinol, the mixture was stirred at room temperature for a while, then 1.3 ml of acetic acid and 4.77 g of sodium triacetoxy borohydride were added to the mixture, and the mixture was stirred at room temperature for 15 hours. To the reaction mixture was added a saturated aqueous sodium bicarbonate solution to make it basic, and chloroform was added to the mixture and the liquids were separated. The organic layer was dried and concentrated to obtain 3.34 g of 1-(3-trifluoromethylbenzyl)pyrrolidin-3-ol. MS.APCI (m/z): 246 [M+H]+

(2) 100 ml of a solution of 2.38 ml of oxalyl chloride in methylene chloride was cooled to −60° C., 2.42 ml of DMSO was added dropwise to the solution, and the mixture was stirred at −60° C. for 10 minutes. To the mixture was added dropwise a solution of 3.34 g of 1-(3-trifluoromethylbenzyl)pyrrolidin-3-ol dissolved in 25 ml of methylene chloride, further 13.9 ml of triethylamine was added dropwise thereto, and the mixture was stirred for 16 hours while the temperature thereof was gradually raised to room temperature. To the reaction mixture were added a saturated aqueous sodium bicarbonate solution and chloroform, the mixture was stirred and the liquids were separated. The organic layer was dried, the solvent was evaporated, and the residue was purified by silica gel column chromatography (hexane:ethyl acetate=5:1→2:1) to obtain 2.82 g of 1-(3-trifluoromethylbenzyl)pyrrolidin-3-one. MS.APCI (m/z): 244 [M+H]+

(3) To a solution of 507 mg of a 1-(3-trifluoromethylbenzyl)pyrrolidin-3-one dissolved in 14 ml of tetrahydrofuran was added 320 mg of (R)-(+)-1-(1-naphthyl)ethylamine, and the mixture was stirred. To the mixed solution was added 800 mg of titanium tetraisopropoxide, the mixture was stirred at room temperature for 15 hours, then, 105 mg of sodium borohydride and 3 ml of methanol were added to the mixture, and the mixture was stirred at room temperature for 3.5 hours. To the reaction mixture was added aqueous ammonia, the mixture was stirred, insoluble materials were filtered off, and the solvent was evaporated. To the residue were added chloroform and water, the mixture was stirred and the liquids were separated. The organic layer was dried and concentrated, and the residue was purified by silica gel column chromatography (chloroform:methanol=50:1→9:1) and NH silica gel column chromatography (ethyl acetate:hexane=1:4) to obtain 443 mg of (R)-1-(naphthalen-1-yl)ethyl-[[1-(3-trifluoromethylbenzyl)pyrrolidine]-3-yl]amine (the following Table EF, Example 8.001). MS.APCI (m/z): 399 [M+H]+

Examples 8.002 to 8.011

In the same manner as in the above-mentioned Example 8.001, the compounds of Examples 8.002 to 8.011 in the following Table EF were obtained.

Examples 9.001 to 9.012

In the same manner as in the above-mentioned Example 5.017, the compounds of Examples 9.001 to 9.012 in the following Table X were obtained.

Examples 9.013 to 9.015

In the same manner as in the above-mentioned Example 5.001, the compounds of Examples 9.013 to 9.015 in the following Table X were obtained.

Examples 10.001 to 10.007

In the same manner as in the above-mentioned Example 1.082, the compounds of Examples 10.001 to 10.007 in the following Table X were obtained.

Examples 11.001 to 11.004

In the same manner as in the above-mentioned Example 3.001, the compounds of Examples 11.001 to 11.004 in the following Table X were obtained.

Examples 11.005 to 11.080

In the same manner as in the above-mentioned Example 3.017, the compounds of Examples 11.005 to 11.080 in the following Table X were obtained.

Example 12.001

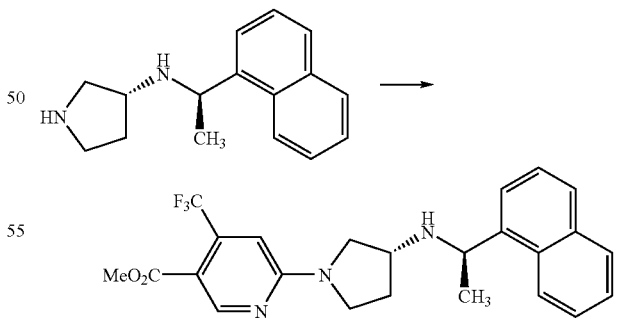

To a solution of 157 mg of (R)-3-[(R)-1-(naphthalen-1-yl)ethylamino]pyrrolidine dihydrochloride and 120 mg of methyl 6-chloro-4-(trifluoromethyl)-nicotinate in 5 ml of dioxane was added 346 mg of potassium carbonate, and the reaction solution was stirred at 100° C. for 1 day. Further, to the reaction mixture was irradiated at 140° C. for 1 hour by using a Microwave reaction system, and then, the reaction mixture was cooled to room temperature. To the mixture were added water and ethyl acetate, and the mixture was stirred and the liquids were separated. The organic layer was dried and concentrated under reduced pressure, and the resulting residue was purified by silica gel column chromatography (hexane:ethyl acetate=80:20→50:50), and then, purified by NH thin layer silica gel column chromatography (hexane:ethyl acetate=67:33) to obtain methyl 6-[(R)-3-[(R)-1-(naphthalen-1-yl)ethylamino]pyrrolidin-1-yl]-4-trifluoromethylnicotinate (the following Table, Example, 12.001).

Example 12.002

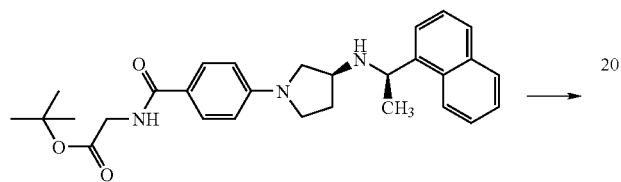

(1) To 74.5 mg of N-4-[(S)-3-[(R)-1-(naphthalen-1-yl)-ethylamino]-pyrrolidin-1-yl]benzoylglycine tert-butyl of Example 3.016 was added several drops of chloroform, and dissolved therein, and then, 10 ml of trifluoroacetic acid was added to the mixture, and the resulting mixture was stirred at room temperature for 19 hours. The solvent was evaporated and the obtained residue was purified by LC/MS, and further purified by silica gel thin-layer chromatography (chloroform:methanol:acetic acid=70:30:3) to obtain N-4-[(S)-3-[(R)-1-(naphthalen-1-yl)-ethylamino]-pyrrolidin-1-yl]benzoyl glycine.

(2) To N-4-[(S)-3-[(R)-1-(naphthalen-1-yl)-ethylamino]-pyrrolidin-1-yl]benzoylglycine obtained by the above-mentioned (1) was added 4 ml of a solution of 4M hydrochloric acid in dioxane, and the mixture was stirred for a while. The solvent was evaporated, and then toluene was added and evaporated. 48 mg of the resulting pale yellowish powder was completely dissolved in a small amount of methanol and chloroform, and isopropyl ether was added thereto to crystallize the product to obtain 41 mg of N-4-[(S)-3-[(R)-1-(naphthalen-1-yl)-ethylamino]-pyrrolidin-1-yl]benzoyl glycine hydrochloride (the following Table X, Example 12.002).

Example 12.003

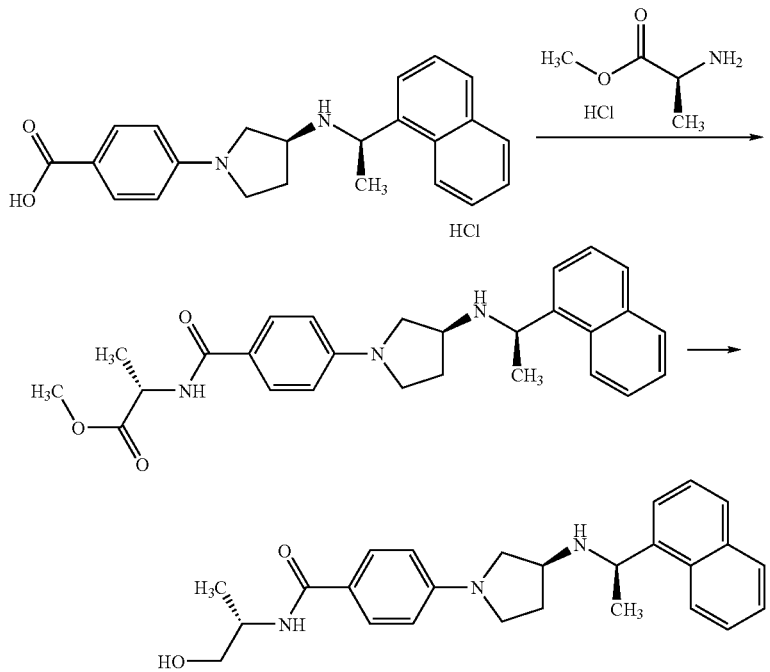

-continued

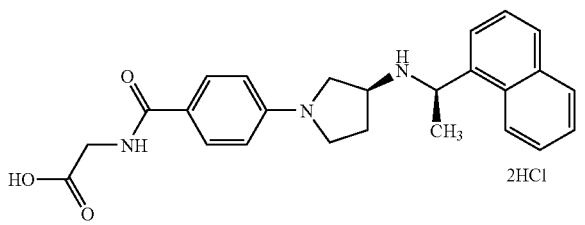

(1) To a solution of 150 mg of 4-[(S)-3-[(R)-1-(naphthalen-1-yl)ethylamino]pyrrolidin-1-yl]benzoic acid hydrochloride of Example 3.001 and 58 mg of (1)-alanine methyl ester hydrochloride in 5 ml of DMF were added 163 mg of 1-[3-(dimethylaminopropyl)]-3-ethylcarbodiimide hydrochloride, 115 mg of 1-hydroxybenzotriazole and 125 μl of triethylamine, and the reaction mixture was stirred at room temperature for 1 day. To the reaction mixture were added water and ethyl acetate, the mixture was stirred and then the liquids were separated. The organic layer was dried and concentrated under reduced pressure, then, the residue was purified by NH silica gel column chromatography (hexane:

ethyl acetate=65:35→35:65) to obtain 31.9 mg of N-[(S)-1-methoxycarbonylethyl]-4-[(S)-3-[(R)-1-(naphthalen-1-yl)ethylamino]pyrrolidin-1-yl]benzamide.

MS.APCI (m/z): 446 [M+H]

(2) In 1 ml of THF was dissolved 31.9 mg of N—[(S)-1-methoxycarbonylethyl]-4-[(S)-3-[(R)-1-(naphthalen-1-yl)ethylamino]pyrrolidin-1-yl]benzamide, 3.0 mg of lithium borohydride was added thereto, and the mixture was stirred at room temperature for 1 day. To the reaction mixture was added a saturated aqueous ammonium chloride solution, and chloroform was added to the mixture and the mixture was stirred and then the liquids were separated.

The organic layer was dried and evaporated, and then, the residue was purified by NH silica gel thin-layer chromatography (chloroform:methanol=95:5) to obtain 14.7 mg of N—[(S)-1-hydroxypropan-2-yl]-4-[(S)-3-[(R)-1-(naphthalen-1-yl)-ethylamino]pyrrolidin-1-yl]benzamide (the following Table X, Example 12.003).

Examples 12.004 to 12.008

In the same manner as in the above-mentioned Example 12.003, the compounds of Examples 12.004 to 12.008 in the following Table X were obtained.

Example 12.009

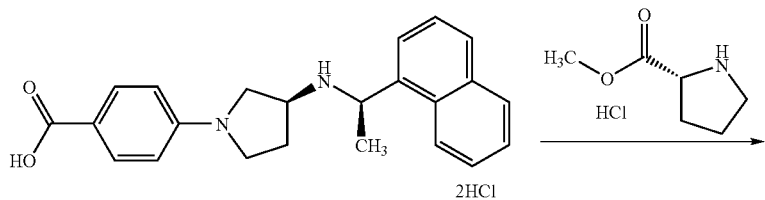

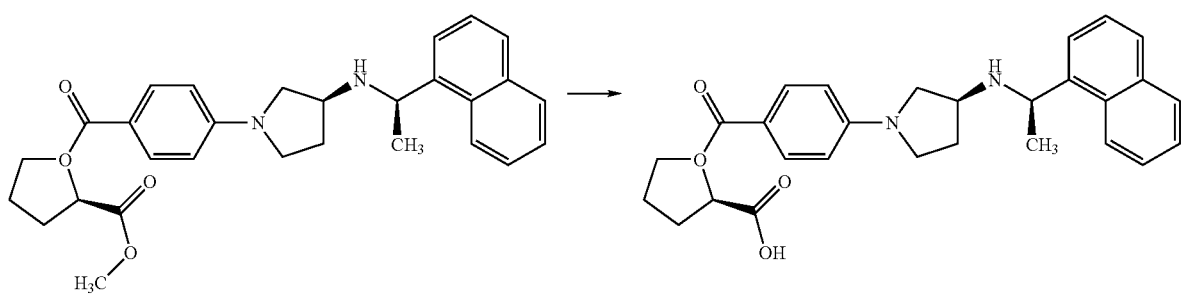

(1) To a solution of 200 mg of 4-[(S)-3-[(R)-1-(naphthalen-1-yl)ethylamino]pyrrolidin-1-yl]benzoic acid hydrochloride and 99.4 mg of (d)-proline methyl ester in 5 ml of DMF were added 230 mg of 1-[3-(dimethylaminopropyl)]-3-ethylcarbodiimide hydrochloride, 162 mg of 1-hydroxybenzotriazole and 176 μl of triethylamine, and the reaction mixture was stirred at room temperature for 1 day. To the reaction mixture were added water and ethyl acetate, the mixture was stirred and then the liquids were separated. The organic layer was dried and concentrated under reduced pressure, and then, the residue was purified by NH silica gel column chromatography (hexane:ethyl acetate=65:35→35:65) to obtain 161.0 mg of (d)-1-{4-[(S)-3-[(R)-1-(naphthalen-1-yl)ethylamino]pyrrolidin-1-yl]benzoyl}proline methyl ester.

MS.APCI (m/z): 472 [M+H]

(2) In 3 ml of ethanol was dissolved 80.5 mg of (d)-1-[4-[(S)-3-[(R)-1-(naphthalen-1-yl)ethylamino]pyrrolidin-1-yl]benzoyl]proline methyl ester, 171 μl of a 2N aqueous sodium hydroxide solution was added to the solution, and the mixture was stirred at room temperature for 1 day. After the reaction mixture was concentrated, 2 ml of water was added to the residue, and further 171 μl of 2N hydrochloric acid was added to the same. Precipitated solids were filtered and dried to obtain 39.0 mg of (d)-1-[4-[(S)-3-[(R)-1-(naphthalen-1-yl)ethylamino]pyrrolidin-1-yl]benzoyl]proline (the following Table X, Example 12.009).

Examples 12.010 to 12.016

In the same manner as in the above-mentioned Example 12.009, the compounds of Examples 12.010 to 12.016 in the following Table X were obtained.

Example 12.017

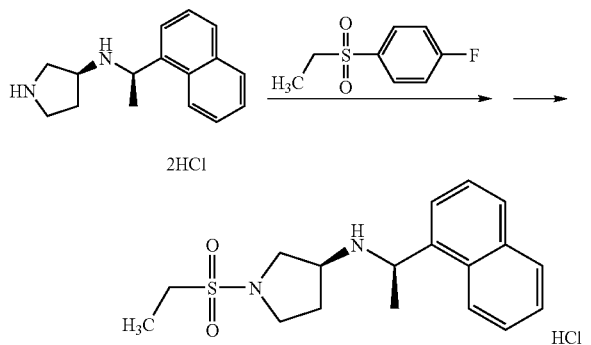

(1) To a solution of 150 mg of (S)-3-[(R)-1-(naphthalen-1-yl)ethylamino]pyrrolidine dihydrochloride and 108 mg of 4-fluorophenylethylsulfone in 2 ml of DMSO was added 263 mg of potassium carbonate, and the reaction mixture was stirred at 130° C. for 1 day. To the reaction mixture was added water and chloroform, the mixture was stirred and the liquids were separated. The organic layer was dried and evaporated, and then, the residue was purified by NH silica gel column chromatography (hexane:ethyl acetate=80: 20→40:60) to obtain 132.5 mg of 4-[(S)-3-[(R)-1-(naphthalen-1-yl)ethylamino]pyrrolidin-1-yl]phenylethylsulfone.

MS.APCI (m/z): 409 [M+H]

(2) In a mixed solvent comprising 2 ml of ethyl acetate and 1 ml of chloroform was dissolved 132.5 mg of 4-[(S)-3-[(R)-1-(naphthalen-1-yl)ethylamino]pyrrolidin-1-yl]phenylethylsulfone, 0.8 ml of a solution of 4N hydrogen chloride in dioxane was added thereto, and the precipitated solids were filtered and dried. This was recrystallized from ethanol to obtain 40.0 mg of 4-[(S)-3-[(R)-1-(naphthalen-1-yl)-ethylamino]pyrrolidin-1-yl]phenylethylsulfone hydrochloride (the following Table X, Example 12.017).

Examples 12.018 to 12.023

In the same manner as in the above-mentioned Example 12.017, the compounds of Examples 12.018 to 12.023 in the following Table X were obtained.

Example 12.024

(1) In the same manner as in the above-mentioned Example 12.017, (S)-1-(4-methanesulfonyl-3-methoxycarbonyl)-phenylpyrrolidin-3-yl-[(R)-1-(naphthalen-1-yl)ethyl]amine was obtained.

(2) In 2 ml of tetrahydrofuran was dissolved 70 mg of (S)-1-(4-methanesulfonyl-3-methoxycarbonyl)phenylpyrrolidin-3-yl-[(R)-1-(naphthalen-1-yl)ethyl]amine, 0.32 ml of a 1N aqueous sodium hydroxide solution was added thereto under ice-cooling, and the mixture was stirred overnight while gradually elevating the temperature to room temperature. Further, 0.32 ml of a 1N aqueous sodium hydroxide solution was added to the mixture, and the mixture was stirred at room temperature for a half day and then heated under refluxing for 2 hours. After cooling the mixture to room temperature, the mixture was neutralized with 1N hydrochloric acid. The reaction mixture was concentrated under reduced pressure, and the resulting solids were collected by filtration, washed with water and then with diisopropyl ether, and dried to obtain 50 mg of (S)-1-(3- carboxy-4-methanesulfonyl)phenylpyrrolidin-3-yl-[(R)-1-(naphthalen-1-yl)ethyl]amine (the following Table X, Example 12.024).

Examples 12.025 to 12.027

In the same manner as in the above-mentioned Example 12.024, the compounds of Examples 12.025 to 12.027 in the following Table X were obtained.

Example 12.028

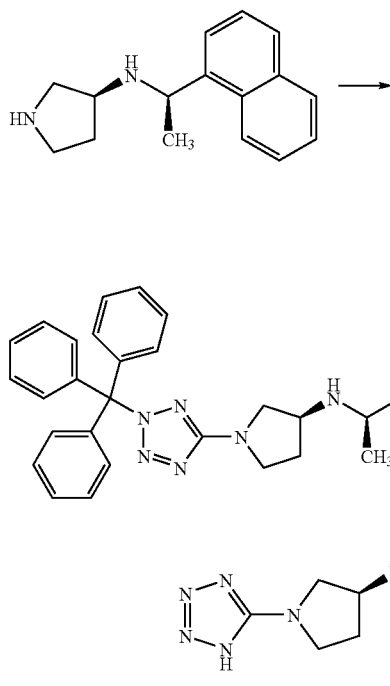

(1) In the same manner as in the above-mentioned Example 1.082(1), (S)-1-(2-trityl-2H-tetrazol-5-yl)pyrrolidin-3-yl-[(R)-1-(naphthalen-1-yl)ethyl]amine was obtained.
MS.APCI (m/z): 627 [M+H]+

(2) A mixture of 361 mg of (S)-1-(2-trityl-2H-tetrazol-5-yl)pyrrolidin-3-yl-[(R)-1-(naphthalen-1-yl)ethyl]amine in addition of 1 ml of water and a solution of 4M hydrochloric acid-dioxane was allowed to stand at room temperature for 4 hours. To the residue obtained by concentrated under reduced pressure, ethanol was added, and the mixture was again concentrated under reduced pressure. To the residue was added ether, and the solid was pulverized and collected by filtration. By recrystallizing from ethanol, 185 mg of (S)-1-(1H-tetrazol-5-yl)pyrrolidin-3-yl-[(R)-1-(naphthalen-1-yl)ethyl]amine hydrochloride (the following Table X, Example 12.028) was obtained.

Example 12.029

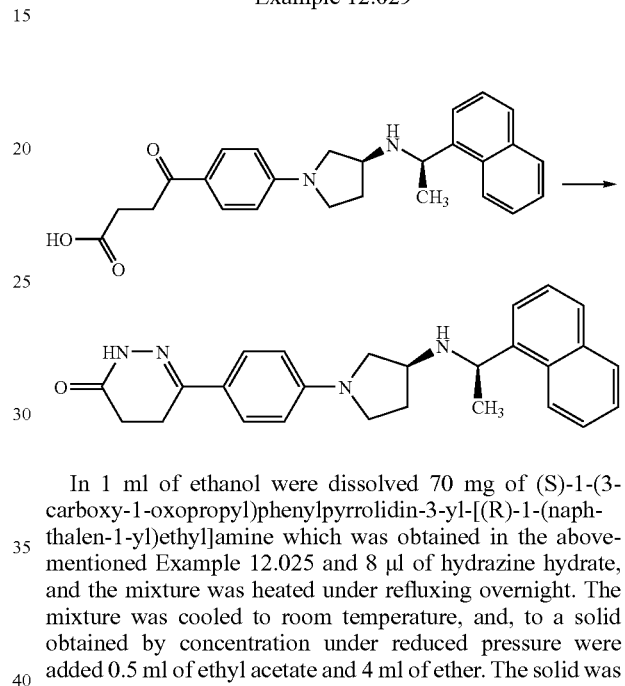

In 1 ml of ethanol were dissolved 70 mg of (S)-1-(3-carboxy-1-oxopropyl)phenylpyrrolidin-3-yl-[(R)-1-(naphthalen-1-yl)ethyl]amine which was obtained in the above-mentioned Example 12.025 and 8 μl of hydrazine hydrate, and the mixture was heated under refluxing overnight. The mixture was cooled to room temperature, and, to a solid obtained by concentration under reduced pressure were added 0.5 ml of ethyl acetate and 4 ml of ether. The solid was pulverized, collected by filtration, and dried to obtain 31 mg of (S)-1-(3-oxo-4,5-dihydro-2H-pyridazin-6-yl)phenyl-pyrrolidin-3-yl-[(R)-1-(naphthalen-1-yl)ethyl]amine (the following Table X, Example 12.029).

Example 12.030

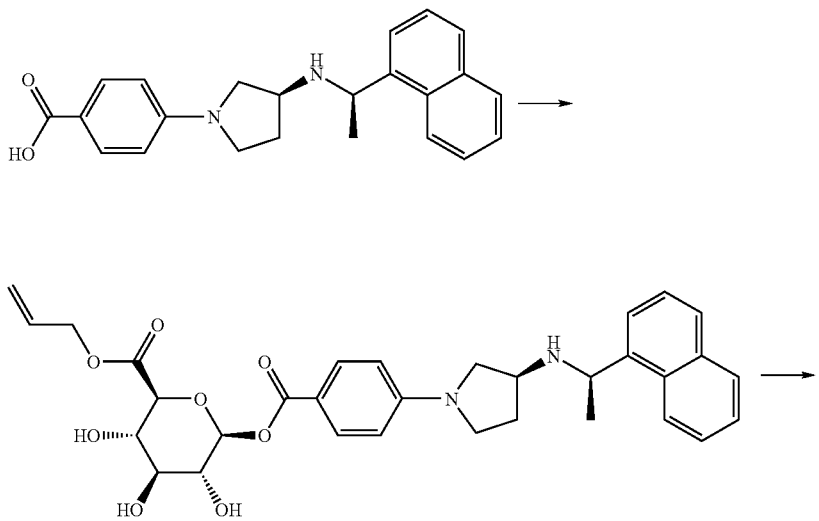

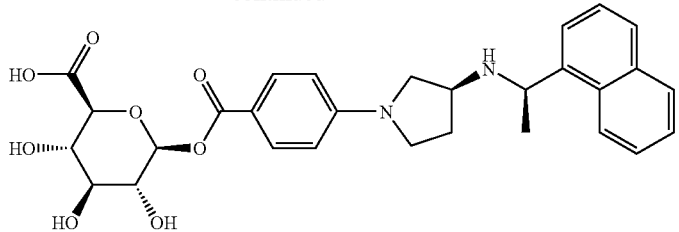

(1) Toluene was added to 4.37 g of (S)-1-(4-carboxyphenyl)-pyrrolidin-3-yl-[(R)-1-(naphthalen-1-yl)ethyl]amine of the above-mentioned Example 1.001, 1.42 g of D-glucuronic acid allyl ester and 3.18 g of triphenylphosphine, and the mixture was concentrated under reduced pressure and evaporated to dryness. To the mixture was added 100 ml of tetrahydrofuran, and to the mixture was added dropwise 2.39 ml of diisopropyl azodicarboxylate over 10 minutes under ice-cooling and stirring. The reaction mixture was stirred under ice-cooling for 1 hour, and the residue obtained by concentration under reduced pressure was purified by silica gel column chromatography (chloroform/methanol) to obtain 715 mg of allyl 2-[4-[(S)-3-[(R)-1-(naphthalen-1-yl)ethyl]-aminopiperidin-1-yl]-benzoyl]-D-glucuronate.

MS.APCI (m/z): 577 [M+H]+

(2) In 6 ml of tetrahydrofuran was dissolved 615 mg of allyl 2-[4-[(S)-3-[(R)-1-(naphthalen-1-yl)ethyl]aminopiperidin-1-yl]-benzoyl]-D-glucuronate, and the mixture was stirred under ice-cooling and in nitrogen atmosphere. To the mixture were added 91 μl of pyrrolidine, and then, 123 mg of tetrakistriphenylphosphine palladium, and the resulting mixture was stirred for 30 minutes. The residue obtained by concentration under reduced pressure was purified by LC-MS. Ether was added to the obtained solid, the solid was pulverized, collected by filtration, and dried to obtain 220 mg of 2-[4-[(S)-3-[(R)-1-(naphthalen-1-yl)ethyl]aminopiperidin-1-yl]-benzoyl]-D-glucuronic acid (Example 12.030 in the following Table X). (HPLC purity: 67.7%)

Example 12.031

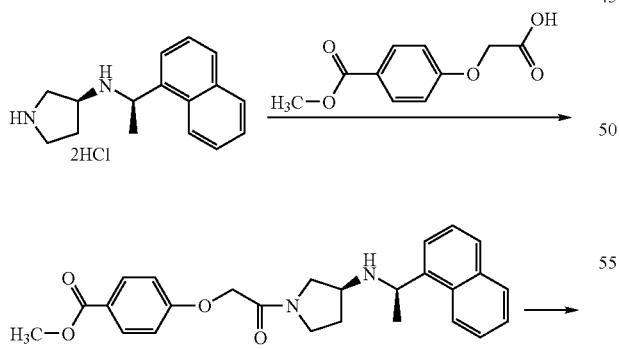

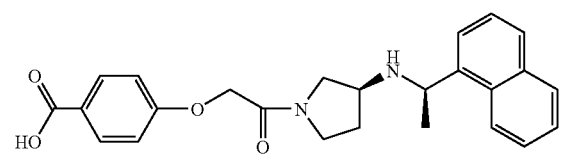

(1) In the same manner as in Example 5.017, 1-(4-methoxycarbonylphenoxyacetyl)-(S)-3-[(R)-1-(naphthalen-1-yl)ethyl-amino]pyrrolidine was obtained.

MS.APCI (m/z): 433 [M+H]+

(2) To a solution of 250 mg of 1-(4-methoxycarbonylphenoxyacetyl)-(S)-3-[(R)-1-(naphthalen-1-yl)ethylamino]-pyrrolidine in 5 ml of an ethanol was added 0.64 ml of a 2N aqueous sodium hydroxide solution, and the reaction mixture was stirred at room temperature for 5 hours. Moreover, the mixture was heated under refluxing overnight, and the reaction mixture was concentrated. 2 ml of water was added to the residue, and 0.64 ml of 2N hydrochloric acid was further added to the same and the precipitated solid was filtered and dried to obtain 26 mg of 1-(4-carboxylphenoxyacetyl)-(S)-3-[(R)-1-(naphthalen-1-yl)ethylamino] pyrrolidine (Example 12.031 in the following Table X).

Example 13.001

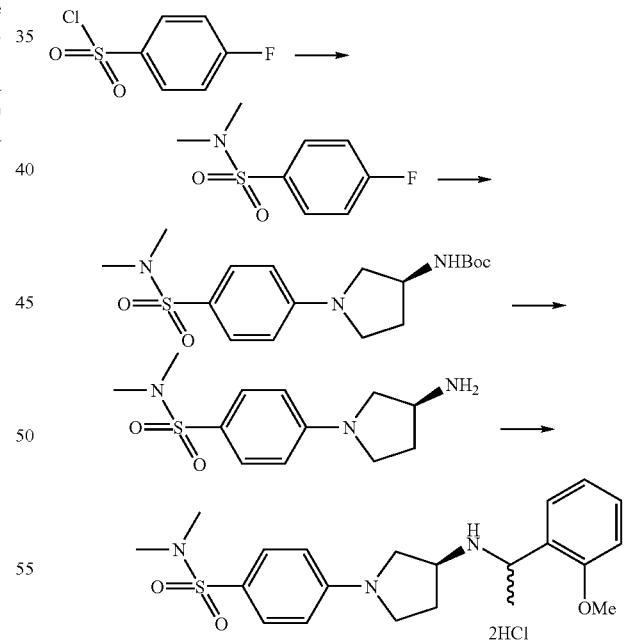

(1) A solution of 50 g of 4-fluorobenzenesulfonyl chloride in 250 ml of THF was cooled to 0° C., and then, 100 ml of an aqueous 50% dimethylamine solution was added dropwise thereto, and the mixture was stirred at room temperature for 1 day. To the reaction mixture were added water and ethyl acetate, the mixture was stirred and then the liquids were separated. The organic layer was washed with a saturated aqueous sodium bicarbonate solution and dried, the solvent was evaporated, and diisopropyl ether and hexane were added to the residue. Then, the precipitates were collected by filtration and washed with hexane to obtain 49.9 g of 4-fluoro-N,N-dimethyl-benzenesulfonamide.

(2) In 600 ml of DMSO were suspended 25 g of (S)-(−)-3-(tert-butoxycarbonylamino)pyrrolidine, 47.9 g of 4-fluoro-N,N-dimethyl-benzenesulfonamide and 139 g of potassium carbonate, and the mixture was stirred at 130° C. for 1 day. To the reaction mixture were added water and ethyl acetate, the resulting mixture was stirred and the liquids were separated. The organic layer was washed with water, and then dried, and the solvent was evaporated. The residue was dissolved in chloroform, NH silica gel was added thereto and the mixture was allowed to stand for a while, and silica gel was filtered off. The silica gel was further washed with ethyl acetate. The filtrate and the washed solution were combined, and the residue obtained by concentration under reduced pressure was purified by silica gel column chromatography (hexane:ethyl acetate=80:20→67:33) to obtain 8.39 g of tert-butyl [(S)-1-(4-dimethylsulfamoylphenyl)-pyrrolidin-3-yl]carbamate.

MS.APCI (m/z): 370 [M+H]+

(3) In ethyl acetate was dissolved 8.39 g of tert-butyl [(S)-1-(4-dimethylsulfamoylphenyl)-pyrrolidin-3-yl]-carbamate, 200 ml of a solution of 4M hydrochloric acid in ethyl acetate was added thereto, and the mixture was stirred at room temperature for 3 days. The solvent was evaporated, and then, diethyl ether was added to the residue, and the precipitates were collected by filtration to obtain 4-[(S)-3-aminopyrrolidin-1-yl]-N,N-dimethyl-benzenesulfonamide dihydrochloride. To the 4-[(S)-3-aminopyrrolidin-1-yl]-N,N-dimethyl-benzenesulfonamide dihydrochloride were added a saturated aqueous sodium bicarbonate solution and chloroform, the mixture was stirred and the liquids were separated. The organic layer was dried and concentrated under reduced pressure to obtain 5.85 g of 4-[(S)-3-aminopyrrolidin-1-yl]-N,N-dimethyl-benzenesulfonamide.

MS.APCI (m/z): 270 [M+H]+

(4) To a solution of 54 mg of 4-[(S)-3-aminopyrrolidin-1-yl]-N,N-dimethyl-benzenesulfonamide and 30 mg of 2-methoxyacetophenone in 1 ml of THF was added 85 mg of titanium isopropoxide, and the mixture was stirred at room temperature for 1 day. Further, 12 mg of sodium borohydride was added to the reaction mixture, and then, 0.3 ml of methanol was added to the mixture, and the mixture was stirred at room temperature for 4 hours. To the reaction mixture was added 0.5 ml of 28% aqueous ammonia solution, the mixture was stirred, and then, insoluble materials were removed and the solvent was evaporated. The residue was purified by LC/MS to obtain 61 mg of 4-[(S)-3-[1-(2-methoxyphenyl)ethylamino]pyrrolidin-1-yl]-N,N-dimethyl-benzenesulfonamide. The 4-[(S)-3-[1-(2-methoxyphenyl)ethylamino]pyrrolidin-1-yl]-N,N-dimethylbenzenesulfonamide was dissolved by adding 1 ml of tert-butanol, 0.15 ml of 2M aqueous hydrochloric acid was added thereto, and after stirring the mixture, it was freeze-dried to obtain 4-[(S)-3-[1-(2-methoxyphenyl) ethylamino]-pyrrolidin-1-yl]-N,N-dimethyl-benzenesulfonamide dihydrochloride (the following Table Y, Example 13.001).

Examples 13.002 to 13.003

In the same manner as in the above-mentioned Example 13.001, the compounds of Examples 13.002 to 13.003 in the following Table Y were obtained.

Reference Example 1.001

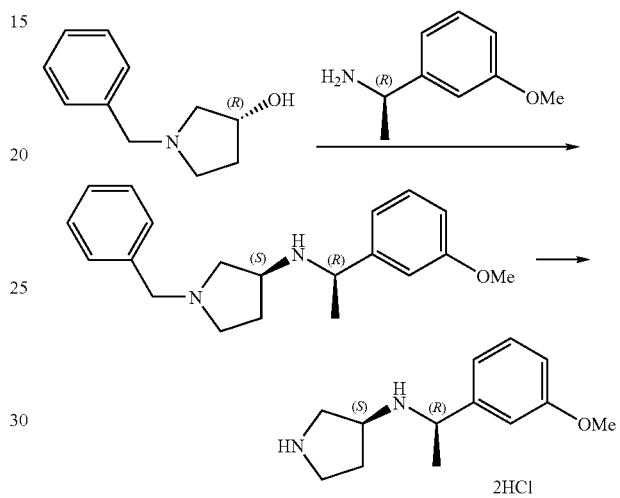

(1) To a solution of 8.0 g of (R)-1-benzyl-3-pyrrolidinol and 16.5 ml of diisopropylethylamine dissolved in 400 ml of methylene chloride was added dropwise a solution of 13.4 g of anhydrous trifluoromethanesulfonic acid in 50 ml of a methylene chloride at −20° C. or lower. The reaction mixture was stirred for 15 minutes while maintaining it to −20° C., then, a solution of 9.88 g of (R)-1-(3-methoxyphenyl)-ethylamine in 100 ml of methylene chloride was added dropwise to the mixture at −20° C. or lower, and the reaction mixture was stirred at room temperature for 16 hours. To the reaction mixture was added a saturated aqueous sodium bicarbonate solution and chloroform, the mixture was stirred and the liquids were separated. The organic layer was dried and concentrated, and the residue was purified by silica gel column chromatography (chloroform: methanol=1:0→50:1) and NH silica gel column chromatography (hexane:ethyl acetate=25:1→10:1) to obtain 3.98 g of (S)-(1-benzyl-pyrrolidin-3-yl)-[(R)-1-(3-methoxyphenyl)ethyl]amine.

MS.APCI (m/z): 311 [M+H]+

(2) To a solution of 3.67 g of (S)-(1-benzylpyrrolidin-3-yl)-[(R)-1-(3-methoxyphenyl)ethyl]amine dissolved in 100 ml of methanol were added 830 mg of palladium hydroxide and 8.85 ml of a solution of 4M hydrochloric acid in dioxane, and the mixture was shaken under hydrogen atmosphere at 3 atm at room temperature for 3 days. Palladium hydroxide was removed, and the solvent was evaporated. To the residue was added methanol, and the resulting precipitates were collected by filtration, washed with methanol and dried to obtain 1.14 g of (S)-3-[(R)-1-(3-methoxyphenyl)-ethylamino]pyrrolidine dihydrochloride (the following Reference example Table, Reference example 1.001).

Reference Example 1.002

(1) By using 8.0 g of (S)-1-benzyl-3-pyrrolidinol as a starting compound, the same procedure was carried out as in Reference example 1.001 (1) to obtain 4.36 g of (R)-(1-benzylpyrrolidin-3-yl)-[(R)-1-(3-methoxyphenyl)ethyl]amine.
MS.APCI (m/z): 311 [M+H]+

(2) By using (R)-(1-benzylpyrrolidin-3-yl)-[(R)-1-(3-methoxyphenyl)ethyl]amine, the same procedure was carried out as in Reference example 1.001 (2) to obtain (R)-3-[(R)-1-(3-methoxyphenyl)ethylamino]pyrrolidine dihydrochloride (Reference example 1.002 in the following Reference example Table).

Reference Example 1.003

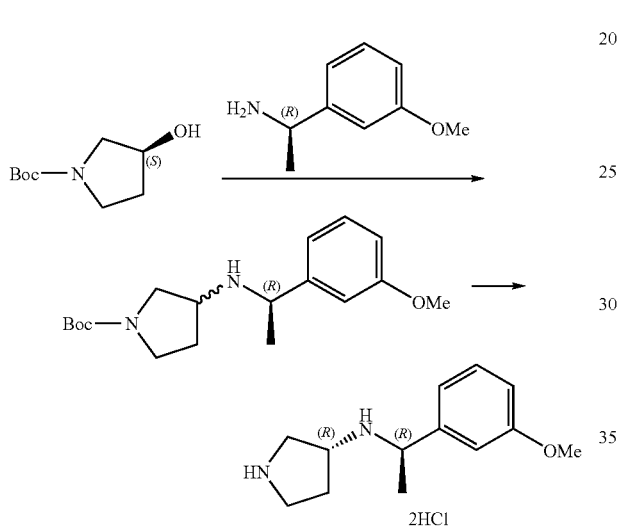

(1) To a solution of 25 g of tert-butyl (S)-3-hydroxypyrrolidine-1-carboxylate and 25.9 g of diisopropylethylamine dissolved in 500 ml of methylene chloride was added dropwise 100 ml of a solution of 49 g of anhydrous trifluoromethanesulfonic acid in methylene chloride at −20° C. or lower. The reaction mixture was stirred for 15 minutes while maintaining it to −20° C., and then, to the mixture was added dropwise 100 ml of a solution of 24.2 g of (R)-1-(3-methoxyphenyl)ethylamine in methylene chloride at −20° C. or lower, and the reaction mixture was stirred at room temperature for 16 hours. To the reaction mixture were added a saturated aqueous sodium bicarbonate solution and chloroform, the mixture was stirred and the liquids were separated. The organic layer was dried and the solvent was evaporated, and the residue was purified by silica gel column chromatography (hexane:ethyl acetate=2:1→1:2) to obtain 19.32 g of tert-butyl 3-[(R)-1-(3-methoxyphenyl)ethylamino]pyrrolidine-1-carboxylate.

(2) To a solution of 19.32 g of tert-butyl 3-[(R)-1-(3-methoxyphenyl)ethylamino]pyrrolidine-1-carboxylate dissolved in 30 ml of chloroform was added 300 ml of a solution of 4M hydrochloric acid in dioxane, and the mixture was stirred at room temperature for 16 hours. The resulting precipitates were collected by filtration, washed with ethyl acetate, and recrystallized from methanol and tetrahydrofuran twice to obtain 8.54 g of (R)-3-[(R)-1-(3-methoxyphenyl)ethylamino]pyrrolidine dihydrochloride (the following Reference example Table, Reference example 1.003).

Reference Example 1.004

By using tert-butyl (R)-3-hydroxypyrrolidine-1-carboxylate, the same procedures were carried out as in Reference example 1.003 (1) and (2) to obtain (S)-3-[(R)-1-(3-methoxyphenyl)ethylamino]pyrrolidine dihydrochloride (Reference example 1.004 in the following Reference example Table).

Reference Example 1.005

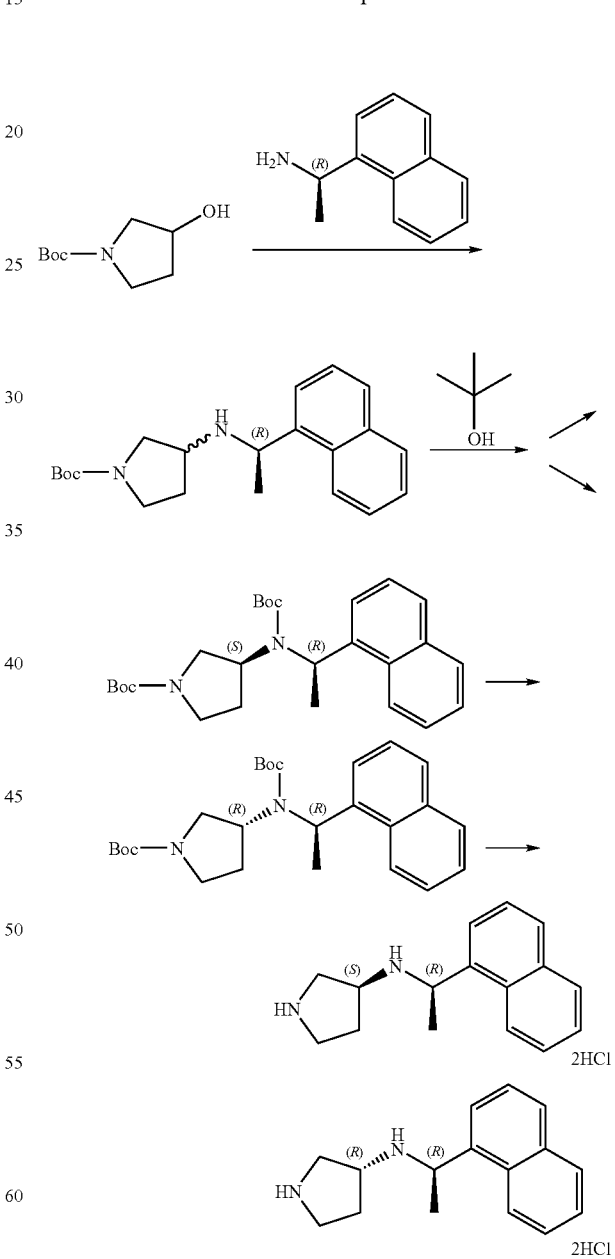

(1) To a solution of 25 g of tert-butyl 3-hydroxypyrrolidine-1-carboxylate and 25.9 g of diisopropylethylamine dissolved in 250 ml of methylene chloride was added dropwise a solution of 49 g of anhydrous trifluoromethanesulfonic acid in 50 ml of methylene chloride at −20° C. or lower. The reaction mixture was stirred for 15 minutes while maintaining it to −20° C., and to the mixture was added dropwise 125 ml of a solution of 27.4 g of (R)-(+)-1-(1-naphthyl)ethylamine in methylene chloride at −20° C. or lower, and the reaction mixture was stirred at room temperature for 4.5 hours. To the reaction mixture were added a saturated aqueous sodium bicarbonate solution and chloroform, the mixture was stirred and the liquids were separated. The organic layer was washed with water and a saturated brine, dried and the solvent was evaporated, and then, the residue was purified by silica gel column chromatography (hexane:ethyl acetate=4:1→1:1) to obtain 25.8 g of tert-butyl (R)-3-[1-(naphthalen-1-yl)ethylamino]-pyrrolidine-1-carboxylate. MS.APCI (m/z): 341 [M+H]+

(2) To a solution of 36.3 g of triphosgene dissolved in 600 ml of methylene chloride was added dropwise a solution of 62.50 g of tert-butyl (R)-3-[1-(naphthalen-1-yl)ethylamino]pyrrolidine-1-carboxylate and 76.4 ml of triethylamine in 250 ml of methylene chloride at −20° C., and the mixture was stirred at room temperature for 1 hour. To the reaction mixture was added water, the mixture was stirred and the liquids were separated. The organic layer was dried, and the solvent was evaporated. To the residue were added 1.48 L of tert-butanol and 50 ml of diisopropylethylamine, and the mixture was stirred at 70° C. for 16 hours. The reaction mixture was evaporated, and the residue was purified by silica gel column chromatography (hexane:ethyl acetate=10:1→8:1) to obtain 24.98 g of tert-butyl (S)-3-[tert-butoxycarbonyl-[(R)-1-(naphthalen-1-yl)ethyl]amino]pyrrolidine-1-carboxylate and 26.83 g of tert-butyl (R)-3-[tert-butoxycarbonyl-[(R)-1-(naphthalen-1-yl)ethyl]amino]pyrrolidine-1-carboxylate, respectively.

(3) To a solution of 28.9 g of tert-butyl (S)-3-[tert-butoxycarbonyl-[(R)-1-(naphthalen-1-yl)ethyl]amino]-pyrrolidine-1-carboxylate dissolved in 60 ml of chloroform was added dropwise 116 ml of a solution of 4M hydrochloric acid in dioxane, and the mixture was stirred at room temperature for 16 hours. The resulting precipitates were collected by filtration, washed with diethyl ether, crystallized from ethanol-diethyl ether, washed with diethyl ether and dried to obtain 22.38 g of (S)-3-[(R)-1-(naphthalen-1-yl)ethylamino]pyrrolidine dihydrochloride (Reference example 1.005(a) in the following Reference example Table).

Also, by using 21.8 g of tert-butyl (R)-3-[tert-butoxycarbonyl-[(R)-1-(naphthalen-1-yl)ethyl]amino]pyrrolidine-1-carboxylate, the same procedure was carried out to obtain 15.92 g of (R)-3-[(R)-1-(naphthalen-1-yl)ethylamino]pyrrolidine dihydrochloride (the following Reference example 1.005(b)).

Reference Example 1.006

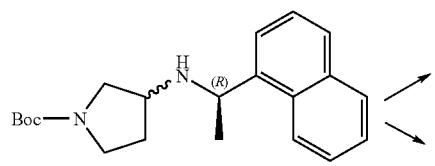

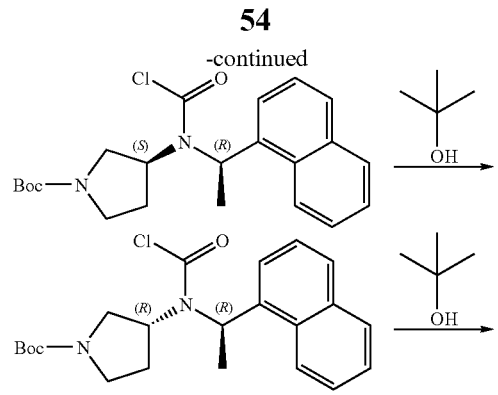

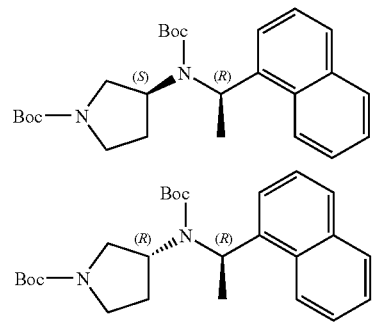

(1) To a solution of 14.9 g of triphosgene dissolved in 400 ml of methylene chloride was added dropwise a solution containing 25.68 g of tert-butyl (R)-3-[1-(naphthalen-1-yl)ethylamino]pyrrolidine-1-carboxylate (the compound obtained in the above-mentioned Reference example 1.005 (1)) and 31.5 ml of triethylamine in 100 ml of methylene chloride at −20° C. Further, 7.5 g of triphosgene was added to the same, and the mixture was stirred at room temperature for 30 minutes. Water was added to the reaction mixture, the mixture was stirred and the liquids were separated. The organic layer was dried, the solvent was evaporated, and the residue was purified by silica gel column chromatography (hexane:ethyl acetate=6:1→2:1) to obtain 10.63 g of tert-butyl (S)-3-[chlorocarbonyl-[(R)-1-(naphthalen-1-yl)ethyl]amino]pyrrolidine-1-carboxylate and 9.22 g of tert-butyl (R)-3-[chlorocarbonyl-[(R)-1-(naphthalen-1-yl)ethyl]amino]pyrrolidine-1-carboxylate shown in the following Reference example Table, respectively.

(2) To 18.52 g of tert-butyl (S)-3-[chlorocarbonyl-[(R)-1-(naphthalen-1-yl)ethyl]amino]pyrrolidine-1-carboxylate was added 1.0 liter of tert-butanol, and the mixture was stirred at 60° C. for 2 days. The reaction mixture was concentrated, and then, the residue was purified by silica gel column chromatography (hexane:ethyl acetate=10:1) to obtain 9.24 g of tert-butyl (S)-3-[tert-butoxycarbonyl-[(R)-1-(naphthalen-1-yl)ethyl]amino]pyrrolidine-1-carboxylate (the following Reference example 1.006(a)).

Also, by using 15.58 g of tert-butyl (R)-3-[chlorocarbonyl-[(R)-1-(naphthalen-1-yl)ethyl]amino]pyrrolidine-1-carboxylate, the same procedure was carried out as mentioned above to obtain 7.03 g of tert-butyl (R)-3-[tert-butoxycarbonyl-[(R)-1-(naphthalen-1-yl)ethyl]amino]pyrrolidine-1-carboxylate (the following Reference example Table, Reference example 1.006(b)).

Reference Example 2.001

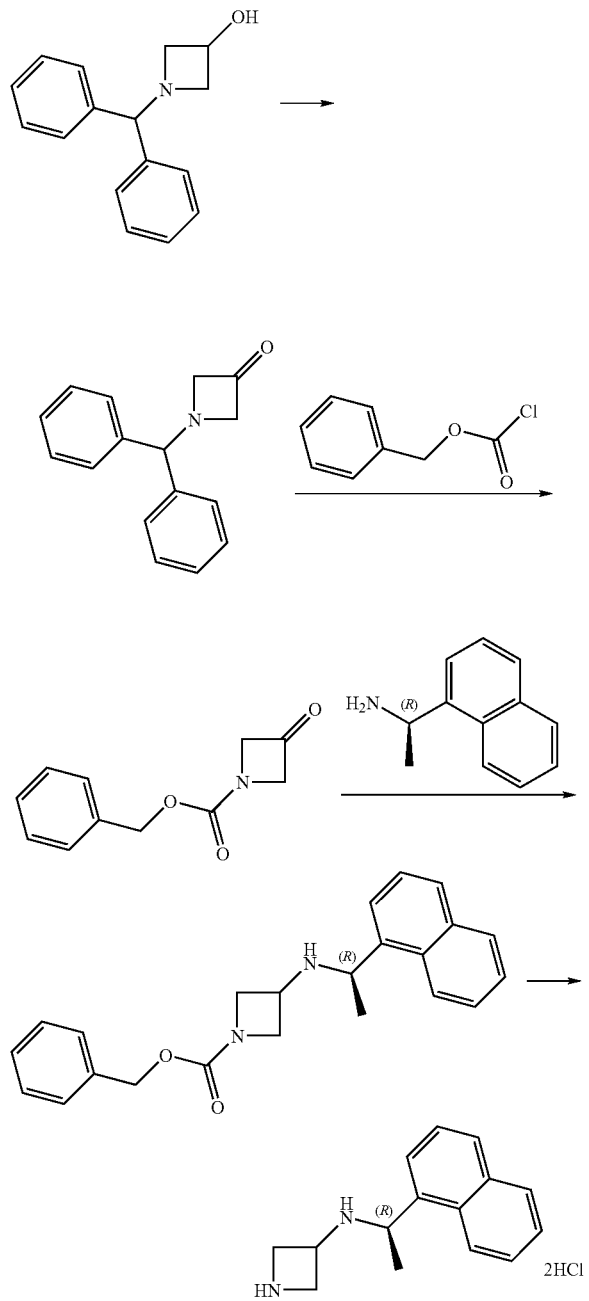

(1) 1-Benzhydrylazetidin-3-one was synthesized by the same method as described in a literature (CHEM LETT 1999 (7) 605-606).

That is, to a solution of 27.27 g of 1-benzhydrylazetan-3-ol dissolved in 225 ml of dimethylsulfoxide was added 135.5 ml of triethylamine, 59.80 g of sulfur trioxide-pyridine complex was added thereto under ice-cooling, and the mixture was stirred at room temperature for 2.5 hours. To the reaction mixture were added water and ethyl acetate, the mixture was stirred and the liquids were separated. The organic layer was washed with a saturated brine, dried and concentrated. The residue was purified by silica gel column chromatography (hexane:ethyl acetate=15:1) to obtain 21.35 g of 1-benzhydrylazetidin-3-one.

(2) To a solution of 5.0 g of 1-benzohydrylazetidin-3-one dissolved in 75 ml of toluene was added 2.98 ml of benzyloxycarbonyl chloride, and the mixture was stirred at 80° C. for 4 hours. The reaction mixture was evaporated, and then, to the residue were added water and ethyl acetate, the mixture was stirred and the liquids were separated. The organic layer was washed with water and a saturated brine, dried and concentrated. The residue was purified by silica gel column chromatography (hexane:ethyl acetate=19:1→4:1), and then, hexane was added thereto, and after collecting the precipitate by filtration, it was washed with hexane to obtain 2.73 g of benzyl 3-oxoazetidine-1-carboxylate.

(3) To a solution of 8.51 g of benzyl 3-oxoazetidine-1-carboxylate and 7.10 g (R)-(+)-1-(1-naphthyl)ethylamine dissolved in 170 ml of methylene chloride, 7.49 g of magnesium sulfate was added to the solution. The mixture was stirred at room temperature for 3 hours, and then, 9.5 ml of acetic acid and 13.18 g of sodium triacetoxy borohydride were added thereto, and the mixture was stirred at room temperature for 1 hour. To the reaction mixture was added a saturated aqueous sodium bicarbonate solution to make the mixture basic, chloroform was added to the same and the mixture was stirred, and the liquids were separated. The organic layer was dried and concentrated, and the residue was purified by NH silica gel column chromatography (hexane:ethyl acetate=4:1→1:1) to obtain 7.90 g of benzyl 3-[(R)-1-(naphthalen-1-yl)ethylamino]-azetidine-1-carboxylate.

(4) To a solution of 9.45 g of benzyl 3-[(R)-1-(naphthalen-1-yl)ethylamino]azetidine-1-carboxylate dissolved in 190 ml of methanol, 1 g of palladium carbon (10% wet) was added thereto, and the reaction was carried out under hydrogen atmosphere at room temperature for 4 hours. Palladium carbon was removed, the solvent was evaporated, and the residue was purified by NH silica gel column chromatography (chloroform:methanol=1:0→19:1) to obtain 4.60 g of 3-[(R)-1-(naphthalen-1-yl)ethylamino] azetidine. To a solution of 4.60 g of 3-[(R)-1-(naphthalen-1-yl)ethylamino]azetidine dissolved in 30 ml of ethyl acetate, under ice-cooling, 13 ml of a solution of 4M hydrochloric acid in ethyl acetate was added dropwise, and the mixture was stirred for a while.

After collecting the resulting precipitates by filtration, the product was recrystallized from methanol and hexane, and washed with diethyl ether to obtain 5.86 g of 3-[(R)-1-(naphthalen-1-yl)ethylamino]azetidine dihydrochloride (the following Reference example Table, Reference example 2.001).

Reference Example 3.001

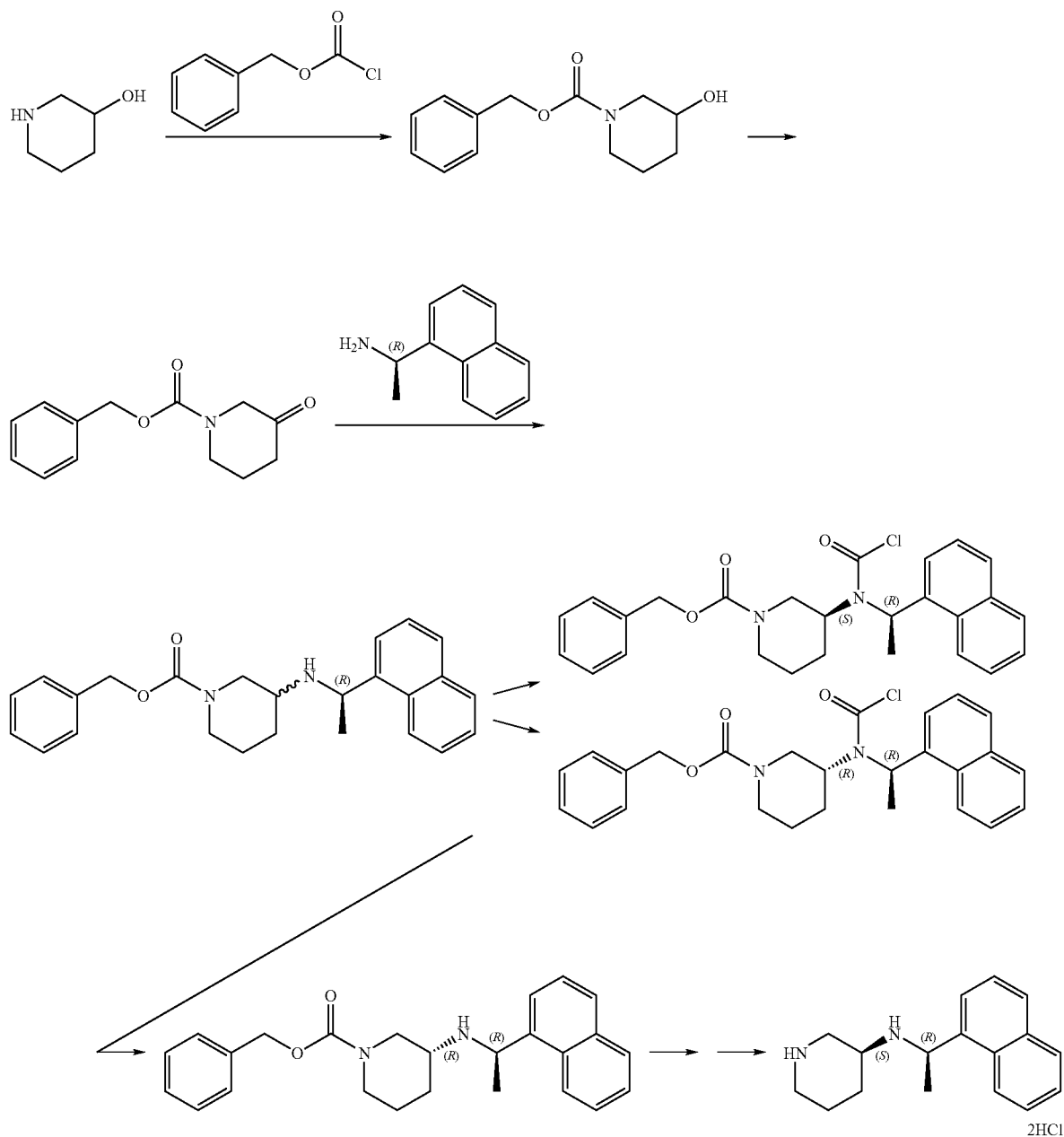

(1) To a mixed solution containing 33.5 g of 3-hydroxypiperidine and 62.7 ml of triethylamine dissolved in 250 ml of methylene chloride was added dropwise a solution of 55.7 ml of benzyloxycarbonyl chloride in 150 ml of methylene chloride, and the mixture was stirred at room temperature for 16 hours. To the reaction mixture were added a saturated aqueous citric acid and chloroform, the mixture was stirred and the liquids were separated. The organic layer was dried, the solvent was evaporated, and the residue was purified by silica gel column chromatography (hexane:ethyl acetate=4:1→0:1) to obtain 75.5 g of benzyl 3-hydroxypiperidine-1-carboxylate. MS.APCI (m/z): 236 [M+H]+

(2) 800 ml of a solution of 52.4 ml of oxalyl chloride in methylene chloride was cooled to −78° C., 53.2 ml of DMSO was added dropwise to the solution, and the mixture was stirred at −78° C. for 0.5 hour. A solution of 75.5 g of benzyl 3-hydroxypiperidine-1-carboxylate dissolved in 200 ml of methylene chloride was added dropwise to the mixture, and further 293 ml of triethylamine was added dropwise to the same, and the mixture was stirred for 16 hours while a temperature thereof was gradually raised to room temperature. To the reaction mixture were added a saturated aqueous sodium bicarbonate solution and chloroform, the mixture was stirred and the liquids were sepa rated. The organic layer was dried and concentrated to obtain 83.7 g of 1-benzyloxycarbonyl-3-piperidone. MS.APCI (m/z): 234 [M+H]+

(3) To a solution of 83.7 g of 1-benzyloxycarbonyl-3-piperidone dissolved in 1.2 liters of methylene chloride was added 55.0 g of (R)-(+)-1-(1-naphthyl)ethylamine, and after the mixture was stirred at room temperature for 2 hours, 69 ml of acetic acid and 160 g of sodium triacetoxy borohydride were added to the mixture, and the mixture was stirred at room temperature for 15 hours. To the reaction mixture was added an aqueous sodium hydroxide to make the mixture basic, and then, chloroform was added to the mixture, the mixture was stirred and the liquids were separated. The organic layer was dried and concentrated, and the residue was purified by silica gel column chromatography (hexane:ethyl acetate=4:1→0:1) to obtain 98.7 g of benzyl 3-[(R)-1-(naphthalen-1-yl)ethylamino]-piperidine-1-carboxylate. MS.APCI (m/z): 389 [M+H]+

(4) To a solution of 40.95 g of triphosgene dissolved in 800 ml of methylene chloride was added dropwise a mixed solution containing 80.6 g of benzyl 3-[(R)-1-(naphthalen-1-yl)ethylamino]piperidine-1-carboxylate and 86.6 ml of triethylamine dissolved in 200 ml of methylene chloride at 0° C., and the mixture was stirred at room temperature for 16 hours. To the reaction mixture was added water, the mixture was stirred and the liquids were separated. The organic layer was dried and concentrated, and the residue was washed with 200 ml of diethyl ether, and the crystal collected by filtration was recrystallized from chloroform and diethyl ether to obtain 48.9 g of benzyl (R)-3-[chlorocarbonyl-(R)-1-(naphthalen-1-yl)ethylamino]piperidine-1-carboxylate.

Further, the filtrate was purified by silica gel column chromatography (hexane:ethyl acetate=8:1→0:1) to obtain 5.82 g of benzyl (R)-3-[chlorocarbonyl-(R)-1-(naphthalen-1-yl)ethylamino]piperidine-1-carboxylate and 14.5 g of benzyl (S)-3-[chlorocarbonyl-(R)-1-(naphthalen-1-yl)ethylamino]piperidine-1-carboxylate.

(5) To a solution containing 54.6 g of benzyl (R)-3-[chlorocarbonyl-(R)-1-(naphthalen-1-yl)ethylamino]piperidine-1-carboxylate dissolved in 700 ml of tetrahydrofuran was added 350 ml of water, and the mixture was stirred under reflux for 15 hours. After tetrahydrofuran was evaporated, a saturated aqueous sodium bicarbonate solution and chloroform were added thereto, the mixture was stirred and the liquids were separated. The organic layer was dried and concentrated, and the residue was purified by silica gel column chromatography (hexane:ethyl acetate=4:1→0:1) to obtain 24.3 g of benzyl (R)-3-[(R)-1-(naphthalen-1-yl)ethylamino]piperidine-1-carboxylate. MS.APCI (m/z): 389 [M+H]+

(6) To a solution containing 24.2 g of benzyl (R)-3-[(R)-1-(naphthalen-1-yl)ethylamino]piperidine-1-carboxylate dissolved in 250 ml of methanol was added 2.5 g of palladium carbon (10% wet), and the mixture was shaked under hydrogen atmosphere at 3 atm at room temperature for 40 hours. Palladium carbon was removed, and the solvent was evaporated, the residue was washed with ethyl acetate-chloroform (10:1), and collected by filtration to obtain 15.3 g of (R)-3-[(R)-1-(naphthalen-1-yl)ethylamino]-piperidine (the following Reference example Table, Reference example 3.001(a)). MS.APCI (m/z): 255 [M+H]+

(7) By using 14.5 g of benzyl (S)-3-[chlorocarbonyl-(R)-1-(naphthalen-1-yl)ethylamino]piperidine-1-carboxylate, the same treatment was carried out as in the above-mentioned (5) to obtain 4.74 g of benzyl (S)-3-[(R)-1-(naphthalen-1-yl)ethylamino]piperidine-1-carboxylate. MS.APCI (m/z): 389 [M+H]+

Moreover, by using 4.7 g of benzyl (S)-3-[(R)-1-(naphthalen-1-yl)ethylamino]piperidine-1-carboxylate, the same treatment was carried out as in the above-mentioned (6) to obtain 2.89 g of (S)-3-[(R)-1-(naphthalen-1-yl)-ethylamino]piperidine. MS.APCI (m/z): 255 [M+H]+

(8) To a solution of 3.46 g of (S)-3-[(R)-1-(naphthalen-1-yl)ethylamino]piperidine dissolved in 15 ml of methanol was added dropwise 20 ml of a solution of 4M hydrochloric acid in ethyl acetate, and the mixture was stirred. The reaction mixture was concentrated under reduced pressure, diethyl ether was added to the residue, washed and dried to obtain 3.33 g of (S)-3-[(R)-1-(naphthalen-1-yl)ethylamino]-piperidine dihydrochloride (the following Reference example Table, Reference example 3.001(b)). MS.APCI (m/z): 255 [M+H]+

TABLE A1

| Example No. | $R^1$—X— | —N((CH$_2$)$_n$) | —Ar | Salt | Physical properties, etc. |
|---|---|---|---|---|---|
| 1.001 | 2-CF$_3$, 6-Me-phenyl | (R)-pyrrolidinyl | 3-OMe-phenyl | 2HCl | MS · APCI: 365 [M + H]+ |
| 1.002 | 2-CF$_3$, 6-Me-phenyl | (S)-pyrrolidinyl | 3-OMe-phenyl | 2HCl | MS · APCI: 365 [M + H]+ |

TABLE A1-continued

| Example No. | R¹—X— | —N(CH₂)n— | —Ar | Salt | Physical properties, etc. |
|---|---|---|---|---|---|
| 1.003 | 3-(F₃C)-C₆H₄- | N-methylpyrrolidin-3-yl | 3-MeO-C₆H₄- | 2HCl | MS·APCI: 365 [M + H]+ |
| 1.004 | 3-(F₃CO)-C₆H₄- | N-methylpyrrolidin-3-yl | 3-MeO-C₆H₄- | 2HCl | MS·APCI: 381 [M + H]+ |
| 1.005 | 3-(F₃C)-C₆H₄- | N-methylpyrrolidin-3-yl | 1-naphthyl | 2HCl | MS·APCI: 385 [M + H]+ |
| 1.006 | 3-(F₃CO)-C₆H₄- | N-methylpyrrolidin-3-yl | 1-naphthyl | 2HCl | MS·APCI: 401 [M + H]+ |
| 1.007 | 4-(F₃C)-C₆H₄- | N-methylpyrrolidin-3-yl | 1-naphthyl | Free form | MS·APCI: 385 [M + H]+ |
| 1.008 | 2-(F₃C)-C₆H₄- | N-methylpyrrolidin-3-yl | 1-naphthyl | 2HCl | MS·APCI: 385 [M + H]+ |
| 1.009 | 2-F-C₆H₄- | N-methylpyrrolidin-3-yl | 1-naphthyl | 2HCl | MS·APCI: 335 [M + H]+ |
| 1.010 | 4-F-C₆H₄- | N-methylpyrrolidin-3-yl | 1-naphthyl | 2HCl | MS·APCI: 335 [M + H]+ |

TABLE A1-continued
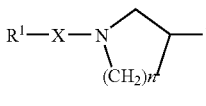
| Example No. | R¹—X— | —N(CH₂)ₙ· | —Ar | Salt | Physical properties, etc. |
|---|---|---|---|---|---|
| 1.011 | 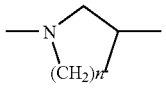 | 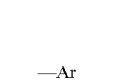 | 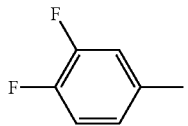 | 2HCl | MS · APCI: 353 [M + H]+ |
| 1.012 | 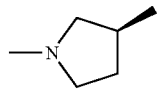 | 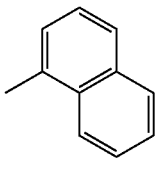 | 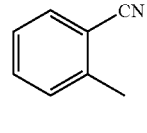 | 2HCl | MS · APCI: 342 [M + H]+ |
| 1.013 | 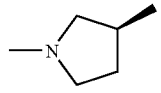 | 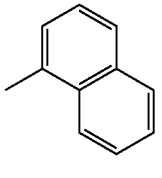 | 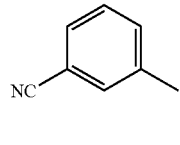 | 2HCl | MS · APCI: 342 [M + H]+ |
| 1.014 | 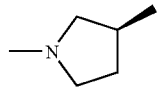 | 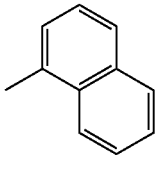 | 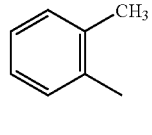 | 2HCl | MS · APCI: 331 [M + H]+ |
| 1.015 | 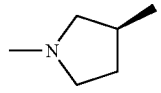 | 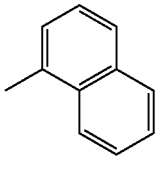 | 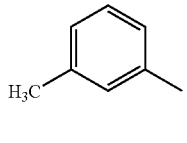 | 2HCl | MS · APCI: 331 [M + H]+ |
| 1.016 | 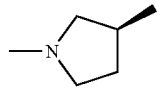 | 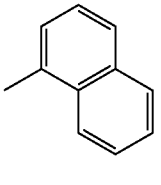 | 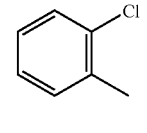 | 2HCl | MS · APCI: 351 [M + H]+ |

TABLE A1-continued
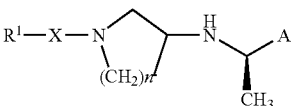
| Example No. | R¹—X— | —N(CH₂)n— with methylpyrrolidine | —Ar | Salt | Physical properties, etc. |
|---|---|---|---|---|---|
| 1.017 | 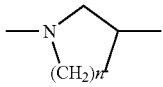 | 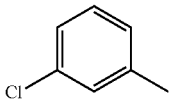 | 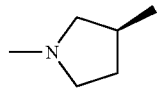 | 2HCl | MS·APCI: 351 [M + H]+ |
| 1.018 | 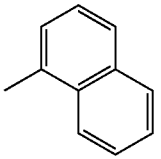 | 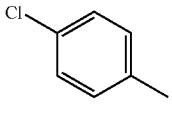 | 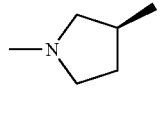 | 2HCl | MS·APCI: 351 [M + H]+ |
| 1.019 | 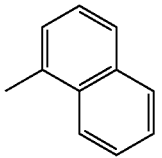 | 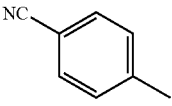 | 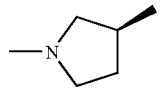 | 2HCl | MS·APCI: 342 [M + H]+ |
| 1.020 | 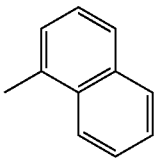 | 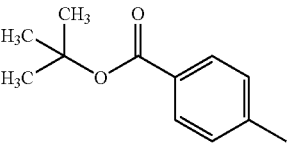 | 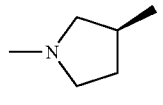 | Free form | MS·APCI: 417 [M + H]+ |
| 1.021 | 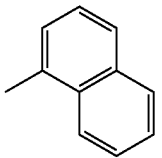 | 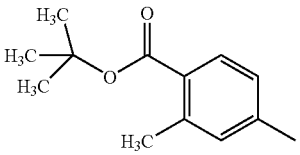 | 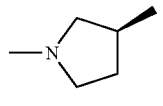 | Free form | MS·APCI: 431 [M + H]+ |
| 1.022 | 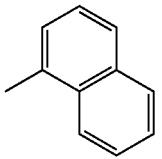 | 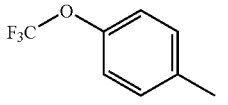 | 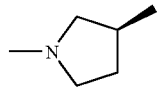 | 2HCl | MS·APCI: 401 [M + H]+ |
| 1.023 | 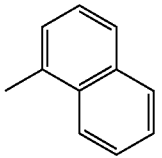 | 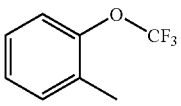 | 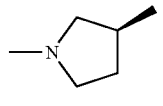 | 2HCl | MS·APCI: 401 [M + H]+ |
| 1.024 | 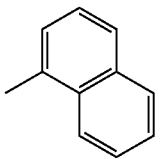 | 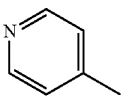 | 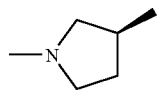 | 2HCl | MS·APCI: 318 [M + H]+ |

TABLE A1-continued

| Example No. | R¹—X— | —N(CH₂)ₙ— structure | —Ar | Salt | Physical properties, etc. |
|---|---|---|---|---|---|
| 1.025 | 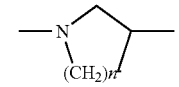 (2-methylpyridine) | 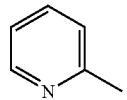 | 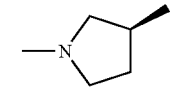 | 2HCl | MS·APCI: 318 [M + H]+ |
| 1.026 | 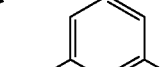 (3-methylpyridine) | 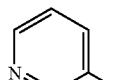 | 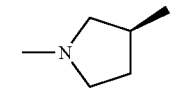 | 2HCl | MS·APCI: 318 [M + H]+ |
| 1.027 | 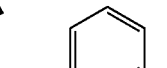 (2,3-dimethylpyridine) | 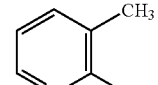 | 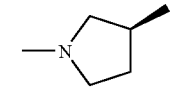 | 2HCl | MS·APCI: 332 [M + H]+ |
| 1.028 | 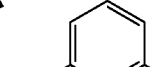 (2,4-dimethylpyridine) | 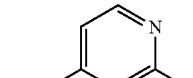 | 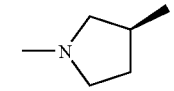 | 2HCl | MS·APCI: 332 [M + H]+ |
| 1.029 | 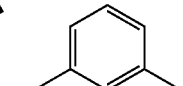 (2,5-dimethylpyridine) | 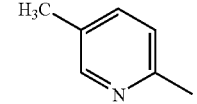 | 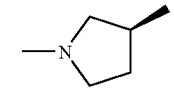 | 2HCl | MS·APCI: 332 [M + H]+ |
| 1.030 | 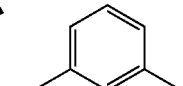 (2,6-dimethylpyridine) | 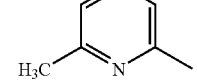 | 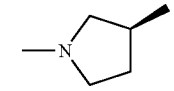 | 2HCl | MS·APCI: 332 [M + H]+ |
| 1.031 | 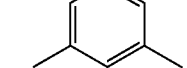 (2-methyl-3-CF₃-pyridine) | 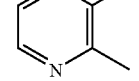 | 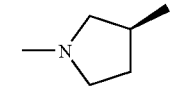 | 2HCl | MS·APCI: 386 [M + H]+ |
| 1.032 | 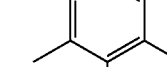 (2-methyl-4-CF₃-pyridine) | 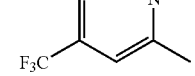 | 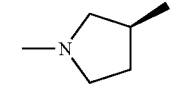 | 2HCl | MS·APCI: 386 [M + H]+ |

TABLE A1-continued

| Example No. | R¹—X— | —N(CH₂)ₙ pyrrolidine | —Ar | Salt | Physical properties, etc. |
|---|---|---|---|---|---|
| 1.033 | 5-(F₃C)-pyridin-2-yl | (R)-3-methylpyrrolidin-1-yl | naphthalen-1-yl | 2HCl | MS · APCI: 386 [M + H]+ |
| 1.034 | 6-(F₃C)-pyridin-2-yl | (R)-3-methylpyrrolidin-1-yl | naphthalen-1-yl | 2HCl | MS · APCI: 386 [M + H]+ |
| 1.035 | 6-(tert-butoxycarbonyl)pyridin-2-yl | (R)-3-methylpyrrolidin-1-yl | naphthalen-1-yl | Free form | MS · APCI: 418 [M + H]+ |
| 1.036 | pyrimidin-5-yl | (R)-3-methylpyrrolidin-1-yl | naphthalen-1-yl | 2HCl | MS · APCI: 319 [M + H]+ |
| 1.037 | 3-(F₃C)-phenyl | (S)-3-methylpyrrolidin-1-yl | naphthalen-1-yl | 2HCl | MS · APCI: 385 [M + H]+ |
| 1.038 | 3-(F₃CO)-phenyl | (S)-3-methylpyrrolidin-1-yl | naphthalen-1-yl | 2HCl | MS · APCI: 401 [M + H]+ |
| 1.039 | 2-cyanophenyl | (S)-3-methylpyrrolidin-1-yl | naphthalen-1-yl | 2HCl | MS · APCI: 342 [M + H]+ |
| 1.040 | 2-methylphenyl | (S)-3-methylpyrrolidin-1-yl | naphthalen-1-yl | 2HCl | MS · APCI: 331 [M + H]+ |

TABLE A1-continued
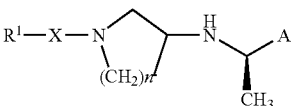
| Example No. | R¹—X— | —N(CH₂)ₙ (pyrrolidinyl) | —Ar | Salt | Physical properties, etc. |
|---|---|---|---|---|---|
| 1.041 | 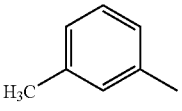 | 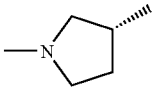 | 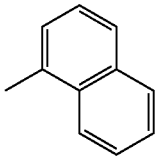 | 2HCl | MS·APCI: 331 [M + H]+ |
| 1.042 | 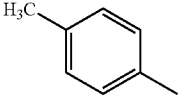 | 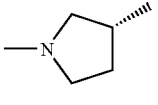 | 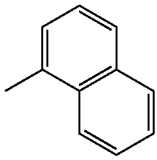 | 2HCl | MS·APCI: 331 [M + H]+ |
| 1.043 | 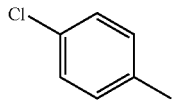 | 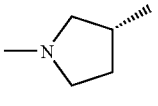 | 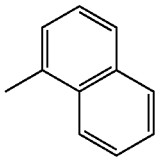 | 2HCl | MS·APCI: 351 [M + H]+ |
| 1.044 | 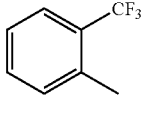 | 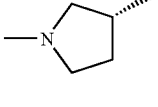 | 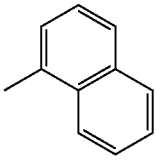 | 2HCl | MS·APCI: 385 [M + H]+ |
| 1.045 | 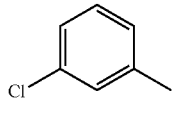 | 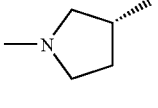 | 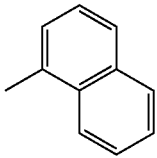 | 2HCl | MS·APCI: 351 [M + H]+ |
| 1.046 | 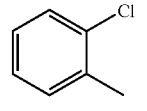 | 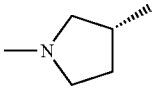 | 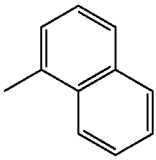 | 2HCl | MS·APCI: 351 [M + H]+ |
| 1.047 | 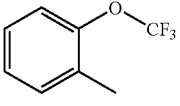 | 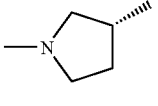 | 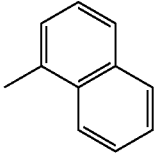 | 2HCl | MS·APCI: 401 [M + H]+ |
| 1.048 | 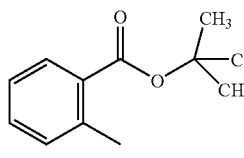 | 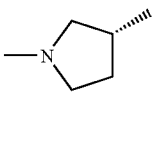 | 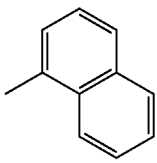 | Free form | MS·APCI: 417 [M + H]+ |

TABLE A1-continued
| Example No. | R¹—X— | —N((CH₂)ₙ)— | —Ar | Salt | Physical properties, etc. |
|---|---|---|---|---|---|
| 1.049 | 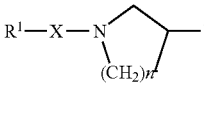 | 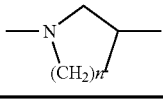 | 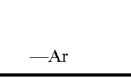 | 2HCl | MS · APCI: 318 [M + H]+ |
| 1.050 | 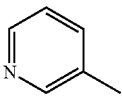 | 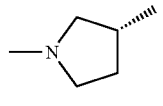 | 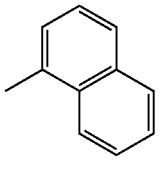 | 2HCl | MS · APCI: 318 [M + H]+ |
| 1.051 | 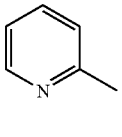 | 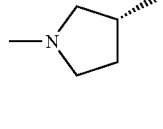 | 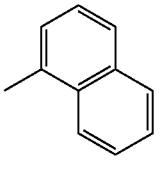 | 2HCl | MS · APCI: 343 [M + H]+ |
| 1.052 | 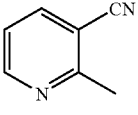 | 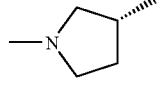 | 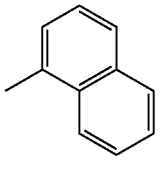 | 2HCl | MS · APCI: 332 [M + H]+ |
| 1.053 | 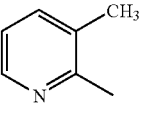 | 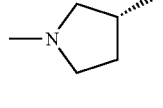 | 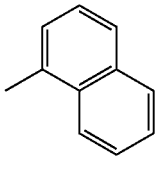 | 2HCl | MS · APCI: 332 [M + H]+ |
| 1.054 | 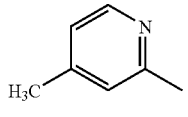 | 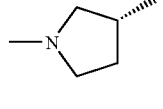 | 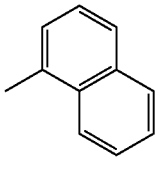 | 2HCl | MS · APCI: 332 [M + H]+ |
| 1.055 | 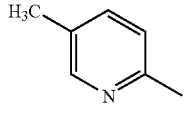 | 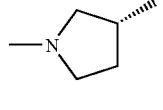 | 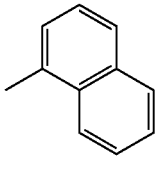 | 2HCl | MS · APCI: 352 [M + H]+ |
| 1.056 | 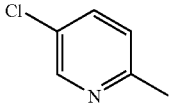 | 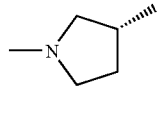 | 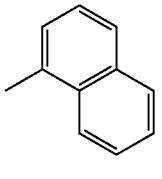 | 2HCl | MS · APCI: 386 [M + H]+ |

TABLE A1-continued
| Example No. | R¹—X— | —N(CH₂)ₙ— | —Ar | Salt | Physical properties, etc. |
|---|---|---|---|---|---|
| 1.057 | 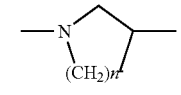 | 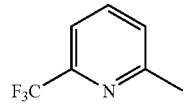 | 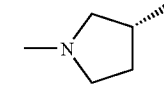 | 2HCl | MS·APCI: 386 [M + H]+ |
| 1.058 | 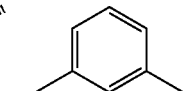 | 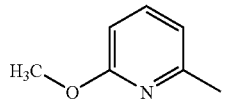 | 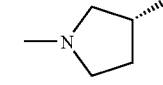 | 2HCl | MS·APCI: 348 [M + H]+ |
| 1.059 | 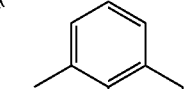 | 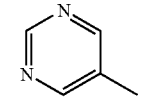 | 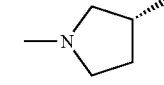 | 2HCl | MS·APCI: 319 [M + H]+ |
| 1.060 | 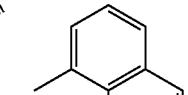 | 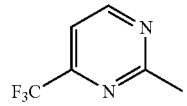 | 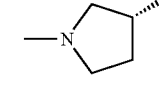 | 2HCl | MS·APCI: 387 [M + H]+ |
| 1.061 | 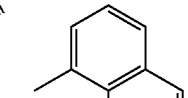 | 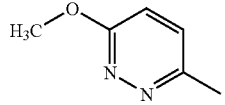 | 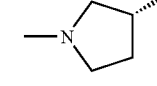 | 2HCl | MS·APCI: 349 [M + H]+ |
| 1.062 | 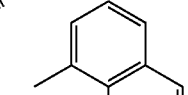 | 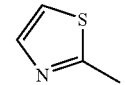 | 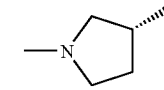 | 2HCl | MS·APCI: 324 [M + H]+ |
| 1.063 | 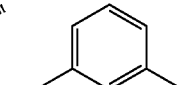 | 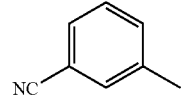 | 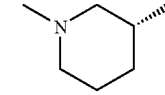 | 2HCl | MS·APCI: 356 [M + H]+ |

TABLE A1-continued

| Example No. | R¹—X— | (structure with N-(CH₂)ₙ) | —Ar | Salt | Physical properties, etc. |
|---|---|---|---|---|---|
| 1.064 | 4-NC-C₆H₄- | N-methylpiperidin-3-yl | 1-naphthyl | 2HCl | MS·APCI: 356 [M + H]+ |
| 1.065 | 2-NC-C₆H₄- | N-methylpiperidin-3-yl | 1-naphthyl | 2HCl | MS·APCI: 356 [M + H]+ |
| 1.066 | 2-CH₃-C₆H₄- | N-methylpiperidin-3-yl | 1-naphthyl | 2HCl | MS·APCI: 345 [M + H]+ |
| 1.067 | 3-CH₃-C₆H₄- | N-methylpiperidin-3-yl | 1-naphthyl | 2HCl | MS·APCI: 345 [M + H]+ |
| 1.068 | 4-CH₃-C₆H₄- | N-methylpiperidin-3-yl | 1-naphthyl | 2HCl | MS·APCI: 345 [M + H]+ |
| 1.069 | 4-Cl-C₆H₄- | N-methylpiperidin-3-yl | 1-naphthyl | 2HCl | MS·APCI: 365 [M + H]+ |
| 1.070 | 2-Cl-C₆H₄- | N-methylpiperidin-3-yl | 1-naphthyl | 2HCl | MS·APCI: 365 [M + H]+ |

TABLE A1-continued

| Example No. | R¹—X— | (CH₂)n' with N | —Ar | Salt | Physical properties, etc. |
|---|---|---|---|---|---|
| 1.071 | 3-Cl-phenyl | N-methylpiperidin-3-yl | 1-naphthyl | 2HCl | MS·APCI: 365 [M + H]+ |
| 1.072 | 2-CF₃-phenyl | N-methylpiperidin-3-yl | 1-naphthyl | 2HCl | MS·APCI: 399 [M + H]+ |
| 1.073 | 4-CF₃-phenyl | N-methylpiperidin-3-yl | 1-naphthyl | 2HCl | MS·APCI: 399 [M + H]+ |
| 1.074 | 2-OCF₃-phenyl | N-methylpiperidin-3-yl | 1-naphthyl | 2HCl | MS·APCI: 415 [M + H]+ |
| 1.075 | 4-OCF₃-phenyl | N-methylpiperidin-3-yl | 1-naphthyl | 2HCl | MS·APCI: 415 [M + H]+ |
| 1.076 | pyridin-3-yl | N-methylpiperidin-3-yl | 1-naphthyl | 2HCl | MS·APCI: 332 [M + H]+ |
| 1.077 | pyridin-2-yl | N-methylpiperidin-3-yl | 1-naphthyl | 2HCl | MS·APCI: 332 [M + H]+ |

TABLE A1-continued

| Example No. | R¹—X— | —N(CH₂)ₙ ring | —Ar | Salt | Physical properties, etc. |
|---|---|---|---|---|---|
| 1.078 | 2-methyl-3-methylpyridin-yl | 1-methylpiperidin-3-yl | naphthalen-1-yl | 2HCl | MS·APCI: 346 [M + H]+ |
| 1.079 | 5-methyl-6-methylpyridin-yl | 1-methylpiperidin-3-yl | naphthalen-1-yl | 2HCl | MS·APCI: 346 [M + H]+ |
| 1.080 | 2,6-dimethylpyridin-yl | 1-methylpiperidin-3-yl | naphthalen-1-yl | 2HCl | MS·APCI: 346 [M + H]+ |
| 1.081 | pyrimidin-5-yl | 1-methylpiperidin-3-yl | naphthalen-1-yl | 2HCl | MS·APCI: 333 [M + H]+ |
| 1.082 | 4-acetylphenyl | 1-methylpyrrolidin-3-yl | naphthalen-1-yl | HCl | MS·APCI: 359 [M + H]+ |
| 1.083 | 5-methyl-1-oxoindan-yl | 1-methylpyrrolidin-3-yl | naphthalen-1-yl | HCl | MS·APCI: 371 [M + H]+ |

TABLE A2

| Example No. | R¹—X— | —N(CH₂)ₙ (ring) | —Ar | Salt | Physical properties, etc. |
|---|---|---|---|---|---|
| 2.001 | 3-chloro-2-methylpyrazin-yl | (3R)-1-methylpyrrolidin-3-yl | 1-methylnaphthalen-yl | 2HCl | MS · APCI: 353 [M + H]+ |
| 2.002 | 6-chloro-2-methylpyridin-yl | (3R)-1-methylpyrrolidin-3-yl | 1-methylnaphthalen-yl | 2HCl | MS · APCI: 352 [M + H]+ |
| 2.003 | 6-chloro-2-methylpyrazin-yl | (3R)-1-methylpyrrolidin-3-yl | 1-methylnaphthalen-yl | 2HCl | MS · APCI: 353 [M + H]+ |
| 2.004 | 3-cyano-2-methylpyrazin-yl | (3R)-1-methylpyrrolidin-3-yl | 1-methylnaphthalen-yl | 2HCl | MS · APCI: 344 [M + H]+ |
| 2.005 | 5-trifluoromethyl-2-methylpyridin-yl | (3R)-1-methylpiperidin-3-yl | 1-methylnaphthalen-yl | 2HCl | MS · APCI: 400 [M + H]+ |
| 2.006 | 4-trifluoromethyl-2-methylpyridin-yl | (3R)-1-methylpiperidin-3-yl | 1-methylnaphthalen-yl | 2HCl | MS · APCI: 400 [M + H]+ |
| 2.007 | 3-cyano-2-methylpyridin-yl | (3R)-1-methylpiperidin-3-yl | 1-methylnaphthalen-yl | 2HCl | MS · APCI: 357 [M + H]+ |
| 2.008 | 4-trifluoromethyl-2-methylpyrimidin-yl | (3R)-1-methylpiperidin-3-yl | 1-methylnaphthalen-yl | 2HCl | MS · APCI: 401 [M + H]+ |

TABLE A2-continued
| Example No. | R¹—X— | 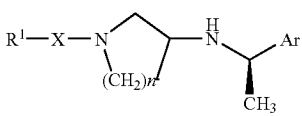—(CH₂)ₙ | —Ar | Salt | Physical properties, etc. |
|---|---|---|---|---|---|
| 2.009 | 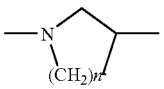 | 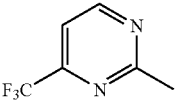 | 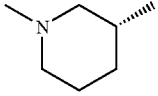 | 2HCl | MS·APCI: 358 [M + H]+ |
| 2.010 | 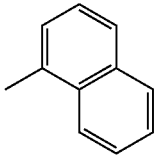 | 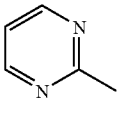 | 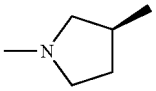 | 2HCl | MS·APCI: 319 [M + H]+ |
| 2.011 | 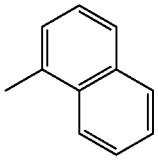 | 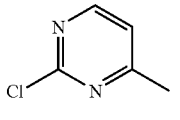 | 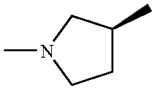 | 2HCl | MS·APCI: 353 [M + H]+ |
| 2.012 | 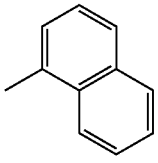 | 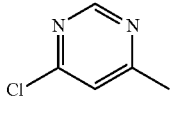 | 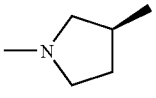 | 2HCl | MS·APCI: 353 [M + H]+ |
| 2.013 | 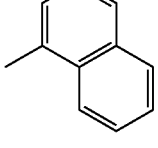 | 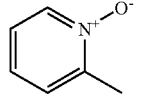 | 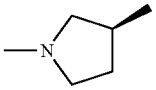 | 2HCl | MS·APCI: 318 [M + H − 16]+ |
| 2.014 | 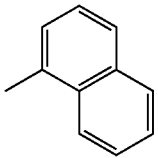 | 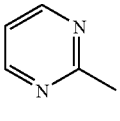 | 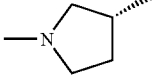 | Free form | MS·APCI: 319 [M + H]+ |
| 2.015 | 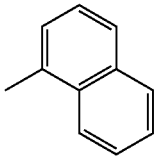 | 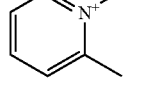 | 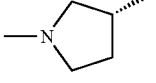 | 2HCl | MS·APCI: 318 [M + H − 16]+ |
| 2.016 | 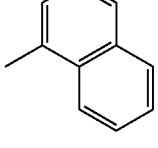 | 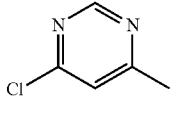 | 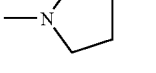 | 2HCl | MS·APCI: 353 [M + H]+ |

TABLE A2-continued

| Example No. | R¹—X— | —N(CH₂)ₙ (pyrrolidine) | —Ar | Salt | Physical properties, etc. |
|---|---|---|---|---|---|
| 2.017 | 2-chloro-4-methylpyrimidine | (3R)-3-methylpyrrolidin-1-yl | 1-methylnaphthalen-... | 2HCl | MS·APCI: 353 [M + H]+ |
| 2.018 | 4-chloro-2-methylpyrimidine | (3R)-3-methylpyrrolidin-1-yl | 1-methylnaphthalen-... | 2HCl | MS·APCI: 353 [M + H]+ |

TABLE A3

| Example No. | R¹—X— | —N(CH₂)ₙ (pyrrolidine) | —Ar | Salt | Physical properties, etc. |
|---|---|---|---|---|---|
| 3.001 | 4-methylbenzoic acid | (3R)-3-methylpyrrolidin-1-yl | 1-methylnaphthalen-... | HCl | MS·APCI: 361 [M + H]+ |
| 3.002 | 3-methylbenzoic acid | (3R)-3-methylpyrrolidin-1-yl | 1-methylnaphthalen-... | HCl | MS·APCI: 361 [M + H]+ |
| 3.003 | 3,4-dimethylbenzoic acid | (3R)-3-methylpyrrolidin-1-yl | 1-methylnaphthalen-... | HCl | MS·APCI: 375 [M + H]+ |
| 3.004 | 2,4-dimethylbenzoic acid | (3R)-3-methylpyrrolidin-1-yl | 1-methylnaphthalen-... | HCl | MS·APCI: 375 [M + H]+ |

TABLE A3-continued
| Example No. | R¹—X— | —N(CH₂)ₙ | —Ar | Salt | Physical properties, etc. |
|---|---|---|---|---|---|
| 3.005 | 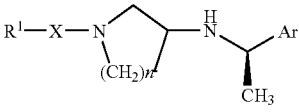 | 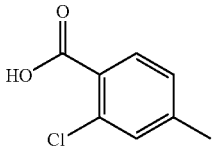 | 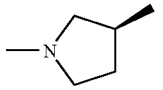 | HCl | MS · APCI: 395 [M + H]+ |
| 3.006 | 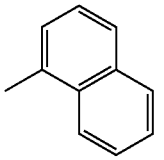 | 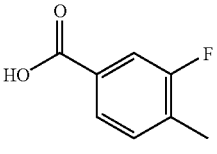 | 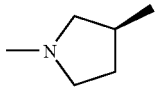 | HCl | MS · APCI: 379 [M + H]+ |
| 3.007 | 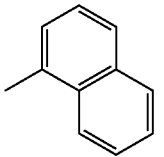 | 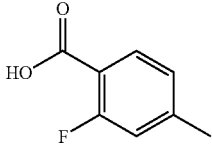 | 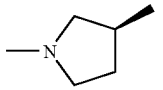 | HCl | MS · APCI: 379 [M + H]+ |
| 3.008 | 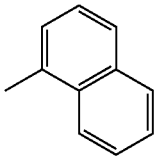 | 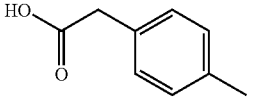 | 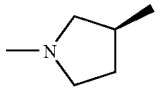 | 2HCl | MS · APCI: 375 [M + H]+ |
| 3.009 | 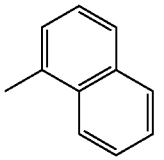 | 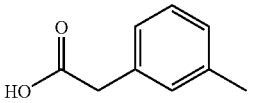 | 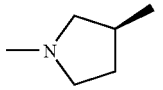 | 2HCl | MS · APCI: 375 [M + H]+ |
| 3.010 | 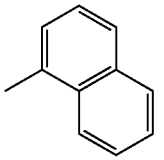 | 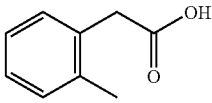 | 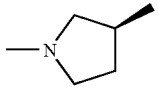 | 2HCl | MS · APCI: 375 [M + H]+ |
| 3.011 | 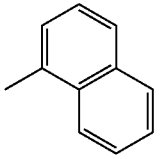 | 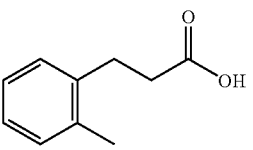 | 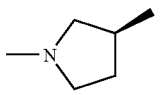 | 2HCl | MS · APCI: 389 [M + H]+ |
| 3.012 | 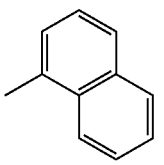 | 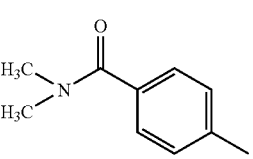 | 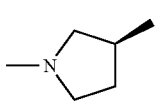 | 2HCl | MS · APCI: 388 [M + H]+ |

TABLE A3-continued
| Example No. | R¹—X— | (pyrrolidine group) | —Ar | Salt | Physical properties, etc. |
|---|---|---|---|---|---|
| 3.013 | 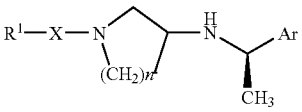 | | | Free form | MS·APCI: 416 [M + H]+ |
| 3.014 | 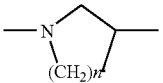 | | | 3HCl | MS·APCI: 473 [M + H]+ |
| 3.015 | 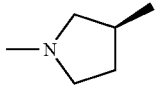 | | | 3HCl | MS·APCI: 431 [M + H]+ |
| 3.016 | 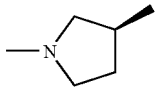 | | | Free form | MS·APCI: 474 [M + H]+ |
| 3.017 | 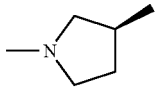 | | | 2HCl | MS·APCI: 404 [M + H]+ |
| 3.018 | 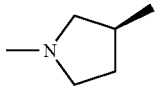 | | | 2HCl | MS·APCI: 395 (MH+) |
| 3.019 | 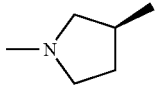 | | | 2HCl | MS·APCI: 429 [M + H]+ |
| 3.020 | 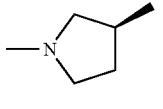 | | | 2HCl | MS·APCI: 420 [M + H]+ |

TABLE A3-continued $$R^1-X-N\underset{(CH_2)n'}{\overset{}{\bigcirc}}\overset{H}{N}\underset{CH_3}{\overset{}{\bigvee}}Ar$$

| Example No. | R¹—X— | n'⟩) | —Ar | Salt | Physical properties, etc. |
|---|---|---|---|---|---|
| 3.021 | 3-(trifluoromethoxy)phenyl-6-methylpyrimidin-4-yl | (S)-1-methyl-3-pyrrolidinyl | 1-methylnaphthalen-? | 2HCl | MS·APCI: 479 [M + H]+ |
| 3.022 | 3-methoxyphenyl-6-methylpyrimidin-4-yl | (S)-1-methyl-3-pyrrolidinyl | 1-methylnaphthalen-? | 2HCl | MS·APCI: 425 [M + H]+ |

TABLE B $$R^1-X-N\underset{(CH_2)n'}{\overset{}{\bigcirc}}\overset{H}{N}\underset{CH_3}{\overset{}{\bigvee}}Ar$$

| Example No. | R¹—X— | n'⟩) | —Ar | Salt | Physical properties, etc. |
|---|---|---|---|---|---|
| 4.001 | 3-(trifluoromethyl)benzyl | (S)-1-methylpyrrolidin-3-yl | 3-methoxyphenyl | 2HCl | MS·APCI: 379 [M + H]+ |
| 4.002 | 3-(trifluoromethyl)benzyl | (R)-1-methylpyrrolidin-3-yl | 3-methoxyphenyl | 2HCl | MS·APCI: 379 [M + H]+ |
| 4.003 | 2-chlorobenzyl | (R)-1-methylpyrrolidin-3-yl | 3-methoxyphenyl | 2HCl | MS·APCI: 345 [M + H]+ |
| 4.004 | 3-(trifluoromethoxy)benzyl | (R)-1-methylpyrrolidin-3-yl | 3-methoxyphenyl | 2HCl | MS·APCI: 395 [M + H]+ |
| 4.005 | 3-(trifluoromethyl)benzyl | (S)-1-methylpyrrolidin-3-yl | 1-methylnaphthalen-? | 2HCl | MS·APCI: 399 [M + H]+ |

TABLE B-continued
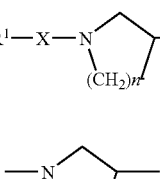
| Example No. | R¹—X— | 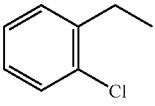 —(CH₂)ₙ— | —Ar | Salt | Physical properties, etc. |
|---|---|---|---|---|---|
| 4.006 | 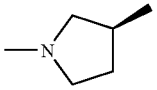 | 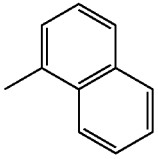 | 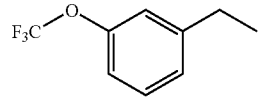 | 2HCl | MS · APCI: 365 [M + H]+ |
| 4.007 | 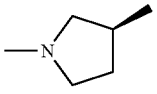 | 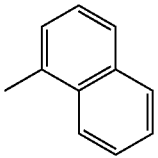 | 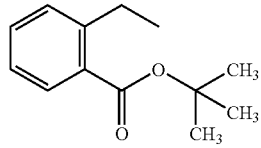 | 2HCl | MS · APCI: 415 [M + H]+ |
| 4.008 | 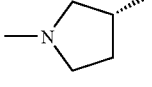 | 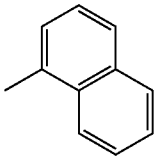 | 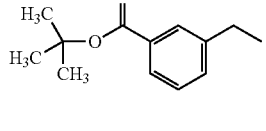 | Free form | MS · APCI: 431 [M + H]+ |
| 4.009 | 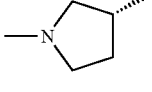 | 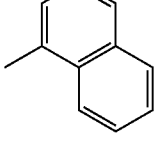 | 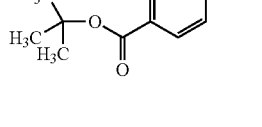 | Free form | MS · APCI: 431 [M + H]+ |
| 4.010 | 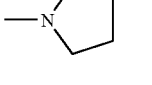 | 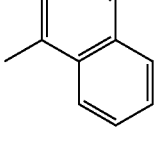 | 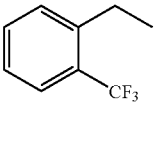 | Free form | MS · APCI: 431 [M + H]+ |
| 4.011 | 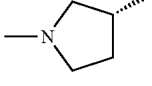 | 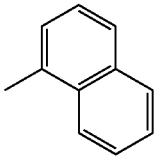 | 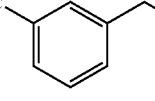 | Free form | MS · APCI: 399 [M + H]+ |
| 4.012 | 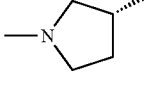 | 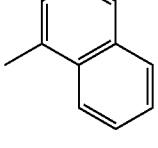 | 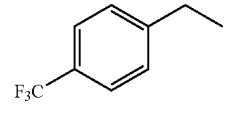 | 2HCl | MS · APCI: 399 [M + H]+ |
| 4.013 | 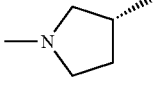 | 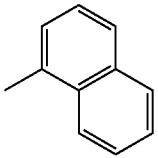 | | Free form | MS · APCI: 399 [M + H]+ |

TABLE B-continued

| Example No. | R¹—X— | —N(CH₂)n— pyrrolidine | —Ar | Salt | Physical properties, etc. |
|---|---|---|---|---|---|
| 4.014 | 2-ethyl-chlorobenzene | (3S)-methylpyrrolidine | 1-naphthyl | 2HCl | MS·APCI: 365 [M + H]+ |
| 4.015 | 3-chloro-ethylbenzene | (3S)-methylpyrrolidine | 1-naphthyl | Free form | MS·APCI: 365 [M + H]+ |
| 4.016 | 4-chloro-ethylbenzene | (3S)-methylpyrrolidine | 1-naphthyl | Free form | MS·APCI: 365 [M + H]+ |
| 4.017 | 2-fluoro-ethylbenzene | (3S)-methylpyrrolidine | 1-naphthyl | Free form | MS·APCI: 349 [M + H]+ |
| 4.018 | 3-methyl-ethylbenzene | (3S)-methylpyrrolidine | 1-naphthyl | Free form | MS·APCI: 345 [M + H]+ |
| 4.019 | 4-methyl-ethylbenzene | (3S)-methylpyrrolidine | 1-naphthyl | Free form | MS·APCI: 345 [M + H]+ |
| 4.020 | 3-cyano-ethylbenzene | (3S)-methylpyrrolidine | 1-naphthyl | Free form | MS·APCI: 356 [M + H]+ |
| 4.021 | 4-methoxy-ethylbenzene | (3S)-methylpyrrolidine | 1-naphthyl | Free form | MS·APCI: 361 [M + H]+ |

TABLE B-continued

| Example No. | R¹—X— | —N(CH₂)ₙ— | —Ar | Salt | Physical properties, etc. |
|---|---|---|---|---|---|
| 4.022 | 3-(trifluoromethoxy)phenyl-CH₂- | (3R)-3-methylpyrrolidin-1-yl-CH₂- | 1-naphthyl | 2HCl | MS·APCI: 415 [M+H]+ |
| 4.023 | 4-(dimethylamino)phenyl-CH₂- | (3R)-3-methylpyrrolidin-1-yl-CH₂- | 1-naphthyl | Free form | MS·APCI: 374 [M+H]+ |
| 4.024 | 3,5-bis(trifluoromethyl)phenyl-CH₂- | (3R)-3-methylpyrrolidin-1-yl-CH₂- | 1-naphthyl | Free form | MS·APCI: 467 [M+H]+ |
| 4.025 | cyclohexyl-CH₂- | (3R)-3-methylpyrrolidin-1-yl-CH₂- | 1-naphthyl | Free form | MS·APCI: 337 [M+H]+ |
| 4.026 | 1-methyl-1H-pyrrol-2-yl-CH₂- | (3R)-3-methylpyrrolidin-1-yl-CH₂- | 1-naphthyl | Free form | MS·APCI: 334 [M+H]+ |
| 4.027 | thiazol-2-yl-CH₂- | (3R)-3-methylpyrrolidin-1-yl-CH₂- | 1-naphthyl | Free form | MS·APCI: 338 [M+H]+ |
| 4.028 | 5-methylthiophen-2-yl-CH₂- | (3R)-3-methylpyrrolidin-1-yl-CH₂- | 1-naphthyl | Free form | MS·APCI: 351 [M+H]+ |
| 4.029 | 5-chlorothiophen-2-yl-CH₂- | (3R)-3-methylpyrrolidin-1-yl-CH₂- | 1-naphthyl | Free form | MS·APCI: 371 [M+H]+ |

TABLE B-continued
| Example No. | R¹—X— | —N(CH₂)ₙ'— | —Ar | Salt | Physical properties, etc. |
|---|---|---|---|---|---|
| 4.030 | 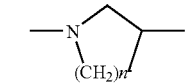 | 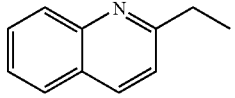 | 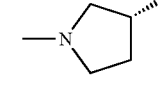 | Free form | MS·APCI: 382 [M + H]+ |
| 4.031 | 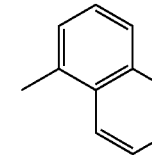 | 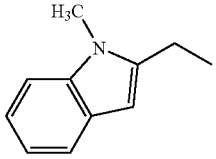 | 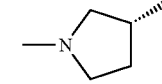 | Free form | MS·APCI: 384 [M + H]+ |
| 4.032 | 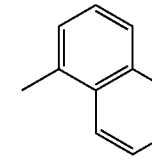 | 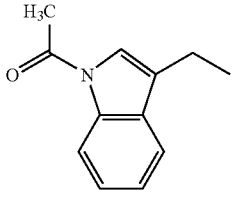 | 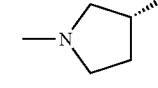 | Free form | MS·APCI: 412 [M + H]+ |
| 4.033 | 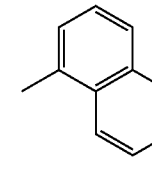 | 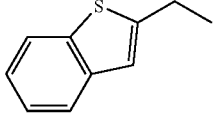 | 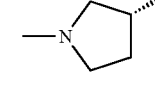 | Free form | MS·APCI: 387 [M + H]+ |
| 4.034 | 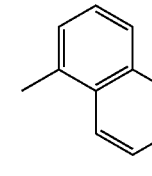 | 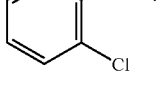 | 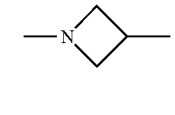 | 2HCl | MS·APCI: 351 [M + H]+ |
| 4.035 | 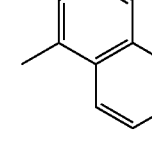 | 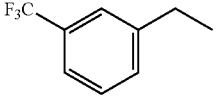 | 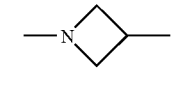 | 2HCl | MS·APCI: 385 [M + H]+ |
| 4.036 | 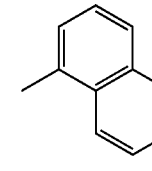 | 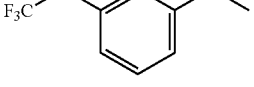 | 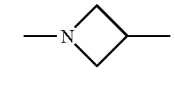 | 2HCl | MS·APCI: 401 [M + H]+ |

TABLE B-continued
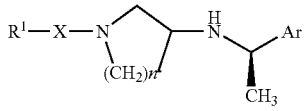
| Example No. | R¹—X— | —N(CH₂)ₙ′ | —Ar | Salt | Physical properties, etc. |
|---|---|---|---|---|---|
| 4.037 | 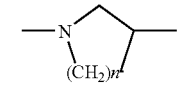 |  |  | 2HCl | MS · APCI: 413 [M + H]+ |
| 4.038 | 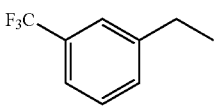 | 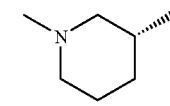 | 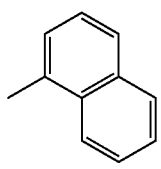 | 2HCl | MS · APCI: 429 [M + H]+ |
TABLE C
| Example No. | R¹—X— | —N(CH₂)ₙ′ | —Ar | Salt | Physical properties, etc. |
|---|---|---|---|---|---|
| 5.001 | 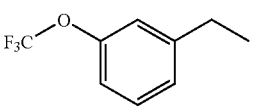 | 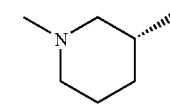 | 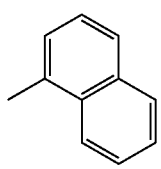 | HCl | MS · APCI: 413 [M + H]+ |
| 5.002 | 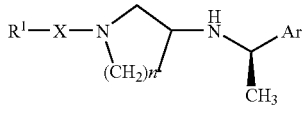 | 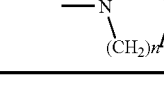 | 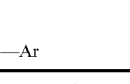 | Free form | MS · APCI: 413 [M + H]+ |
| 5.003 |  | 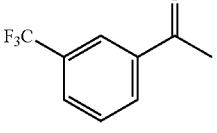 | 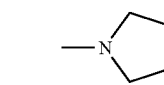 | Free form | MS · APCI: 413 [M + H]+ |
| 5.004 | 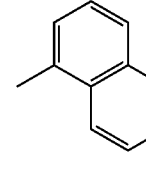 |  | 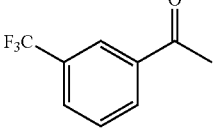 | Free form | MS · APCI: 345 [M + H]+ |

TABLE C-continued

| Example No. | R¹—X— | —N(CH₂)n— | —Ar | Salt | Physical properties, etc. |
|---|---|---|---|---|---|
| 5.005 | (2-F₃CO-phenyl)C(O)— | N-methylpyrrolidin-3-yl | 1-methylnaphthyl | HCl | MS·APCI: 429 [M + H]+ |
| 5.006 | (2-F₃CO-phenyl)C(O)— | N-methylpyrrolidin-3-yl | 1-methylnaphthyl | HCl | MS·APCI: 429 [M + H]+ |
| 5.007 | (3-F₃CO-phenyl)C(O)— | N-methylpyrrolidin-3-yl | 1-methylnaphthyl | HCl | MS·APCI: 429 [M + H]+ |
| 5.008 | (4-F₃CO-phenyl)C(O)— | N-methylpyrrolidin-3-yl | 1-methylnaphthyl | HCl | MS·APCI: 429 [M + H]+ |
| 5.009 | (3,4-diCl-phenyl)C(O)— | N-methylpyrrolidin-3-yl | 1-methylnaphthyl | Free form | MS·APCI: 413 [M + H]+ |
| 5.010 | (4-methylpiperazin-1-yl)C(O)— | N-methylpyrrolidin-3-yl | 1-methylnaphthyl | Free form | MS·APCI: 367 [M + H]+ |
| 5.011 | (diphenylmethyl)C(O)— | N-methylpyrrolidin-3-yl | 1-methylnaphthyl | Free form | MS·APCI: 435 [M + H]+ |

TABLE C-continued
| Example No. | R¹—X— | —N(CH₂)ₙ' | —Ar | Salt | Physical properties, etc. |
|---|---|---|---|---|---|
| 5.012 | 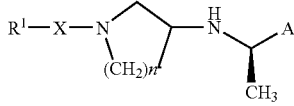 | 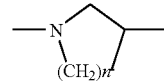 |  | HCl | MS · APCI: 361 [M + H]+ |
| 5.013 | 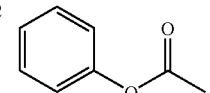 | 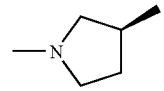 | 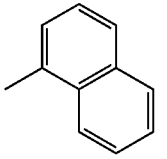 | HCl | MS · APCI: 391 [M + H]+ |
| 5.014 | 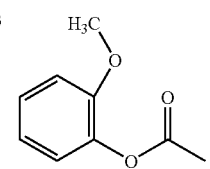 | 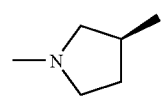 | 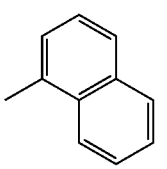 | HCl | MS · APCI: 375 [M + H]+ |
| 5.015 | 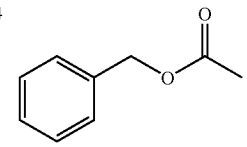 | 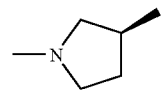 | 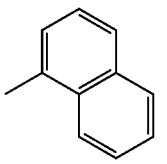 | HCl | MS · APCI: 375 [M + H]+ |
| 5.016 | 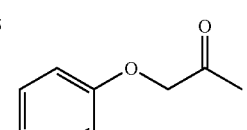 | 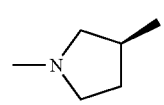 | 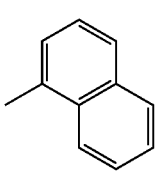 | Free form | MS · APCI: 374 [M + H]+ |
| 5.017 | 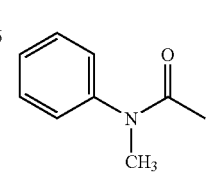 | 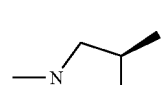 | 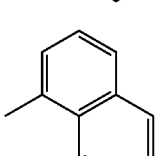 | Free form | MS · APCI: 427 [M + H]+ |
| 5.018 | 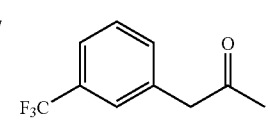 | 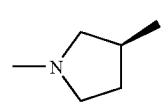 | 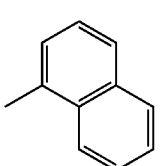 | 2HCl | MS · APCI: 410 [M + H]+ |
| 5.019 | 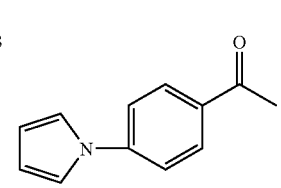 | 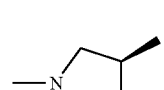 | 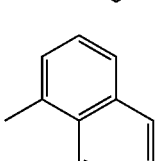 | 2HCl | MS · APCI: 348 [M + H]+ |

TABLE C-continued
| Example No. | R¹—X— | —N(CH₂)n— | —Ar | Salt | Physical properties, etc. |
|---|---|---|---|---|---|
| 5.020 | 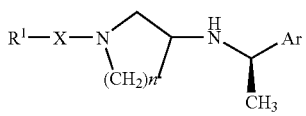 | 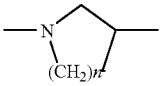 | 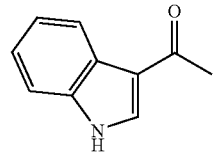 | 2HCl | MS · APCI: 384 [M + H]+ |
| 5.021 | 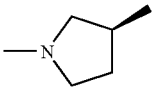 | 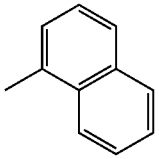 | 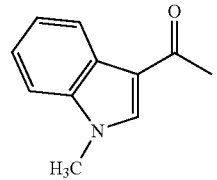 | 2HCl | MS · APCI: 398 [M + H]+ |
| 5.022 | 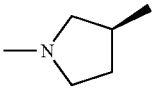 | 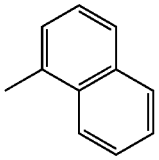 | 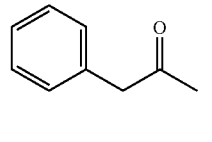 | Free form | MS · APCI: 359 [M + H]+ |
| 5.023 | 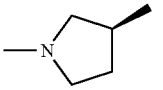 | 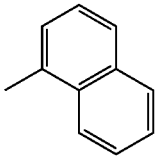 | 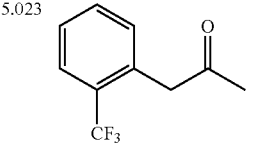 | HCl | MS · APCI: 427 [M + H]+ |
| 5.024 | 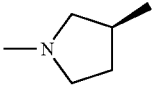 | 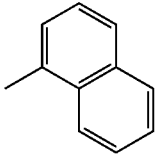 | 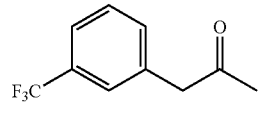 | HCl | MS · APCI: 427 [M + H]+ |
| 5.025 | 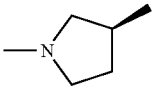 | 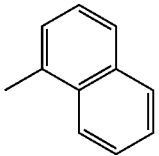 | 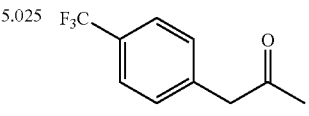 | Free form | MS · APCI: 427 [M + H]+ |
| 5.026 | 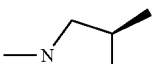 | 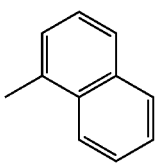 | 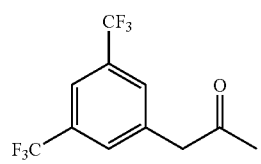 | HCl | MS · APCI: 495 [M + H]+ |
| 5.027 | 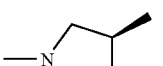 | 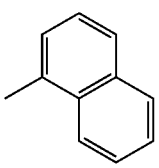 | 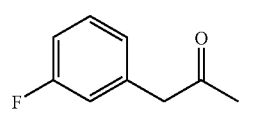 | HCl | MS · APCI: 377 [M + H]+ |

TABLE C-continued

| Example No. | R¹—X— | —N(CH₂)ₙ— | —Ar | Salt | Physical properties, etc. |
|---|---|---|---|---|---|
| 5.028 | 2-F-C₆H₄-CH₂-C(O)- | 3-methylpyrrolidin-1-yl | 1-naphthyl | HCl | MS·APCI: 377 [M + H]+ |
| 5.029 | 4-F-C₆H₄-CH₂-C(O)- | 3-methylpyrrolidin-1-yl | 1-naphthyl | Free form | MS·APCI: 377 [M + H]+ |
| 5.030 | 3,4-diF-C₆H₃-CH₂-C(O)- | 3-methylpyrrolidin-1-yl | 1-naphthyl | HCl | MS·APCI: 395 [M + H]+ |
| 5.031 | 2-Cl-C₆H₄-CH₂-C(O)- | 3-methylpyrrolidin-1-yl | 1-naphthyl | HCl | MS·APCI: 393 [M + H]+ |
| 5.032 | 3-Cl-C₆H₄-CH₂-C(O)- | 3-methylpyrrolidin-1-yl | 1-naphthyl | HCl | MS·APCI: 393 [M + H]+ |
| 5.033 | 4-Cl-C₆H₄-CH₂-C(O)- | 3-methylpyrrolidin-1-yl | 1-naphthyl | HCl | MS·APCI: 393 [M + H]+ |
| 5.034 | 3,4-diCl-C₆H₃-CH₂-C(O)- | 3-methylpyrrolidin-1-yl | 1-naphthyl | HCl | MS·APCI: 427 [M + H]+ |
| 5.035 | 4-CH₃-C₆H₄-CH₂-C(O)- | 3-methylpyrrolidin-1-yl | 1-naphthyl | HCl | MS·APCI: 373 [M + H]+ |

TABLE C-continued

| Example No. | R¹—X— | —N(CH₂)ₙ— (pyrrolidine) | —Ar | Salt | Physical properties, etc. |
|---|---|---|---|---|---|
| 5.036 | 4-methoxyphenylacetone | 3-methylpyrrolidin-1-yl | 1-naphthyl | HCl | MS·APCI: 389 [M + H]+ |
| 5.037 | 2-thienylacetone | 3-methylpyrrolidin-1-yl | 1-naphthyl | Free form | MS·APCI: 365 [M + H]+ |
| 5.038 | 2-thienylacetone | 3-methylpyrrolidin-1-yl | 1-naphthyl | HCl | MS·APCI: 365 [M + H]+ |
| 5.039 | 3-thienylacetone | 3-methylpyrrolidin-1-yl | 1-naphthyl | HCl | MS·APCI: 365 [M + H]+ |
| 5.040 | 1-methylindol-3-ylacetone | 3-methylpyrrolidin-1-yl | 1-naphthyl | 2HCl | MS·APCI: 412 [M + H]+ |
| 5.041 | indol-3-ylacetone | 3-methylpyrrolidin-1-yl | 1-naphthyl | 2HCl | MS·APCI: 398 [M + H]+ |
| 5.042 | benzimidazol-1-ylacetone | 3-methylpyrrolidin-1-yl | 1-naphthyl | 2HCl | MS·APCI: 399 [M + H]+ |
| 5.043 | benzotriazol-2-ylacetone | 3-methylpyrrolidin-1-yl | 1-naphthyl | HCl | MS·APCI: 400 [M + H]+ |

TABLE C-continued

| Example No. | R¹—X— | —N(CH₂)ₙ— | —Ar | Salt | Physical properties, etc. |
|---|---|---|---|---|---|
| 5.044 | benzothiophen-3-yl-CH₂-C(O)- | N-methylpyrrolidin-3-yl | 1-naphthyl | HCl | MS·APCI: 415 [M + H]+ |
| 5.045 | 3-oxo-2H-benzo[b][1,4]thiazin-4(3H)-yl-CH₂-C(O)- | N-methylpyrrolidin-3-yl | 1-naphthyl | HCl | MS·APCI: 446 [M + H]+ |
| 5.046 | 4-methyl-1-oxophthalazin-2(1H)-yl-CH₂-C(O)- | N-methylpyrrolidin-3-yl | 1-naphthyl | HCl | MS·APCI: 441 [M + H]+ |
| 5.047 | 2-F-C₆H₄-CH₂CH₂-C(O)- | N-methylpyrrolidin-3-yl | 1-naphthyl | HCl | MS·APCI: 391 [M + H]+ |
| 5.048 | 3-F-C₆H₄-CH₂CH₂-C(O)- | N-methylpyrrolidin-3-yl | 1-naphthyl | HCl | MS·APCI: 391 [M + H]+ |
| 5.049 | 4-F-C₆H₄-CH₂CH₂-C(O)- | N-methylpyrrolidin-3-yl | 1-naphthyl | HCl | MS·APCI: 391 [M + H]+ |
| 5.050 | 3-CF₃-C₆H₄-CH₂CH₂-C(O)- | N-methylpyrrolidin-3-yl | 1-naphthyl | HCl | MS·APCI: 441 [M + H]+ |

TABLE C-continued
| Example No. | R¹—X— | —N(CH₂)n'— (pyrrolidine) | —Ar | Salt | Physical properties, etc. |
|---|---|---|---|---|---|
| 5.051 | 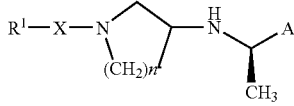 | 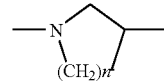 | 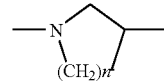 | HCl | MS · APCI: 457 [M + H]+ |
| 5.052 |  | 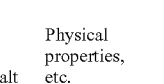 | 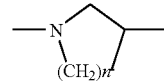 | 2HCl | MS · APCI: 412 [M + H]+ |
| 5.053 |  | 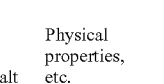 | 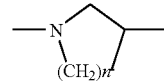 | HCl | MS · APCI: 387 [M + H]+ |
| 5.054 |  | 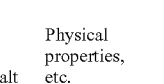 | 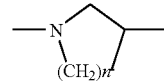 | HCl | MS · APCI: 389 [M + H]+ |
| 5.055 |  | 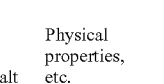 | 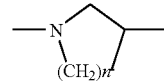 | HCl | MS · APCI: 437 [M + H]+ |
| 5.056 |  | 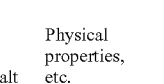 | 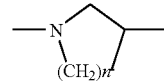 | HCl | MS · APCI: 457 [M + H]+ |
| 6.001 |  | 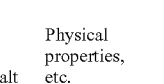 | 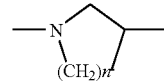 | Free form | MS · APCI: 428 [M + H]+ |
| 6.002 |  | 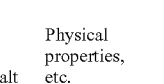 | 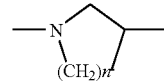 | Free form | MS · APCI: 428 [M + H]+ |

TABLE EF

| Example No. | R¹—X— | (with N-CH₃, (CH₂)ₙ) | —Ar | Salt | Physical properties, etc. |
|---|---|---|---|---|---|
| 7.001 (a) | F₃C-O-(3-phenyl)- | N-methylpiperidin-3-yl (wedge) | 1-naphthyl | 2HCl | MS·APCI: 415 [M+H]+ |
| 7.001 (b) | F₃C-O-(3-phenyl)- | N-methylpiperidin-3-yl (dash) | 1-naphthyl | 2HCl | MS·APCI: 415 [M+H]+ |
| 7.002 | F₃C-O-(3-phenyl)- | N-methylpiperidin-3-yl (wedge) | 3-MeO-phenyl | Free form | MS·APCI: 395 [M+H]+ |
| 7.003 | F₃C-O-(3-phenyl)- | N-methylpiperidin-3-yl (dash) | 3-MeO-phenyl | Free form | MS·APCI: 395 [M+H]+ |
| 7.004 | F₃C-(3-phenyl)- | N-methylpiperidin-3-yl (dash) | 1-naphthyl | 2HCl | MS·APCI: 399 [M+H]+ |
| 7.005 | F₃C-O-(3-phenyl)- | N-methylpyrrolidin-3-yl | 1-naphthyl | Free form | MS·APCI: 401 [M+H]+ |
| 7.006 | F₃C-(3-phenyl)- | N-methylpyrrolidin-3-yl | 1-naphthyl | Free form | MS·APCI: 385 [M+H]+ |
| 7.007 | F₃C-O-(3-phenyl)- | N-methylpyrrolidin-3-yl | 3-MeO-phenyl | Free form | MS·APCI: 381 [M+H]+ |
| 8.001 | F₃C-(3-phenyl)-CH₂- | N-methylpyrrolidin-3-yl | 1-naphthyl | Free form | MS·APCI: 399 [M+H]+ |

TABLE EF-continued
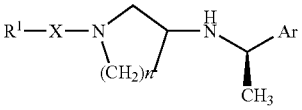
| Example No. | R¹—X— | —N(CH₂)ₙ | —Ar | Salt | Physical properties, etc. |
|---|---|---|---|---|---|
| 8.002 | 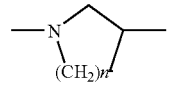 | 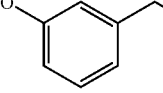 |  | Free form | MS·APCI: 415 [M + H]+ |
| 8.003 | 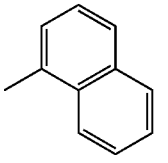 | 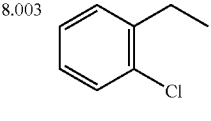 |  | Free form | MS·APCI: 365 [M + H]+ |
| 8.004 | 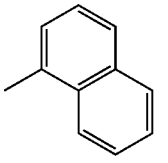 | 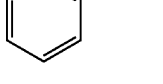 |  | Free form | MS·APCI: 379 [M + H]+ |
| 8.005 | 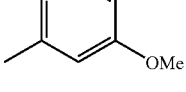 | 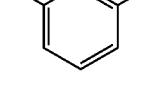 |  | Free form | MS·APCI: 395 [M + H]+ |
| 8.006 | 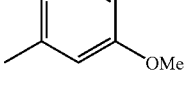 | 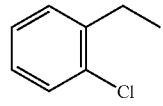 |  | Free form | MS·APCI: 345 [M + H]+ |
| 8.007 | 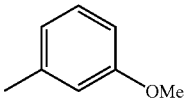 |  |  | Free form | MS·APCI: 429 [M + H]+ |
| 8.008 | 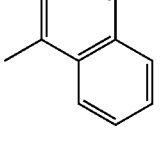 | 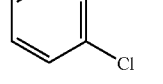 |  | Free form | MS·APCI: 379 [M + H]+ |
| 8.009 | 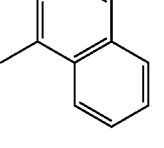 | 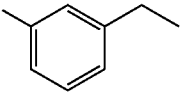 |  | Free form | MS·APCI: 393 [M + H]+ |
| 8.010 | 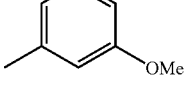 | 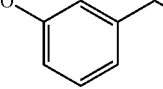 |  | Free form | MS·APCI: 409 [M + H]+ |

TABLE EF-continued
| Example No. | R$^1$—X— | 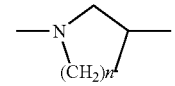 | —Ar | Salt | Physical properties, etc. |
|---|---|---|---|---|---|
| 8.011 | 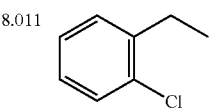 | 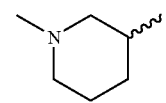 | 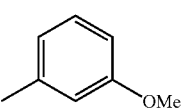 | Free form | MS · APCI: 359 [M + H]+ |
TABLE X
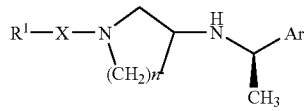
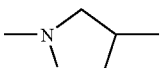
| Example No. | R$^1$—X— | | —Ar | Salt | Physical properties, etc. |
|---|---|---|---|---|---|
| 9.001 |  | 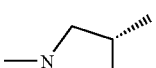 | 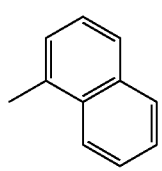 | HCl | MS · ESI: 413 [M + H]+ |
| 9.002 | 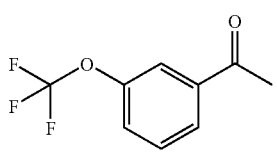 | 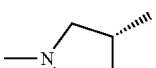 | 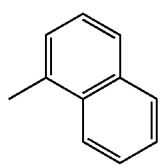 | HCl | MS · ESI: 429 [M + H]+ |
| 9.003 | 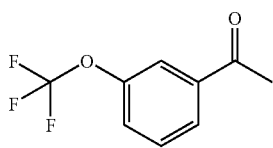 |  | 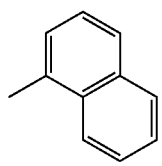 | Free form | MS · ESI: 415 [M + H]+ |
| 9.004 | 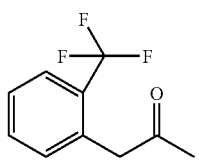 | 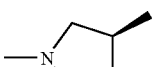 | 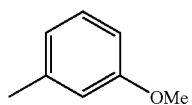 | HCl | MS · APCI: 407 [M + H]+ |
| 9.005 | 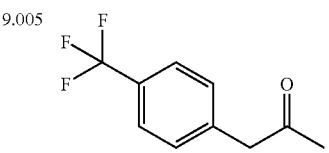 | 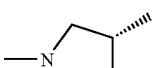 | 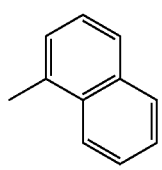 | HCl | MS · ESI: 427 [M + H]+ |

TABLE X-continued
| Example No. | R¹—X— | (structure) | —Ar | Salt | Physical properties, etc. |
|---|---|---|---|---|---|
| 9.006 | 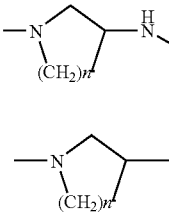 | 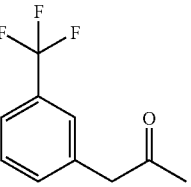 | 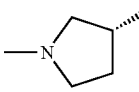 | HCl | MS·ESI: 427 [M + H]+ |
| 9.007 | 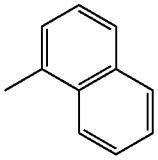 | 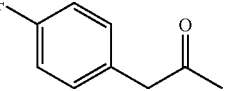 |  | HCl | MS·ESI: 377 [M + H]+ |
| 9.008 | 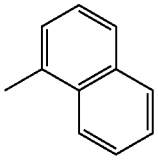 | 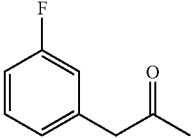 | 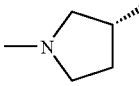 | HCl | MS·ESI: 377 [M + H]+ |
| 9.009 | 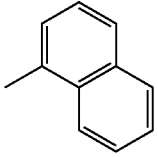 | 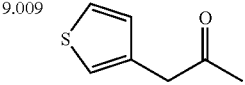 | 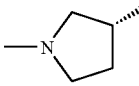 | HCl | MS·ESI: 365 [M + H]+ |
| 9.010 | 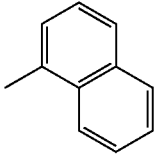 | 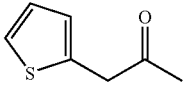 | 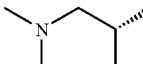 | HCl | MS·ESI: 379 [M + H]+ |
| 9.011 | 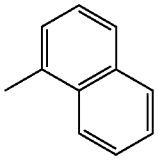 | 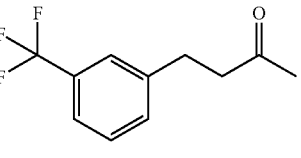 | 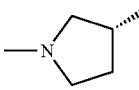 | HCl | MS·ESI: 441 [M + H]+ |
| 9.012 | 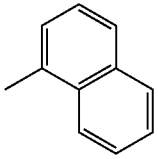 | 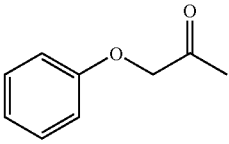 | 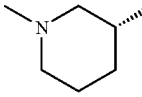 | HCl | MS·ESI: 389 [M + H]+ |
| 9.013 | 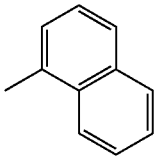 | 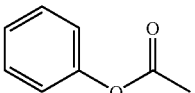 | 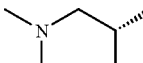 | HCl | MS·ESI: 375 [M + H]+ |

TABLE X-continued

| Example No. | R¹—X— | (pyrrolidine/piperidine) | —Ar | Salt | Physical properties, etc. |
|---|---|---|---|---|---|
| 9.014 | benzyl acetate | N-methyl-3-methylpiperidine | 1-naphthyl | HCl | MS·ESI: 389 [M+H]+ |
| 9.015 | N-methyl-N-phenylacetamide | N-methyl-3-methylpyrrolidine | 1-naphthyl | HCl | MS·ESI: 374 [M+H]+ |
| 10.001 | 4-methylphenylacetonitrile | N-methyl-3-methylpyrrolidine | 1-naphthyl | HCl | MS·APCI: 356 [M+H]+ |
| 10.002 | 1-(4-methylphenyl)propan-1-one | N-methyl-3-methylpyrrolidine | 1-naphthyl | 2HCl | MS·APCI: 373 [M+H]+ |
| 10.003 | 1-(4-methylphenyl)propan-1-one | N-methyl-3-methylpyrrolidine | 1-naphthyl | 2HCl | MS·APCI: 373 [M+H]+ |
| 10.004 | 1-(4-methylphenyl)ethan-1-one | N-methyl-3-methylpyrrolidine | 1-naphthyl | 2HCl | MS·APCI: 359 [M+H]+ |
| 10.005 | cyclopropyl(4-methylphenyl)methanone | N-methyl-3-methylpyrrolidine | 1-naphthyl | 2HCl | MS·APCI: 385 [M+H]+ |
| 10.006 | 1-methyl-4-(methylsulfonyl)benzene | N-methyl-3-methylpyrrolidine | 1-naphthyl | 2HCl | MS·APCI: 395 [M+H]+ |

TABLE X-continued

| Example No. | R¹—X— | —N(pyrrolidine)(CH₂)ₙ | —Ar | Salt | Physical properties, etc. |
|---|---|---|---|---|---|
| 10.007 | 3-methylphenyl-SO₂-(CH₃) | (S)-1,3-dimethylpyrrolidin-3-yl | 1-methylnaphthalen-? | HCl | MS·APCI: 395 [M + H]+ |
| 11.001 | 4-methylbenzoyl (HO-C(O)-) | (S)-1,3-dimethylpyrrolidin-3-yl | 3-methoxyphenyl (OMe) | Free form | MS·APCI: 341 [M + H]+ |
| 11.002 | 3-(4-methylphenyl)propanoyl | (S)-1,3-dimethylpyrrolidin-3-yl | 1-methylnaphthalenyl | Free form | MS·APCI: 389 [M + H]+ |
| 11.003 | 3-(3-methylphenyl)propanoyl | (S)-1,3-dimethylpyrrolidin-3-yl | 1-methylnaphthalenyl | Free form | MS·APCI: 389 [M + H]+ |
| 11.004 | 3-(3-methylphenyl)propanoyl | (R)-1,3-dimethylpyrrolidin-3-yl | 1-methylnaphthalenyl | Free form | MS·APCI: 389 [M + H]+ |
| 11.005 | 4-methylbenzamide (H₂N-C(O)-) | (S)-1,3-dimethylpyrrolidin-3-yl | 1-methylnaphthalenyl | 2HCl | MS·ESI: 360 [M + H]+ |
| 11.006 | N-ethyl-4-methylbenzamide | (S)-1,3-dimethylpyrrolidin-3-yl | 1-methylnaphthalenyl | 2HCl | MS·ESI: 388 [M + H]+ |
| 11.007 | N-(cyclopropylmethyl)-4-methylbenzamide | (S)-1,3-dimethylpyrrolidin-3-yl | 1-methylnaphthalenyl | 2HCl | MS·ESI: 414 [M + H]+ |

TABLE X-continued

| Example No. | R¹—X— | —N(CH₂)ₙ | —Ar | Salt | Physical properties, etc. |
|---|---|---|---|---|---|
| 11.008 | isopropyl-NH-C(O)-C₆H₄-CH₃ (para) | N-methylpyrrolidin-3-yl | 1-naphthyl | 2HCl | MS·ESI: 402 [M + H]+ |
| 11.009 | tert-butyl-NH-C(O)-C₆H₄-CH₃ (meta) | N-methylpyrrolidin-3-yl | 1-naphthyl | 2HCl | MS·ESI: 416 [M + H]+ |
| 11.010 | CF₃CH₂-NH-C(O)-C₆H₄-CH₃ (para) | N-methylpyrrolidin-3-yl | 1-naphthyl | 2HCl | MS·ESI: 442 [M + H]+ |
| 11.011 | CH₃O(CH₂)₃-NH-C(O)-C₆H₄-CH₃ (para) | N-methylpyrrolidin-3-yl | 1-naphthyl | 2HCl | MS·ESI: 432 [M + H]+ |
| 11.012 | CH₃CH₂O(CH₂)₂-NH-C(O)-C₆H₄-CH₃ (para) | N-methylpyrrolidin-3-yl | 1-naphthyl | 2HCl | MS·ESI: 432 [M + H]+ |
| 11.013 | CH₃CH₂O(CH₂)₃-NH-C(O)-C₆H₄-CH₃ (para) | N-methylpyrrolidin-3-yl | 1-naphthyl | 2HCl | MS·ESI: 446 [M + H]+ |
| 11.014 | (CH₃)₂CHO(CH₂)₃-NH-C(O)-C₆H₄-CH₃ (para) | N-methylpyrrolidin-3-yl | 1-naphthyl | 2HCl | MS·ESI: 460 [M + H]+ |

TABLE X-continued
| Example No. | R¹—X— | —N(CH₂)ₙ— | —Ar | Salt | Physical properties, etc. |
|---|---|---|---|---|---|
| 11.015 | 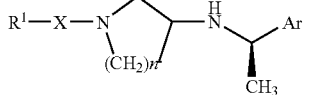 | 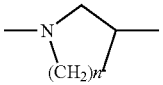 | 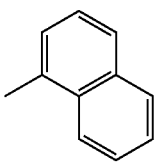 | 2HCl | MS·APCI: 418 [M + H]+ |
| 11.016 | 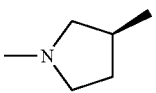 | 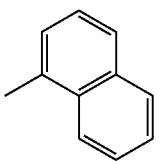 | 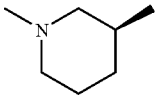 | 2HCl | MS·ESI: 418 [M + H]+ |
| 11.017 | 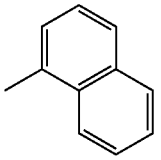 | 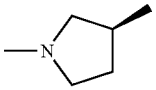 | 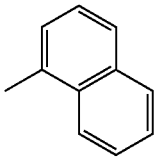 | 2HCl | MS·APCI: 418 [M + H]+ |
| 11.018 |  | 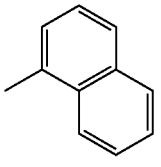 | 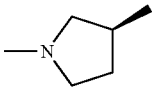 | 2HCl | MS·APCI: 418 [M + H]+ |
| 11.019 | 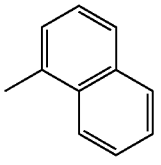 | 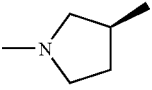 | 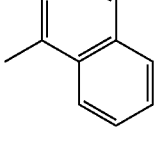 | 2HCl | MS·APCI: 432 [M + H]+ |
| 11.020 | | | | Free form | MS·APCI: 432 [M + H]+ |
| 11.021 | | | | Free form | MS·APCI: 458 [M + H]+ |

TABLE X-continued
| Example No. | R¹—X— | —N(CH₂)ₙ ring | —Ar | Salt | Physical properties, etc. |
|---|---|---|---|---|---|
| 11.022 | 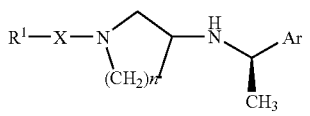 | 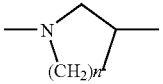 | 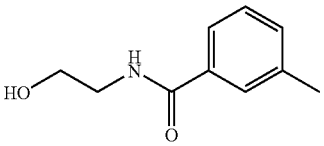 | 2HCl | MS · ESI: 404 [M + H]+ |
| 11.023 | 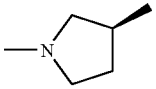 | 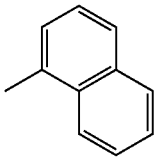 | 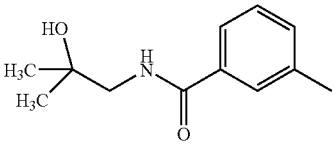 | 2HCl | MS · ESI: 432 [M + H]+ |
| 11.024 | 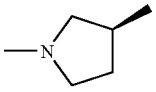 | 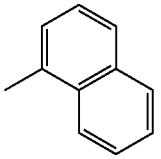 | 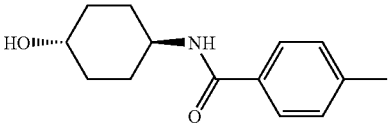 | Free form | MS · APCI: 458 [M + H]+ |
| 11.025 | 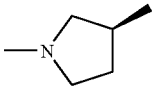 | 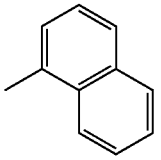 | 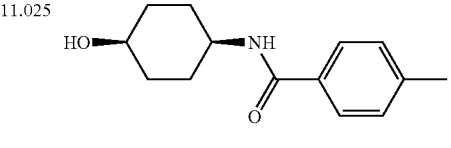 | Free form | MS · APCI: 458 [M + H]+ |
| 11.026 | 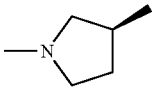 | 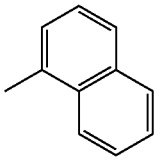 | 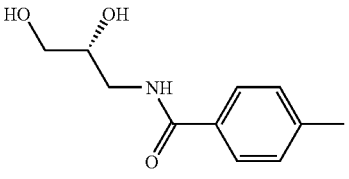 | Free form | MS · APCI: 434 [M + H]+ |
| 11.027 | 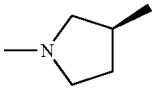 | 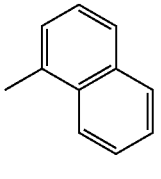 | 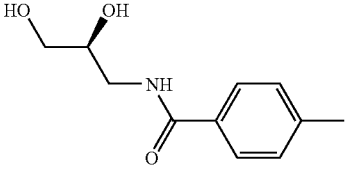 | 2HCl | MS · APCI: 434 [M + H]+ |
| 11.028 | 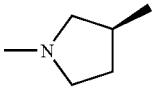 | 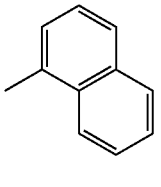 | 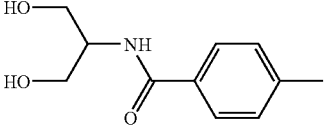 | Free form | MS · APCI: 434 [M + H]+ |
| 11.029 | 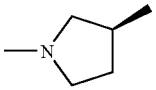 | 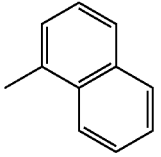 | 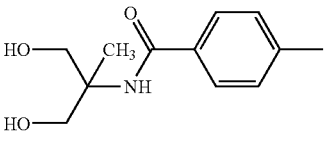 | Free form | MS · APCI: 448 [M + H]+ |

TABLE X-continued

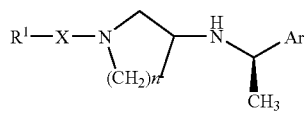

| Example No. | R¹—X— | 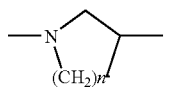 (CH₂)n' | —Ar | Salt | Physical properties, etc. |
|---|---|---|---|---|---|
| 11.030 | (HOCH₂)₂C(Et)-NH-C(O)-C₆H₄-CH₃ | N-methylpyrrolidin-3-yl | 1-methylnaphthyl | 2HCl | MS·APCI: 462 [M + H]+ |
| 11.031 | H₃C-O-C(O)-C(CH₃)₂-NH-C(O)-C₆H₄(m-CH₃) | N-methylpyrrolidin-3-yl | 1-methylnaphthyl | Free form | MS·APCI: 460 [M + H]+ |
| 11.032 | (CH₃)₂N-(CH₂)₃-NH-C(O)-C₆H₄-CH₃ | N-methylpyrrolidin-3-yl | 1-methylnaphthyl | 3HCl | MS·ESI: 445 [M + H]+ |
| 11.033 | CH₃-C(O)-NH-(CH₂)₂-NH-C(O)-C₆H₄-CH₃ | N-methylpyrrolidin-3-yl | 1-methylnaphthyl | 2HCl | MS·ESI: 445 [M + H]+ |
| 11.034 | 2-oxopyrrolidin-1-yl-(CH₂)₃-NH-C(O)-C₆H₄-CH₃ | N-methylpyrrolidin-3-yl | 1-methylnaphthyl | 2HCl | MS·ESI: 485 [M + H]+ |
| 11.035 | (CH₃)₂N-(CH₂)₂-NH-C(O)-C₆H₄-CH₃ | N-methylpiperidin-3-yl | 1-methylnaphthyl | 3HCl | MS·APCI: 445 [M + H]+ |

TABLE X-continued
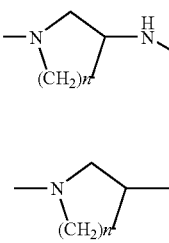
| Example No. | R¹—X— | $\underset{(CH_2)n}{N}$ | —Ar | Salt | Physical properties, etc. |
|---|---|---|---|---|---|
| 11.036 |  | 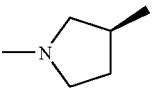 | 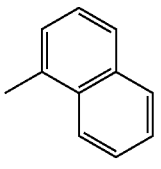 | 3HCl | MS · ESI: 431 [M + H]+ |
| 11.037 |  |  | 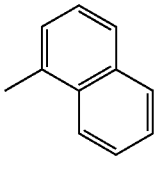 | 3HCl | MS · APCI: 487 [M + H]+ |
| 11.038 |  | 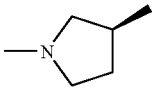 | 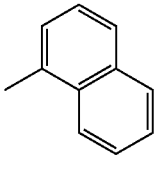 | 3HCl | MS · ESI: 473 [M + H]+ |
| 11.039 | 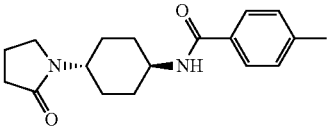 | 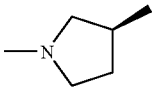 | 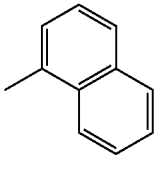 | 2HCl | MS · ESI: 525 [M + H]+ |
| 11.040 | 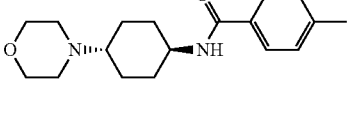 | 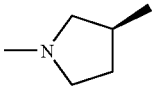 | 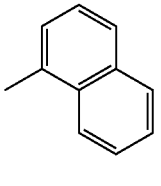 | 3HCl | MS · ESI: 527 [M + H]+ |
| 11.041 | 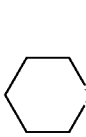 | 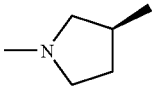 | 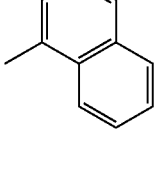 | 3HCl | MS · ESI: 471 [M + H]+ |
| 11.042 | 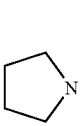 | 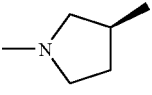 | 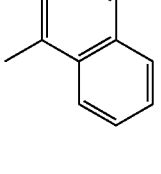 | 3HCl | MS · ESI: 457 [M + H]+ |

TABLE X-continued
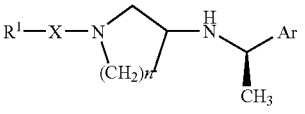
| Example No. | R¹—X— | 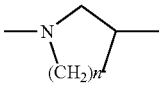 | —Ar | Salt | Physical properties, etc. |
|---|---|---|---|---|---|
| 11.043 | 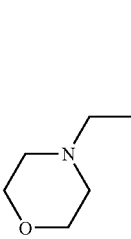 | 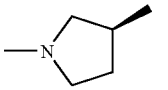 | 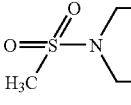 | 3HCl | MS·ESI: 487 [M + H]+ |
| 11.044 | 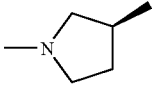 | 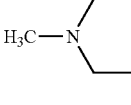 | 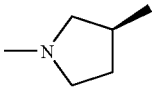 | Free form | MS·APCI: 521 [M + H]+ |
| 11.045 | 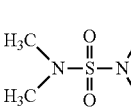 | 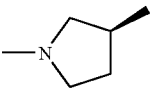 | 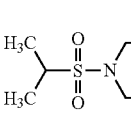 | Free form | MS·APCI: 471 [M + H]+ |
| 11.046 | 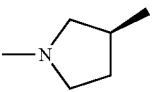 | | | 2HCl | MS·ESI: 550 [M + H]+ |
| 11.047 | 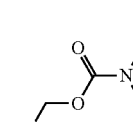 | | | 2HCl | MS·ESI: 549 [M + H]+ |
| 11.048 | 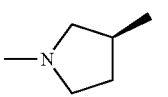 | | | 2HCl | MS·ESI: 515 [M + H]+ |
| 11.049 | 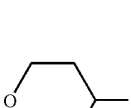 | 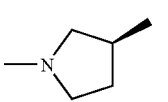 | | 2HCl | MS·ESI: 444 [M + H]+ |

TABLE X-continued
| Example No. | R¹—X— | 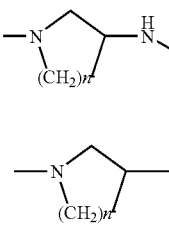 —N⟨(CH₂)n⟩ | —Ar | Salt | Physical properties, etc. |
|---|---|---|---|---|---|
| 11.050 | 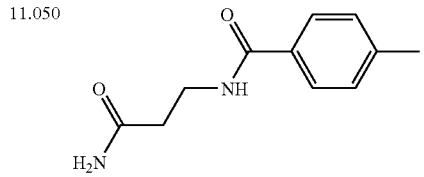 | 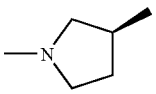 | 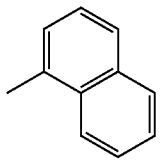 | 2HCl | MS · ESI: 431 [M + H]+ |
| 11.051 | 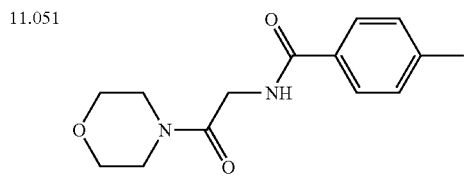 | 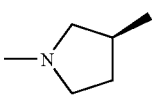 | 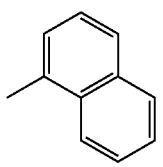 | 2HCl | MS · ESI: 487 [M + H]+ |
| 11.052 | 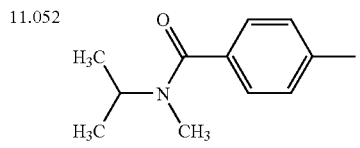 | 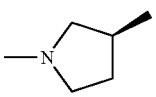 | 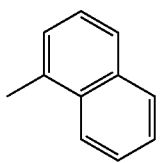 | 2HCl | MS · ESI: 416 [M + H]+ |
| 11.053 | 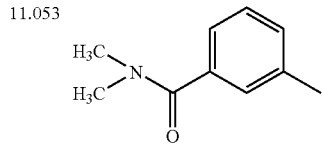 | 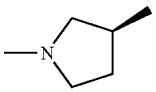 | 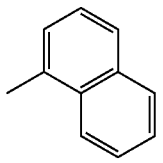 | 2HCl | MS · ESI: 388 [M + H]+ |
| 11.054 | 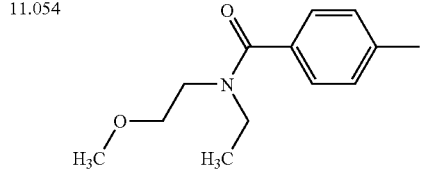 | 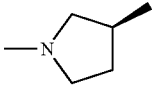 | 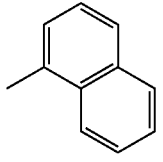 | 2HCl | MS · ESI: 446 [M + H]+ |
| 11.055 | 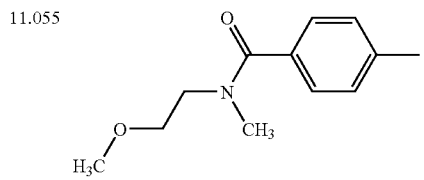 | 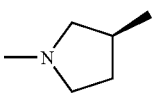 | 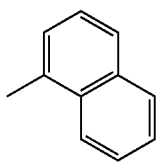 | 2HCl | MS · ESI: 432 [M + H]+ |
| 11.056 | 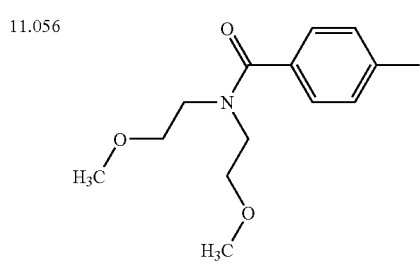 | 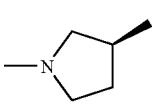 | 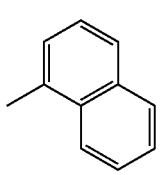 | 2HCl | MS · ESI: 476 [M + H]+ |

TABLE X-continued

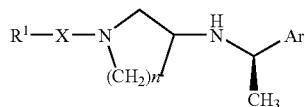

| Example No. | R¹—X— | —N(pyrrolidine)(CH₂)ₙ— | —Ar | Salt | Physical properties, etc. |
|---|---|---|---|---|---|
| 11.057 | HO-CH₂CH₂-N(CH₃)-C(O)-C₆H₄-CH₃ (p-tolyl) | 3-methylpyrrolidin-1-yl | 1-methylnaphthalen-? | 2HCl | MS·APCI: 418 [M+H]+ |
| 11.058 | (HOCH₂CH₂)₂N-C(O)-C₆H₄-CH₃ | 3-methylpyrrolidin-1-yl | 1-methylnaphthalen-? | Free form | MS·APCI: 448 [M+H]+ |
| 11.059 | (CH₃)₂N-CH₂CH₂-N(CH₃)-C(O)-C₆H₄-CH₃ | 3-methylpyrrolidin-1-yl | 1-methylnaphthalen-? | 2HCl | MS·ESI: 445 [M+H]+ |
| 11.060 | 4-carbamoylpiperidin-1-yl-C(O)-C₆H₄-CH₃ | 3-methylpyrrolidin-1-yl | 1-methylnaphthalen-? | 2HCl | MS·ESI: 471 [M+H]+ |
| 11.061 | pyrrolidin-1-yl-C(O)-C₆H₄-CH₃ | 3-methylpyrrolidin-1-yl | 1-methylnaphthalen-? | 2HCl | MS·ESI: 414 [M+H]+ |
| 11.062 | (2S)-2-(methoxymethyl)pyrrolidin-1-yl-C(O)-C₆H₄-CH₃ | 3-methylpyrrolidin-1-yl | 1-methylnaphthalen-? | 2HCl | MS·ESI: 458 [M+H]+ |

TABLE X-continued
| Example No. | R¹—X— | (ring) | —Ar | Salt | Physical properties, etc. |
|---|---|---|---|---|---|
| 11.063 | 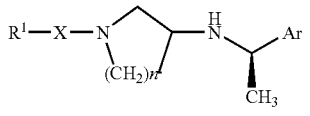 | 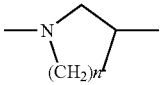 |  | 2HCl | MS · APCI: 430 [M + H]+ |
| 11.064 | 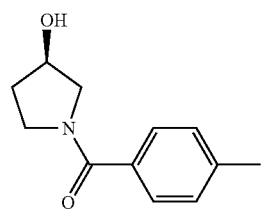 | 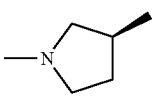 | 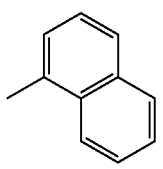 | Free form | MS · APCI: 444 [M + H]+ |
| 11.065 | 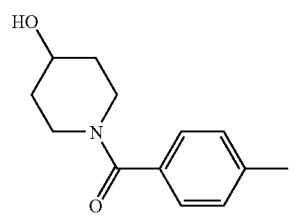 | 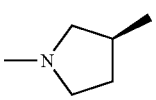 | 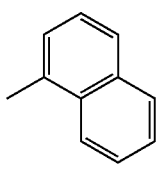 | 2HCl | MS · ESI: 521 [M + H]+ |
| 11.066 | 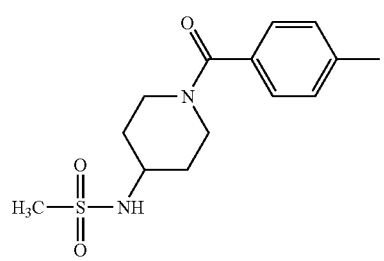 | 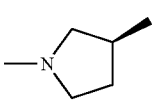 | 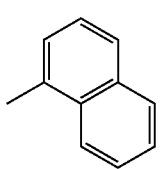 | 2HCl | MS · ESI: 430 [M + H]+ |
| 11.067 | 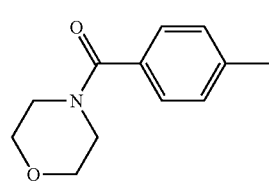 | 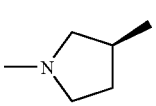 | 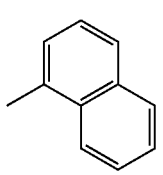 | 2HCl | MS · ESI: 507 [M + H]+ |
| 11.068 | 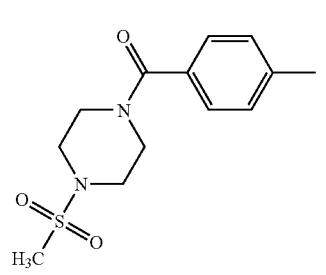 | 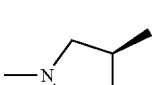 | 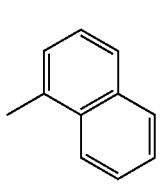 | 2HCl | MS · ESI: 443 [M + H]+ |

TABLE X-continued

| Example No. | R¹—X— | —N(pyrrolidine)(CH₂)ₙ— | —Ar | Salt | Physical properties, etc. |
|---|---|---|---|---|---|
| 11.069 | 4-methylpiperazinyl-C(O)-(4-methylphenyl)- | (R)-1-methyl-pyrrolidin-3-yl | 1-methylnaphthalen-yl | 3HCl | MS · ESI: 443 [M + H]+ |
| 11.070 | 4-ethylpiperazinyl-C(O)-(4-methylphenyl)- | (R)-1-methyl-pyrrolidin-3-yl | 1-methylnaphthalen-yl | 3HCl | MS · ESI: 457 [M + H]+ |
| 11.071 | 4-acetylpiperazinyl-C(O)-(4-methylphenyl)- | (R)-1-methyl-pyrrolidin-3-yl | 1-methylnaphthalen-yl | 2HCl | MS · ESI: 471 [M + H]+ |
| 11.072 | 4-(ethoxycarbonyl)piperazinyl-C(O)-(4-methylphenyl)- | (R)-1-methyl-pyrrolidin-3-yl | 1-methylnaphthalen-yl | 2HCl | MS · ESI: 501 [M + H]+ |
| 11.073 | 4-(ethylsulfonyl)piperazinyl-C(O)-(4-methylphenyl)- | (R)-1-methyl-pyrrolidin-3-yl | 1-methylnaphthalen-yl | 2HCl | MS · ESI: 521 [M + H]+ |
| 11.074 | (CH₃)₂N-C(O)-(6-methylpyridin-3-yl)- | (R)-1-methyl-pyrrolidin-3-yl | 1-methylnaphthalen-yl | 2HCl | MS · APCI: 389 [M + H]+ |

TABLE X-continued
| Example No. | R¹—X— | —N(CH₂)ₙ— | —Ar | Salt | Physical properties, etc. |
|---|---|---|---|---|---|
| 11.075 | 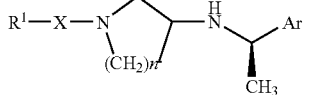 | 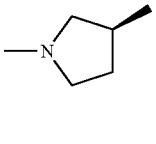 | 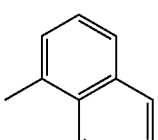 | 2HCl | MS · APCI: 417 [M + H]+ |
| 11.076 | 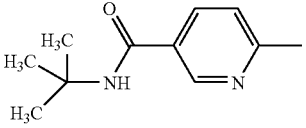 | 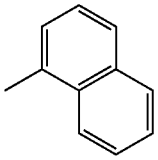 | 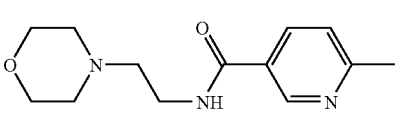 | Free form | MS · APCI: 405 [M + H]+ |
| 11.077 | 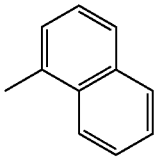 | 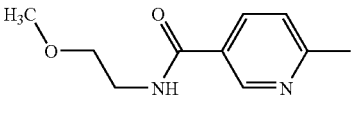 | 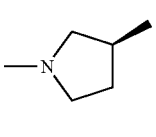 | 2HCl | MS · APCI: 433 [M + H]+ |
| 11.078 | 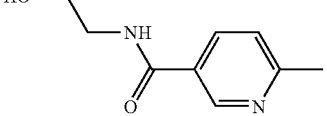 | 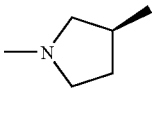 | 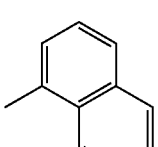 | 2HCl | MS · APCI: 419 [M + H]+ |
| 11.079 | 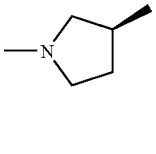 | 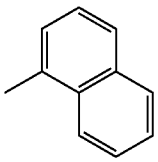 | 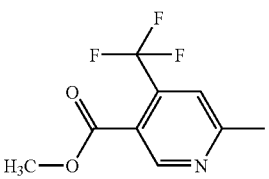 | 3HCl | MS · APCI: 432 [M + H]+ |
| 11.080 | 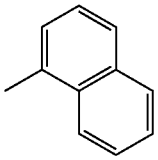 | 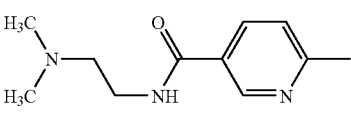 | 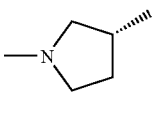 | 3HCl | MS · APCI: 474 [M + H]+ |
| 12.001 | 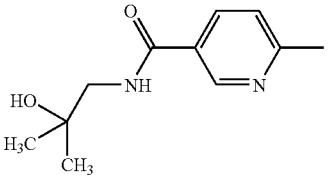 | 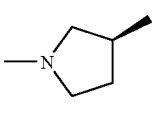 | 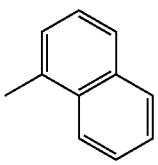 | Free form | MS · APCI: 444 [M + H]+ |

TABLE X-continued

| Example No. | R¹—X— | —N(CH₂)ₙ | —Ar | Salt | Physical properties, etc. |
|---|---|---|---|---|---|
| 12.002 | HOOC-CH₂-NH-C(O)-C₆H₄-CH₃ (p-tolyl, glycine amide) | N-methylpyrrolidin-3-yl | 1-methylnaphthyl | 2HCl | MS · APCI: 418 [M + H]+ |
| 12.003 | (S)-HOCH₂-CH(CH₃)-NH-C(O)-C₆H₄-CH₃ | N-methylpyrrolidin-3-yl | 1-methylnaphthyl | Free form | MS · APCI: 418 [M + H]+ |
| 12.004 | (R)-HOCH₂-CH(CH₃)-NH-C(O)-C₆H₄-CH₃ | N-methylpyrrolidin-3-yl | 1-methylnaphthyl | Free form | MS · APCI: 418 [M + H]+ |
| 12.005 | (S)-HOCH₂-CH(Ph)-NH-C(O)-C₆H₄-CH₃ | N-methylpyrrolidin-3-yl | 1-methylnaphthyl | Free form | MS · APCI: 480 [M + H]+ |
| 12.006 | (R)-HOCH₂-CH(Ph)-NH-C(O)-C₆H₄-CH₃ | N-methylpyrrolidin-3-yl | 1-methylnaphthyl | HCl | MS · APCI: 480 [M + H]+ |
| 12.007 | 4-(hydroxymethyl)piperidin-1-yl-C(O)-C₆H₄-CH₃ | N-methylpyrrolidin-3-yl | 1-methylnaphthyl | HCl | MS · APCI: 458 [M + H]+ |
| 12.008 | 2-(hydroxymethyl)pyrrolidin-1-yl-C(O)-C₆H₄-CH₃ | N-methylpyrrolidin-3-yl | 1-methylnaphthyl | HCl | MS · APCI: 444 [M + H]+ |

TABLE X-continued

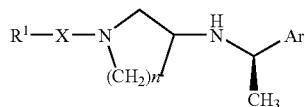

| Example No. | R¹—X— | —(CH₂)ₙ— | —Ar | Salt | Physical properties, etc. |
|---|---|---|---|---|---|
| 12.009 | (N-(4-methylbenzoyl)proline with COOH) | N-methylpyrrolidin-3-yl | 1-naphthyl | Free form | MS · APCI: 458 [M + H]+ |
| 12.010 | 2-methyl-2-[(2-methylbenzoyl)amino]propanoic acid | N-methylpyrrolidin-3-yl | 1-naphthyl | Free form | MS · APCI: 446 [M + H]+ |
| 12.011 | 2-methyl-2-[(3-methylbenzoyl)amino]propanoic acid | N-methylpyrrolidin-3-yl | 1-naphthyl | Free form | MS · APCI: 446 [M + H]+ |
| 12.012 | 2-methyl-2-[(4-methylbenzoyl)amino]propanoic acid | N-methylpyrrolidin-3-yl | 1-naphthyl | Free form | MS · APCI: 446 [M + H]+ |
| 12.013 | N-methyl-N-(4-methylbenzoyl)glycine | N-methylpyrrolidin-3-yl | 1-naphthyl | Free form | MS · APCI: 432 [M + H]+ |
| 12.014 | N-(4-methylbenzoyl)alanine | N-methylpyrrolidin-3-yl | 1-naphthyl | Free form | MS · APCI: 432 [M + H]+ |

TABLE X-continued
| Example No. | R¹—X— | (structure) | —Ar | Salt | Physical properties, etc. |
|---|---|---|---|---|---|
| 12.015 | 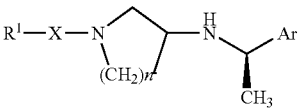 | 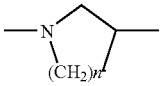 | 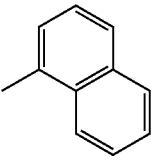 | Free form | MS·APCI: 494 [M + H]+ |
| 12.016 | 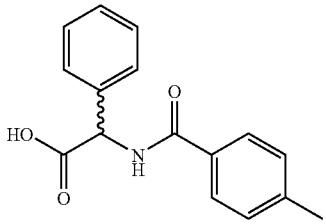 | 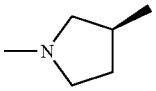 | 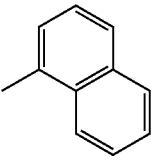 | Free form | MS·APCI: 472 [M + H]+ |
| 12.017 | 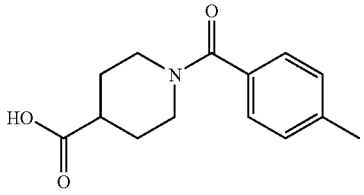 | 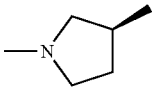 | 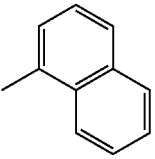 | HCl | MS·APCI: 409 [M + H]+ |
| 12.018 | 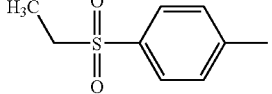 | 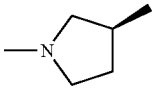 | 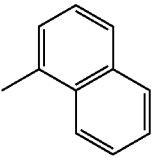 | Free form | MS·APCI: 424 [M + H]+ |
| 12.019 | 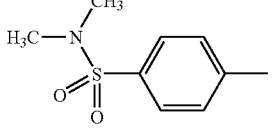 | 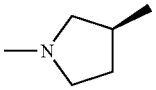 | 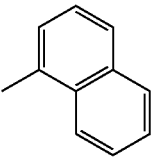 | Free form | MS·APCI: 452 [M + H]+ |
| 12.020 | 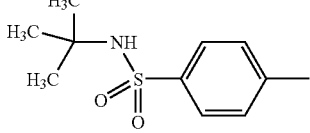 | 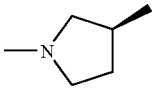 | 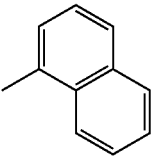 | 3HCl | MS·APCI: 467 [M + H]+ |
| 12.021 | 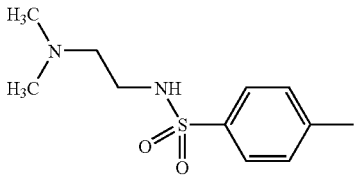 | 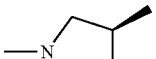 | 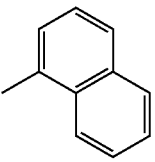 | 2HCl | MS·APCI: 440 [M + H]+ |

TABLE X-continued
| Example No. | R¹—X— | —N[(CH₂)n'] pyrrolidine | —Ar | Salt | Physical properties, etc. |
|---|---|---|---|---|---|
| 12.022 | 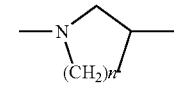 |  | 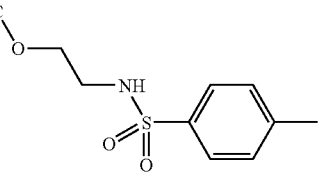 | 2HCl | MS · APCI: 454 [M + H]+ |
| 12.023 | 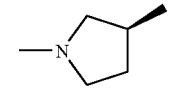 | 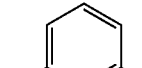 | 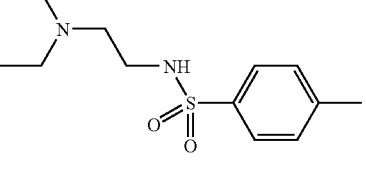 | 3HCl | MS · APCI: 509 [M + H]+ |
| 12.024 | 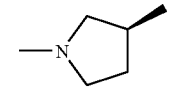 | 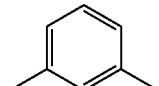 | 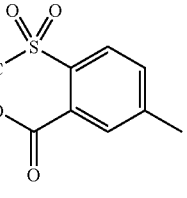 | Free form | MS · APCI: 439 [M + H]+ |
| 12.025 | 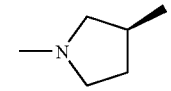 | 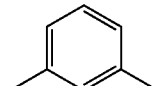 | 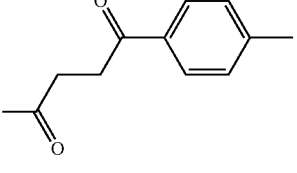 | Free form | MS · APCI: 417 [M + H]+ |
| 12.026 | 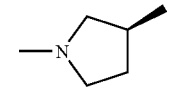 | 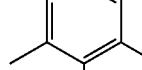 | 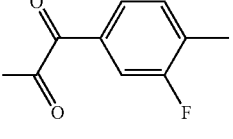 | Free form | MS · APCI: 407 [M + H]+ |
| 12.027 | 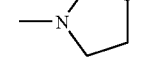 | 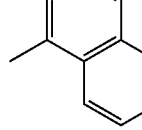 | 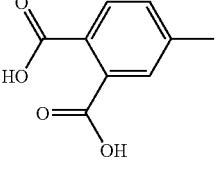 | Free form | MS · APCI: 405 [M + H]+ |
| 12.028 | 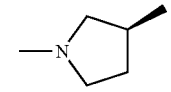 | 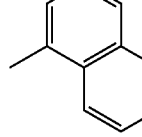 | 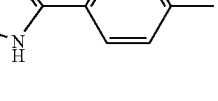 | HCl | MS · APCI: 385 [M + H]+ |

TABLE X-continued
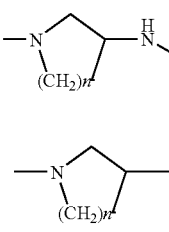
| Example No. | R¹—X— | (structure with N-(CH₂)ₙ) | —Ar | Salt | Physical properties, etc. |
|---|---|---|---|---|---|
| 12.029 |  | 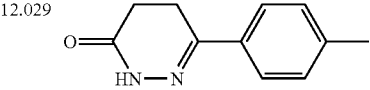 | 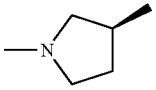 | Free form | MS·APCI: 413 [M + H]+ |
| 12.030 | 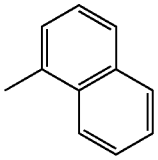 | 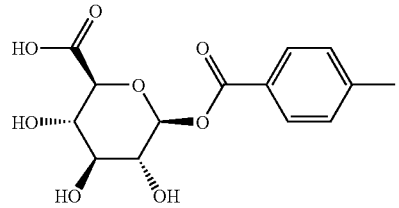 | 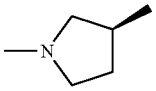 | Free form | MS·APCI: 537 [M + H]+ |
| 12.031 | 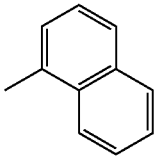 | 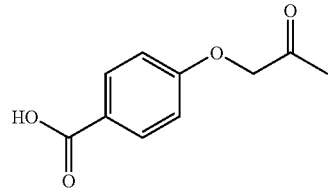 | 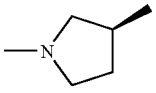 | Free form | MS·APCI: 419 [M + H]+ |
TABLE Y
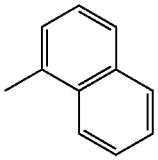
| Example No. | R¹—X— | (structure with N-(CH₂)ₙ) | —Ar | Salt | Physical properties, etc. |
|---|---|---|---|---|---|
| 13.001 | 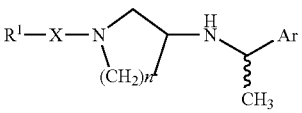 |  | 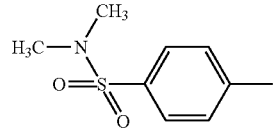 | 2HCl | MS·APCI: 404 [M + H]+ |
| 13.002 | 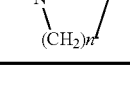 | 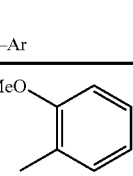 | 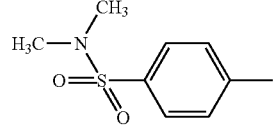 | Free form | MS·APCI: 388 [M + H]+ |
| 13.003 | 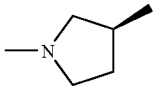 | 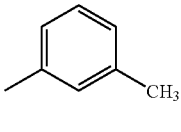 | 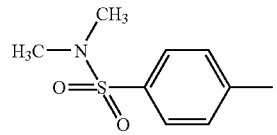 | 2HCl | MS·APCI: 430 [M + H]+ |

| Reference example Table | | | |
|---|---|---|---|
| Reference example No. | Structural formula | Salt | Physical properties, etc. |
| 1.001 1.004 | | 2HCl | MS · APCI: 221 [M + H]+ |
| 1.002 1.003 | | 2HCl | MS · APCI: 221 [M + H]+ |
| 1.005 (a) | | 2HCl | MS · APCI: 241 [M + H]+ |
| 1.005 (b) | | 2HCl | MS · APCI: 241 [M + H]+ |
| 1.006 (a) | | Free form | MS · APCI: 441 [M + H]+ |
| 1.006 (b) | | Free form | MS · APCI: 441 [M + H]+ |
| 2.001 | | 2HCl | MS · APCI: 228 [M + H]+ |
| 3.001 (a) | | Free form | MS · APCI: 255 [M + H]+ |

| Reference example No. | Structural formula | Salt | Physical properties, etc. |
|---|---|---|---|
| 3.001 (b) | 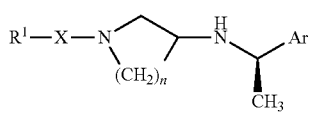 | 2HCl | MS · APCI: 255 [M + H]+ |

The invention claimed is:

1. An arylalkylamine compound represented by the formula [I-e]:

$$R^1-X-N\underset{(CH_2)_n}{\overset{}{\diagdown}}\overset{H}{N}\underset{CH_3}{\diagdown}Ar \quad [\text{I-e}]$$

the symbols in the formula represent the following meanings:

Ar: represents naphthyl optionally substituted by one or more groups selected from the group consisting of halogen, hydroxy, cyano, halo-lower alkyl, lower alkyl, lower alkoxy and lower alkylthio;

$R^1$: represents a monocyclic heterocyclic group selected from pyrrolyl, thienyl, thiazolyl, piperidyl, piperazinyl, morpholinyl, pyridyl, pyrimidinyl, pyradinyl and pyridazinyl, each of which is optionally substituted by substituent(s) selected from the following Substituent group Q1:

<Substituent group Q1> halogen cyano nitro oxo group hydroxy carboxy optionally substituted lower alkyl which may be optionally substituted by 1 or plural groups selected from halogen, cyano, nitro, oxo, carboxy, hydroxy, lower alkoxy and halo-lower alkoxy optionally substituted lower alkoxy which may be optionally substituted by 1 or plural groups selected from halogen, cyano, nitro, oxo, carboxy and hydroxy optionally substituted amino which may be mono- or di-substituted by a group selected from lower alkyl, and halo-lower alkyl optionally substituted 5 to 6-membered monocyclic heterocyclic group which may be optionally substituted by 1 or plural groups selected from halogen, cyano, nitro, oxo, carboxy, hydroxy, lower alkyl, halo-lower alkyl, lower alkoxy, halo-lower alkoxy and acyl optionally substituted phenyl which may be optionally substituted by 1 or plural groups selected from halogen, cyano, nitro, oxo, carboxy, hydroxy, lower alkyl, halo-lower alkyl, lower alkoxy, halo-lower alkoxy and acyl acyl;

n: is an integer of 1 to 3;

X: represents single bonding arm;

or a pharmaceutically acceptable salt thereof, provided that compounds wherein Ar represents optionally substituted naphthyl; $R^1$ represents an optionally substituted phenyl; and n is 2; or pharmaceutically acceptable salts thereof, are excluded.

2. The compound according to claim 1 or a pharmaceutically acceptable salt thereof, wherein n is 1 or 2.

3. The compound according to claim 1 or a pharmaceutically acceptable salt thereof, wherein n is 2.

4. The compound according to claim 1 or a pharmaceutically acceptable salt thereof, wherein Ar is a group which may be optionally substituted by group(s) selected from lower alkyl and lower alkoxy.

5. The compound according to claim 1 or a pharmaceutically acceptable salt thereof, wherein when $R^1$ is optionally substituted phenyl, the substituent(s) is selected from carboxy, halogen, unsubstituted or substituted lower alkyl, unsubstituted or substituted lower alkoxy, acyl and optionally substituted 5 to 6-membered monocyclic heterocyclic group.

6. A pharmaceutical composition comprising:
the compound according to claim 1 or a pharmaceutically acceptable salt thereof as an effective ingredient; and
a pharmaceutically acceptable carrier.

7. The pharmaceutical composition according to claim 6, wherein it is for activation of CaSR and/or suppression of PTH production.

8. The compound according to claim 1 or a pharmaceutically acceptable salt thereof, wherein Ar is unsubstituted naphthyl.

9. The compound according to claim 1, which is

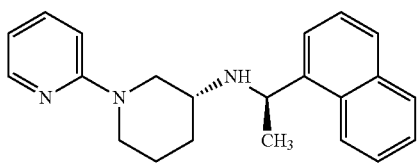 [SMILES: C[C@@H](N[C@@H]1CCCN(c2ccccn2)C1)c1cccc2ccccc12]

or a pharmaceutically acceptable salt thereof.

10. An arylalkylamine compound represented by the formula [I-e]:

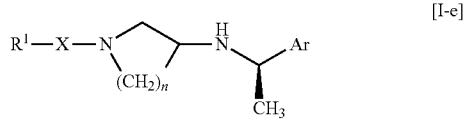

the symbols in the formula represent the following meanings:

Ar: represents naphthyl optionally substituted by one or more groups selected from the group consisting of halogen, hydroxy, cyano, lower alkyl, lower alkoxy and lower alkylthio;

$R^1$: represents a monocyclic heterocyclic group selected from pyrrolyl, thienyl, thiazolyl, piperidyl, piperazinyl, morpholinyl, pyridyl, pyrimidinyl, pyradinyl and pyridazinyl, each of which is optionally substituted by substituent(s) selected from the following Substituent group Q1:

<Substituent group Q1>
halogen
cyano
oxo group
carboxy
optionally substituted lower alkyl which may be optionally substituted by 1 or plural groups of a halogen
carboxy-lower alkyl
optionally substituted lower alkoxy which may be optionally substituted by 1 or plural groups of a halogen
optionally substituted amino which may be mono- or di-substituted by a lower alkyl
optionally substituted phenyl which may be optionally substituted by 1 or plural groups selected from halogen, cyano, lower alkyl, lower alkoxy, and halo-lower alkoxy
lower alkanoyl
carbamoyl;
n: is an integer of 1 to 3;
X: represents single bonding arm;

or a pharmaceutically acceptable salt thereof,
provided that compounds wherein Ar represents optionally substituted naphthyl; $R^1$ represents an optionally substituted phenyl; and n is 2; or pharmaceutically acceptable salts thereof, are excluded.

11. The compound according to claim 10 or a pharmaceutically acceptable salt thereof, wherein n is 1 or 2.

12. The compound according to claim 10 or a pharmaceutically acceptable salt thereof, wherein n is 2.

13. The compound according to claim 10 or a pharmaceutically acceptable salt thereof, wherein Ar is a group which may be optionally substituted by group(s) selected from lower alkyl and lower alkoxy.

14. A pharmaceutical composition comprising:
the compound according to claim 10 or a pharmaceutically acceptable salt thereof as an effective ingredient; and
a pharmaceutically acceptable carrier.

15. The pharmaceutical composition according to claim 14, wherein it is for activation of CaSR and/or suppression of PTH production.

16. The compound according to claim 10 or a pharmaceutically acceptable salt thereof, wherein Ar is unsubstituted naphthyl.

* * * * *